United States Patent
Lin et al.

(10) Patent No.: US 8,436,015 B2
(45) Date of Patent: May 7, 2013

(54) GLUCAGON RECEPTOR ANTAGONIST COMPOUNDS, COMPOSITIONS CONTAINING SUCH COMPOUNDS AND METHODS OF USE

(75) Inventors: Songnian Lin, Monroe, NJ (US); Christian P. Stevenson, Hoboken, NJ (US); Emma R. Parmee, Scotch Plains, NJ (US); Libo Xu, Bridgewater, NJ (US); Xibin Liao, Edison, NJ (US); Edward Metzger, Somerset, NJ (US); Rui Liang, East Brunswick, NJ (US); Fengqi Zhang, Edison, NJ (US); John E. Stelmach, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 32 days.

(21) Appl. No.: 13/063,820

(22) PCT Filed: Sep. 10, 2009

(86) PCT No.: PCT/US2009/056436
§ 371 (c)(1),
(2), (4) Date: Mar. 14, 2011

(87) PCT Pub. No.: WO2010/030722
PCT Pub. Date: Mar. 18, 2010

(65) Prior Publication Data
US 2011/0172256 A1 Jul. 14, 2011

Related U.S. Application Data

(60) Provisional application No. 61/192,080, filed on Sep. 15, 2008.

(51) Int. Cl.
*A01N 43/42* (2006.01)
*A61K 31/47* (2006.01)
*C07D 215/00* (2006.01)

(52) U.S. Cl.
USPC .......................................... 514/312; 546/155

(58) Field of Classification Search ........................ None
See application file for complete search history.

(56) References Cited

U.S. PATENT DOCUMENTS

| | | |
|---|---|---|
| 2005/0272794 A1 | 12/2005 | Parmee et al. |
| 2006/0084681 A1 | 4/2006 | Parmee et al. |
| 2007/0088071 A1 | 4/2007 | Kim et al. |
| 2007/0105930 A1 | 5/2007 | Parmee et al. |
| 2007/0203186 A1 | 8/2007 | Beeson et al. |
| 2008/0085926 A1 | 4/2008 | Stelmach et al. |
| 2008/0108620 A1 | 5/2008 | Brockunier et al. |
| 2008/0161347 A1 | 7/2008 | Stelmach et al. |
| 2009/0054506 A1 | 2/2009 | Liang et al. |
| 2009/0054662 A1 | 2/2009 | Tan et al. |
| 2009/0105310 A1 | 4/2009 | Kim et al. |
| 2009/0176854 A1 | 7/2009 | Parmee et al. |
| 2009/0209564 A1 | 8/2009 | Kim et al. |
| 2009/0215825 A1 | 8/2009 | Parmee et al. |
| 2010/0144824 A1 | 6/2010 | Stelmach et al. |
| 2011/0065634 A1 | 3/2011 | Greenlee et al. |
| 2011/0178007 A1 | 7/2011 | Stamford et al. |
| 2011/0251248 A1 | 10/2011 | Lin et al. |
| 2011/0281795 A1 | 11/2011 | Lin et al. |
| 2011/0301082 A1 | 12/2011 | Lin et al. |
| 2011/0312911 A1 | 12/2011 | Kats-Kagan et al. |
| 2012/0010262 A1 | 1/2012 | Chung et al. |

FOREIGN PATENT DOCUMENTS

| | | |
|---|---|---|
| WO | 2006/102067 | 9/2006 |
| WO | 2008/042223 | 4/2008 |
| WO | 2010/080971 | 7/2010 |
| WO | 2010/144664 | 12/2010 |
| WO | 2011/037815 | 3/2011 |
| WO | 2011/119541 | 9/2011 |
| WO | 2011/119559 | 9/2011 |

OTHER PUBLICATIONS

Int'l Search Report of PCT/US2009/056436, mailed Jan. 18, 2010.
Int'l Preliminary Report on Patentability of PCT/US2009/056436, issued Mar. 15, 2011.

*Primary Examiner* — Jeffrey Murray
(74) *Attorney, Agent, or Firm* — Anna L. Cocuzzo; John C. Todaro

(57) ABSTRACT

Glucagon receptor antagonist compounds of formula I are disclosed:

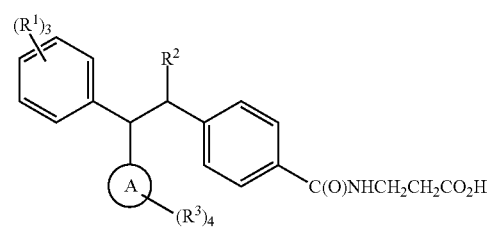

The compounds are useful for treating type 2 diabetes and related conditions. Pharmaceutical compositions and methods of treatment are also included.

17 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

A compound represented by formula I:

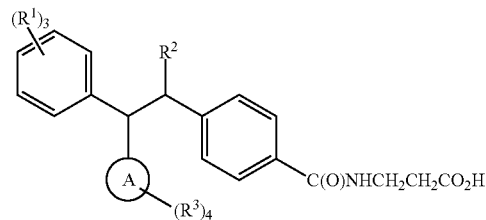

or a pharmaceutically acceptable salt thereof wherein:

ring A represents a heteroaryl group containing two six membered rings and one or two nitrogen atoms;

each $R^1$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy, and each $R^3$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo, $NR^aR^b$, and $C_{1-6}$alkoxy;

or 3 $R^3$ groups are as described above and 1 $R^3$ represents a 5-6 membered heteroaryl ring containing 0-1 oxygen or sulfur atom and 1-4 nitrogen atoms, said heteroaryl group being optionally substituted with 1-2 halo, $C_{1-3}$alkyl, $C_{2-3}$alkenyl or $C_{1-3}$alkoxy groups, the alkyl and alkenyl portions of, $C_{1-3}$alkyl, $C_{2-3}$alkenyl and $C_{1-3}$alkoxy being optionally substituted with 1-3 halo atoms up to perhalo; and further optionally substituted with 1 group selected from OH, oxo and $C_{1-6}$alkoxy, said heteroaryl ring being further optionally substituted with a member selected from the group consisting of CN, OH, $NO_2$, $CO_2R^a$, $NR^aR^b$ and $S(O)_pR^a$.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. Cycloalkenyl is a subset of alkenyl. If no number is specified, 4-8 carbon atoms are included. Examples include cyclopentenyl, cyclohexenyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indenyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

Ring A represents a heteroaryl group containing two six membered rings and one or two nitrogen atoms. Examples of such heteroaryl groups include quinoline, isoquinoline, cinnoline, quinazoline, quinoxaline, naphthridine and phthalazine, attached through any available point of attachment. Typically ring A is linked to the carbon atom to which it is attached through a carbon atom, thus forming a carbon-carbon bond.

"Halogen" (Halo) includes fluorine, chlorine, bromine and iodine.

One aspect of the invention relates to a compound represented by formula I:

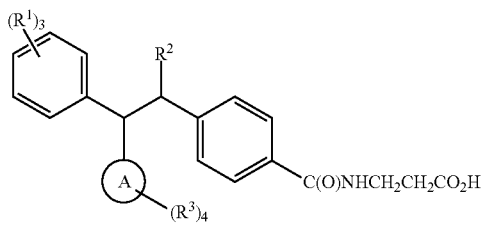

or a pharmaceutically acceptable salt thereof wherein:

ring A represents a heteroaryl group containing two six membered rings and one or two nitrogen atoms;

each $R^1$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy, and each $R^3$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo, $NR^aR^b$, and $C_{1-6}$alkoxy;

or 3 $R^3$ groups are as described above and 1 $R^3$ represents a 5-6 membered heteroaryl ring containing 0-1 oxygen or sulfur atom and 1-4 nitrogen atoms, said heteroaryl group being optionally substituted with 1-2 halo, $C_{1-3}$alkyl, $C_{2-3}$alkenyl or $C_{1-3}$alkoxy groups, the alkyl and alkenyl portions of, $C_{1-3}$alkyl, $C_{2-3}$alkenyl and $C_{1-3}$alkoxy being optionally substituted with 1-3 halo atoms up to perhalo; and further optionally substituted with 1 group selected from OH, oxo and $C_{1-6}$alkoxy, said heteroaryl ring being further optionally substituted with a member selected from the group consisting of CN, OH, $NO_2$, $CO_2R^a$, $NR^aR^b$ and $S(O)_pR^a$.

An aspect of the invention that is of interest relates to compounds in accordance with formula I or a pharmaceutically acceptable salt thereof wherein ring A represents a quinolinyl, isoquinolinyl or quinazolinyl group.

More particularly, an aspect of the invention that is of interest relates to compounds in accordance with formula I or a pharmaceutically acceptable salt thereof wherein ring A represents a quinolinyl group.

Also more particularly, an aspect of the invention that is of interest relates to compounds in accordance with formula I or a pharmaceutically acceptable salt thereof wherein ring A represents a quinazolinyl group.

Also more particularly, an aspect of the invention that is of interest relates to compounds in accordance with formula I or a pharmaceutically acceptable salt thereof wherein ring A represents an isoquinolinyl group.

Another aspect of the invention that is of interest relates to compounds in accordance with formula I or a pharmaceutically acceptable salt thereof wherein each $R^1$ represents H or is selected from the group consisting of halo selected from fluoro and chloro; $SCH_3$; CN, $C_{1-6}$alkyl, $C_{2-4}$alkenyl and $C_{1-6}$alkoxy, the alkyl and alkenyl portions of $SCH_3$, $C_{2-4}$alkenyl and $C_{1-6}$alkoxy being optionally substituted with 1-3 fluoro atoms.

In particular, another aspect of the invention that is of interest relates to compounds in accordance with formula I or a pharmaceutically acceptable salt thereof wherein each $R^1$ represents H or is selected from the group consisting of: fluoro, chloro; $SCH_3$; $CH_3$; $OCH_3$; $CF_3$; and $OCF_3$.

More particularly, another aspect of the invention that is of interest relates to compounds in accordance with formula I or a pharmaceutically acceptable salt thereof wherein each $R^1$ represents H or is selected from the group consisting of 3-fluoro, 4-fluoro, 5-fluoro, 3-chloro, 4-chloro, 5-chloro, 4-methyl, 4-methoxy, 4-$CF_3$ and 4-$OCF_3$.

Another aspect of the invention that is of interest relates to compounds in accordance with formula I or a pharmaceutically acceptable salt thereof wherein $R^2$ represents a member selected from the group consisting of: $CH_3$, ethyl, n-propyl, isopropyl, n-, s- and t-butyl, isobutyl, neopentyl, and allyl, all optionally substituted with 1-3 fluoro atoms.

In particular, another aspect of the invention that is of interest relates to compounds in accordance with formula I or a pharmaceutically acceptable salt thereof wherein $R^2$ represents a member selected from the group consisting of: ethyl, n-propyl, and —$CH_2CH_2CF_3$.

Another aspect of the invention that is of interest relates to compounds in accordance with formula I or a pharmaceutically acceptable salt thereof wherein each $R^3$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy.

In particular, another aspect of the invention that is of interest relates to compounds in accordance with formula I or a pharmaceutically acceptable salt thereof wherein three $R^3$ groups represent H or halo, and one $R^3$ group represents a 5-6 membered heteroaryl ring containing 0-1 oxygen or sulfur atom and 1-4 nitrogen atoms, said heteroaryl group being optionally substituted with 1-2 halo, $C_{1-3}$alkyl, $C_{2-3}$alkenyl or $C_{1-3}$alkoxy groups, the alkyl and alkenyl portions of, $C_{1-3}$alkyl, $C_{2-3}$alkenyl and $C_{1-3}$alkoxy being optionally substituted with 1-3 halo atoms up to perhalo; and further optionally substituted with 1 group selected from OH, oxo and $C_{1-6}$alkoxy, and said heteroaryl ring being further optionally substituted with a member selected from the group consisting of CN, OH, $NO_2$, $CO_2R^a$, $NR^aR^b$ and $S(O)_pR^a$.

More particularly, an aspect of the invention that is of interest relates to compounds in accordance with formula I or a pharmaceutically acceptable salt thereof wherein each $R^3$ represents H or is selected from the group consisting of fluoro, chloro; $SCH_3$; CN, $C_{1-10}$alkyl, $C_{2-10}$alkenyl and $C_{1-10}$alkoxy, the alkyl portions of $SCH_3$, $C_{1-10}$alkyl, $C_{2-10}$alkenyl and $C_{1-10}$alkoxy being optionally substituted with 1-3 fluoro atoms.

Even more particularly, an aspect of the invention that is of interest relates to compounds in accordance with formula I or a pharmaceutically acceptable salt thereof wherein each $R^3$ represents H or is selected from the group consisting of fluoro, chloro; methyl, ethyl, methoxy, ethoxy, n-propyloxy, isopropyloxy, isobutyloxy, cyclobutyloxy, cyclopentyloxy, cyclohexyloxy, methoxyethoxy, dimethylaminoethoxy, cyano, trifluoromethyl, trifluoromethoxy, difluoromethoxy, pyrrolo, pyrazolo, isoxazolo and dimethylisoxazolo.

Another more particular aspect of the invention that is of interest relates to compounds in accordance with formula I or a pharmaceutically acceptable salt thereof wherein one $R^3$ represents a 5-6 membered heteroaryl ring containing 0-1 oxygen or sulfur atom and 1-4 nitrogen atoms.

Another aspect of the invention that is of interest relates to compounds of formula I or a pharmaceutically acceptable salt thereof wherein $R^a$ is selected from the group consisting of H, Me, Et, n-propyl, n-butyl and benzyl.

A subset of the invention described herein that is of interest relates to compounds of formula I or a pharmaceutically acceptable salt thereof wherein:

ring A represents a quinolinyl, isoquinolinyl or quinazolinyl group;

each $R^1$ represents H or is selected from the group consisting of halo selected from fluoro and chloro; $SCH_3$; CN, $C_{1-6}$alkyl, $C_{2-4}$alkenyl and $C_{1-6}$alkoxy, the alkyl and alkenyl portions of $SCH_3$, $C_{1-6}$alkyl, $C_{2-4}$alkenyl and $C_{1-6}$alkoxy being optionally substituted with 1-3 fluoro atoms;

$R^2$ represents a member selected from the group consisting of: $CH_3$, ethyl, n-propyl, isopropyl, n-, s- and t-butyl, isobutyl, neopentyl, and allyl, all optionally substituted with 1-3 fluoro atoms;

each $R^3$ represents H or is selected from the group consisting of halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of, $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2; and each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the list provided below.

Compounds of formula I may be used in combination with other drugs that are used in the treatment/prevention/suppression or amelioration of the diseases or conditions for which compounds of formula I are useful. Such other drugs may be administered, by a route and in an amount commonly used therefore, contemporaneously or sequentially with a compound of formula I. When a compound of formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I.

Examples of other active ingredients that may be combined with a compound of formula I for the treatment or prevention of type 2 diabetes and the other conditions described herein, either administered separately or in the same pharmaceutical compositions, include, but are not limited to:

(a) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) 33-adrenoreceptor agonists, such as AD9677/TAK677 (DainipponlTakeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081x, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653;

6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004439909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yppropyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6, beta-Ala11, Phe13, Nle14]Bn(6-14) and [D-Phe6, Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046, 167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, G1-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phemnetrazine; (86) picilorex; (87) phytopharm 57; (88) zonisamide, (89) neuromedin U and analogs or derivatives thereof, (90) oxyntomodulin and analogs or derivatives thereof, (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; and (92) Qnexa; and (e) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanaphenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharamecueitcally acceptable salts thereat as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(5)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl) azetidin-1-yl)(4-chlorophenyl)methyl]benzonitrile, 3-[(5)-(4-cyanophenyl)(3-{(1S)-2-fluoro-1-[3-fluoro-5-(5-oxo-4, 5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanaphenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]

methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidin)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl-}6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-(4-{3-(1-piperidinyl)propoxy]phenyl)-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763; or a pharmaceutically acceptable salts thereof. Examples of other anti-obesity agents that can be employed in combination with a compound of formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest, Drugs,* 9: 1553-1571 (2000).

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions, delaying the onset or reducing the risk of developing said condition, comprising administering to a mammalian patient in need of such treatment therapeutically effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin, and evermore particularly, a statin selected from the group consisting of: lovastatin, simvastatin, pravastatin, fluvastatin, atorvastatin, itavastatin, ZD-4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin or atorvastatin.

Another aspect of the invention that is of interest relates to a method for delaying the onset or reducing the risk of developing atherosclerosis in a human patient in need of such treatment comprising administering to said patient effective amounts of a compound of formula as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

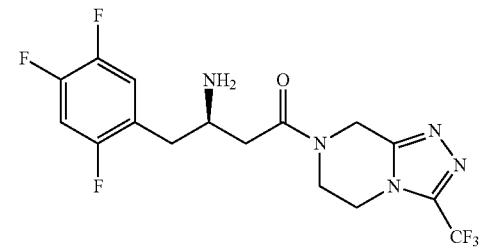 [SMILES: N[C@@H](CC(=O)N1CCn2c(nnc2C(F)(F)F)C1)Cc1cc(F)c(F)cc1F]

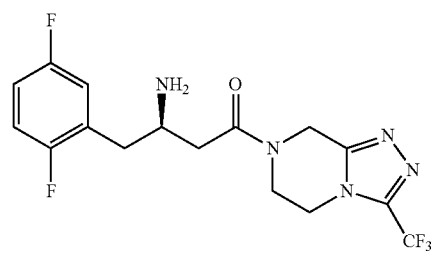 [SMILES: N[C@@H](CC(=O)N1CCn2c(nnc2C(F)(F)F)C1)Cc1cc(F)ccc1F]

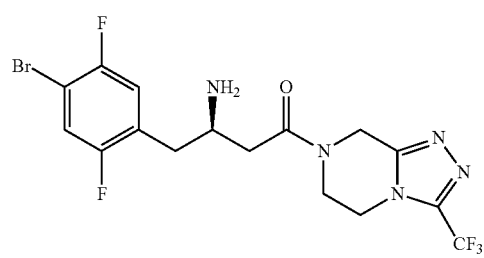 [SMILES: N[C@@H](CC(=O)N1CCn2c(nnc2C(F)(F)F)C1)Cc1cc(F)c(Br)cc1F]

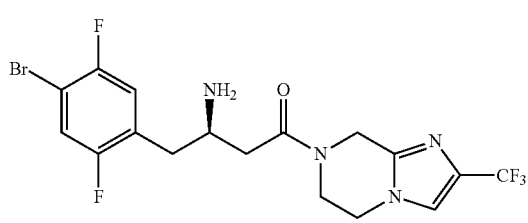 [SMILES: N[C@@H](CC(=O)N1CCn2cc(C(F)(F)F)nc2C1)Cc1cc(F)c(Br)cc1F]

or a pharmaceutically acceptable salt or solvate thereof in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amout ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg, 10 mg and 20 mg.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human, with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
| --- | --- | --- | --- |
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |

-continued

| Injectable Suspension (im.) | mg/mL | Tablet | Mg/tablet |
|---|---|---|---|
| Benzalkonium chloride | 1.0 | Magnesium Stearate | 2.5 |
| Water for injection | t.d. 1.0 mL | Total | 500 mg |

| Capsule | mg/ capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

An aspect of the invention that is particular interest relates to a pharmaceutical composition that is comprised of a compound of formula I, or a pharmaceutically acceptable salt thereof, and a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, metformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide, rimonabant and taranabant, in combination with a pharmaceutically acceptable carrier.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, $5^{th}$ Ed., John Wiley and Sons, New York, N.Y., 2001; *Advanced Organic Chemistry*, Carey and Sundberg, Vol. A and B, $3^{rd}$ Ed., Plenum Press, Inc., New York, N.Y., 1990; *Protective groups in Organic Synthesis*, Green and Wuts, $2^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, $2^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Acros, (Pittsburgh, Pa.); BioBlocks, Inc. (San Diego, Calif.); and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnaesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

Throughout the synthesis schemes, abbreviations are used with the following meanings unless otherwise indicated:

| | |
|---|---|
| AIBN = azobisisobutyronitrile | aq = aqueous |
| BINAP = 2,2'-bis(diphenylphosphino)-1,1'-binaphthalene | Bn = benzyl |
| BOC, Boc = t-butyloxycarbonyl | BOP = benzotriazol-1-yloxy-tris(dimethylamino)-phosphonium hexafluorophosphate |
| Bu = butyl, t-Bu = t-butyl | BuLi, n-BuLi = n-butyllithium |
| CBZ, Cbz = Benzyloxycarbonyl | DCM = dichloromethane |
| 2,4-diClPh = 2,4-dichlorophenyl | DIEA = diisopropylethylamine |
| DMAP = 4-Dimethylaminopyridine | DMF = N,N-dimethylformamide |
| DMS = dimethyl sulfide | DMSO = dimethyl sulfoxide |
| EDC = 1-ethyl-3-(3-dimethylaminopropyl)-carbodiimide | eq. = equivalent(s) |
| Et = ethyl | EtOAc = ethyl acetate |
| EtOH = ethanol | g = gram(s) |
| HOBT, HOBt = Hydroxybenztriazole | HPLC = High pressure liquid chromatography |
| IPA = isopropanol | iPr = isopropyl |
| KHMDS = potassium bis(trimethylsilyl)amide | KOtBu = potassium tert-butoxide |
| LC/MS = liquid chromatography - mass spectroscopy | LDA = lithium diisopropylamide |
| LHMDS = lithium bis(trimethylsilyl)amide | M = molar |
| mCPBA = 3-chloroperoxybenzoic acid | Me = methyl |
| MeCN, $CH_3CN$ = acetonitrile | MeOH = methanol |
| mg = milligram(s) | mL = milliliter(s) |
| mmol = millimole(s) | N = normal |
| NaOtBu = sodium tert-butoxide | NBS = N-bromosuccinimide |
| NCS = N-chlorosucciniamide | n-Pr = n-propyl |
| PCC = pyridinium chlorochromate | Pd/C = palladium on activated carbon |
| Ph = phenyl | PyBOP = Benzotriazol-1-yloxytripyrrolidinophosphonium hexafluorophosphate |
| RT, rt = room temperature | TBAF = tetrabutylammonium fluoride |
| TFA = Trifluoroacetic acid | THF = tetrahydrofuran |
| TMS = trimethylsilyl | triflate = trifluoromethanesulonate |

Compounds of the present invention may be prepared according to the methodology outlined in the following general synthetic schemes.

In one embodiment of the present invention, compound I may be prepared from the ester 1 by the sequence depicted in Scheme 1. Saponification of ester 1 (methyl, ethyl and t-butyl) to give compound 2 is achieved with a base such as aqueous lithium hydroxide (LiOH) or aqueous sodium hydroxide in a polar solvent such as tetrahydrofuran, methanol, ethanol or a mixture of similar solvents. In addition, compound 1, containing a t-butyl ester, can be converted to compound 2 using acid such as acetic acid or trifluoroacetic acid (TFA). The carboxylic acid intermediate 2 can be coupled with commercially available beta alanine ester (either methyl, ethyl or t-butyl ester) using benzotriazol-1-yloxy-tris(dimethylamino)-phosphonium hexafluorophosphate (BOP) and a base, generally N,N-diisopropylethylamine (DIEA), in a solvent such as dichloromethane or N,N-dimethylformamide (DMF) at ambient temperature to yield amide 3. Alternatively, the conversion of 2 to 3 may be carried out with EDC, HOBt, and a base such as DIEA in similar solvents as those used with BOP and DMA. Many additional peptide coupling conditions are known and may also be used. Compound I may then be accessed by conversion of the ester group of compound 3 to the carboxylic acid using acid or base as described for the conversion of 1 to 2.

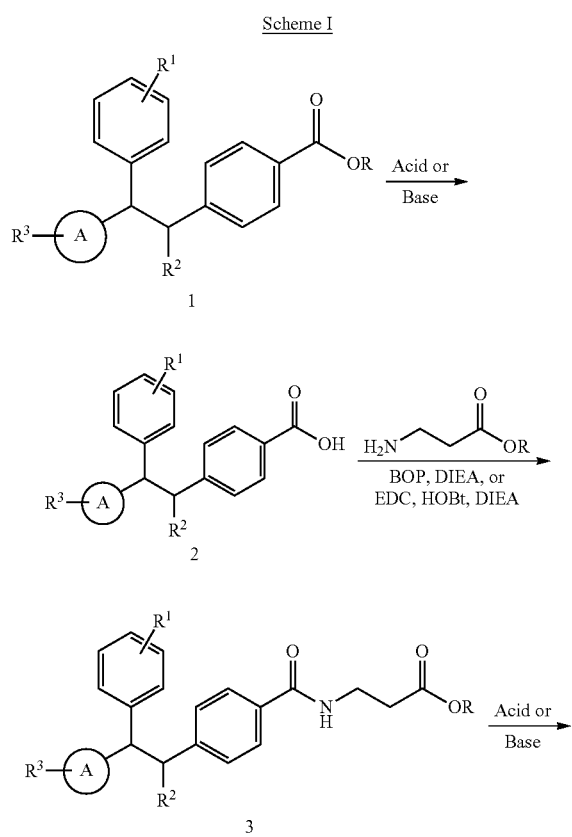

Scheme I

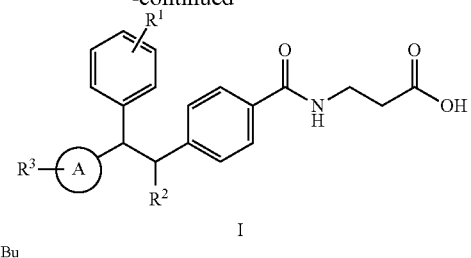

R = Me, Et, or t-Bu

In another embodiment of the invention, when A is a substituted 4-quinazoline, compound I can be synthesized from indole precursors 4 as shown in Scheme 2. The synthesis of precursors 4 is described in WO 2008042223, Preparation of indole β-alanine derivatives as glucagon receptor antagonists, Stelrnach, et. al. Treatment of 4 with ozone gas in dichloromethane solvent at −78° C. followed by the addition of dimethylsulfide can afford a mixture of ketones 5a and 5b, which can then be converted completely to 5b using conditions such as those described for the conversion of intermediate 1 to 2. Compound I can then be accessed from intermediate 5b by heating in a microwave reactor in the presence of formamide and a Lewis acid, such as boron trifluoride, Scheme 2

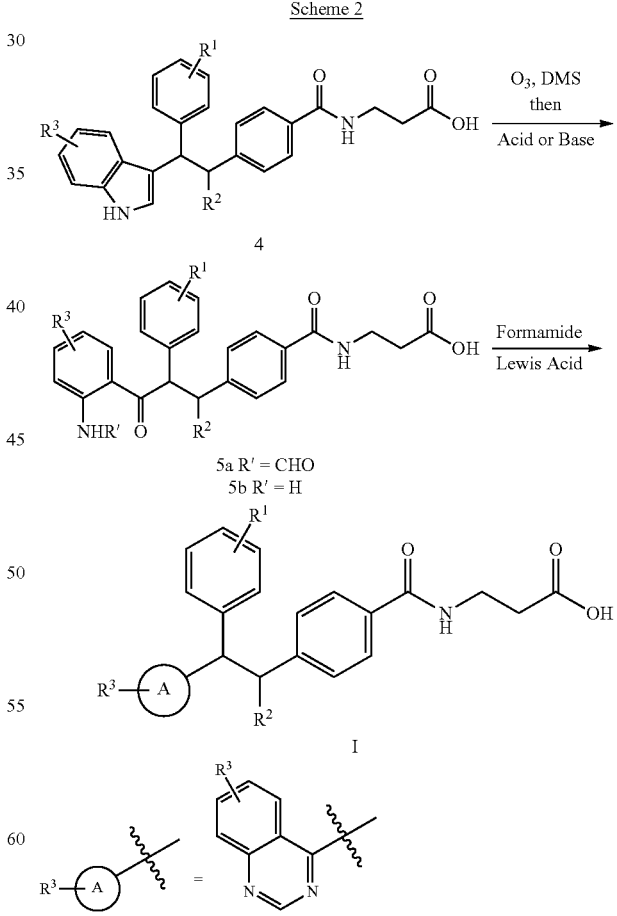

One method for the preparation of intermediate 1 is shown in Scheme 3 proceeding from alcohol 6. The preparation of alcohols such as 6, in both racemic and enantioenriched form, can be performed as described in *Organic Letters*, Chung, et. al., 2008, 10, 3037-3040. Oxidation of alcohol 6 to ketone 7 can be carried out with a variety of oxidants, for instance PCC or Dess-Martin periodinane, in solvents such as dichloromethane. Heteroaryl halides 8 can be metalated with an organometallic reagent, such as nBuLi, in an aprotic solvent such as THF at −78° C. The resulting metalated heteroaromatic intermediate can then add to ketone 7 to afford tertiary alcohol 9. Alcohol 9 may be converted to xanthate 10a by deprotonation with a base such as sodium hydride in an aprotic solvent such as THF followed by treatment with carbon disulfide then iodomethane, all of this occurring at temperatures between 0° C. and ambient temperature. Alternatively, alcohol 9 may be converted to oxalate 10b by deprotonation with a base such as LHMDS in an aprotic solvent such as THF followed by treatment with methyl oxalyl chloride, all of this occurring at temperatures between −78° C. and room temperature. Both xanthate 10a and oxalate 10b may be deoxygenated to afford intermediate 1 by heating to 100° C. in a solvent such as toluene in the presence of a hydride source such as tributyltin hydride using a radical initiator such as AIBN. Alternatively, tertiary alcohol 9 may be converted directly to intermediate 2 by treatment with a hydride source such as triethylsilane with a Lewis acid such as boron trifluoride in a solvent such as dichloromethane at temperatures between −78° C. and ambient temperature.

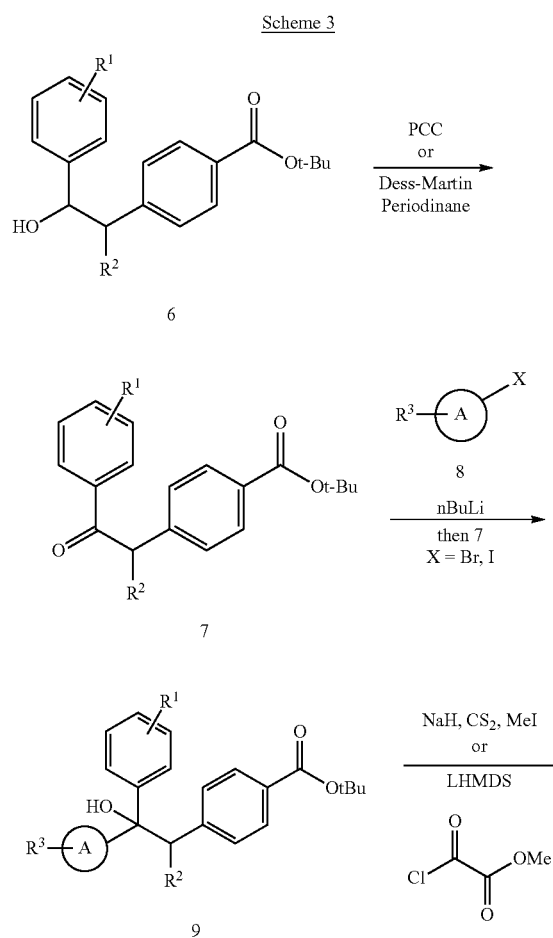

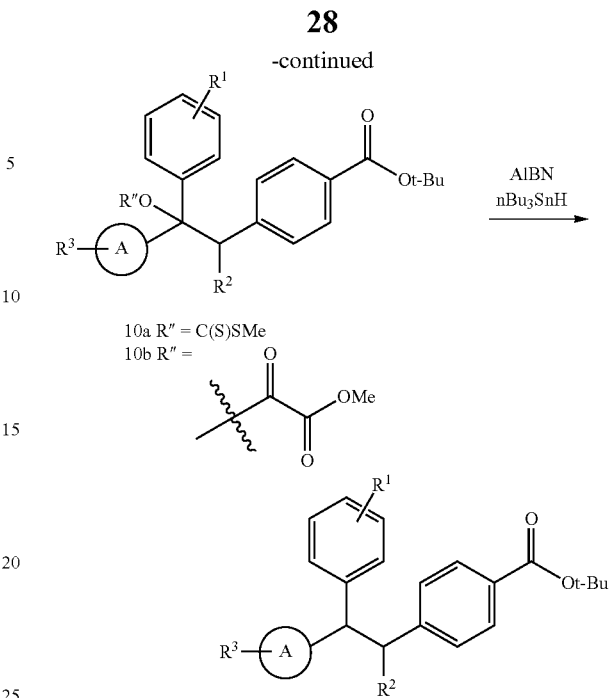

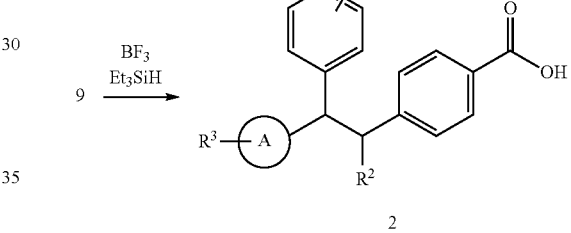

When heteroaromatic halide 8 is certain 4-bromoquinolines, the metalation with nBuLi does not proceed smoothly. In these cases it is possible to prepare intermediate 1 using the procedure shown in Scheme 4. This route utilizes a trimethylsilyl protecting group on the heteroaromatic bromide, as described in *European Journal of Organic Chemistry*, Marull and Schlosser, 2004, 1008-1013. Deprotonation of quinoline 8 with a strong base such as LDA in an aprotic solvent such as THF at −78° C. followed by addition of chlorotrimethylsilane affords the silylated quinoline 11. Quinoline 11 can then be metalated and added to ketone 7 as described above to afford intermediate 12. Intermediate 12 can then be converted to intermediate 13 by acylation and deoxygenation as described above. Finally, removal of the trimethylsilyl protecting group using a fluoride source such as TBAF in a solvent such as dichloromethane can afford intermediate 1.

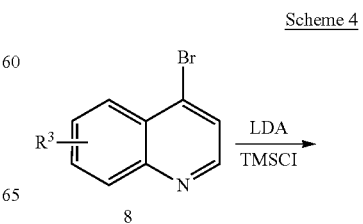

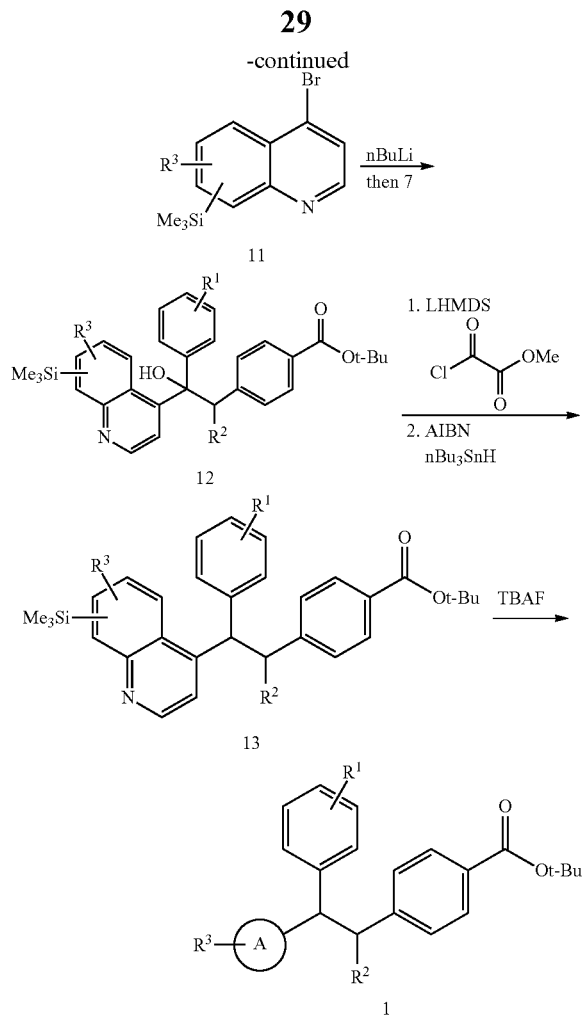

While the $R^3$ substituents are typically present in the starting heteroaryl halides 8 (Scheme 3), it is also possible to alter the $R^3$ substituents on advanced intermediates as shown in Scheme 5. For instance, the 2-chloro substituent of intermediate 3a (which can be prepared according to Scheme 1) can be functionalized under Suzuki coupling conditions with a heteroaryl boronic acid 14, palladium catalyst such as $Pd(PPh_3)_4$, base such as sodium bicarbonate, in a mixed solvent system such as THF and water, at temperatures between 70° C. and 200° C. Under these conditions, the ethyl ester of intermediate 3a can also be hydrolyzed to afford compound I directly. Numerous other metal-mediated functionalizations of intermediates such as 3a will be obvious to those skilled in the art. Another possible functionalization is the demethylation of intermediate 2a with a Lewis acid such as iodotrimethylsilane or boron tribromide in a solvent such as dichloromethane. The resulting intermediate 2b may then be alkylated with, for instance, a difluoromethyl substituent to afford intermediate 2c using sodium chlorodifluoroacetate, a base such as potassium carbonate, in a mixed solvent system of water and a polar organic solvent such as N-methylpyrollidine, at elevated temperatures in a microwave reactor.

Scheme 5

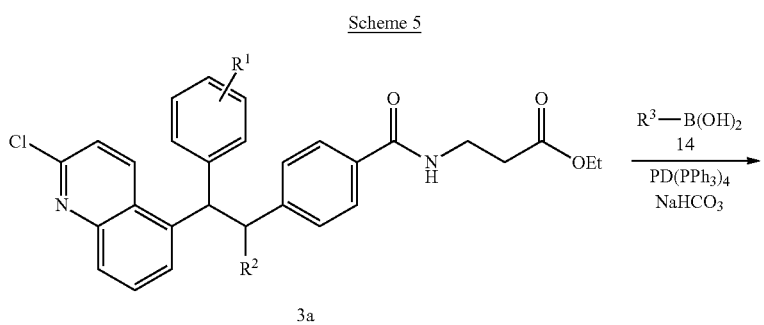

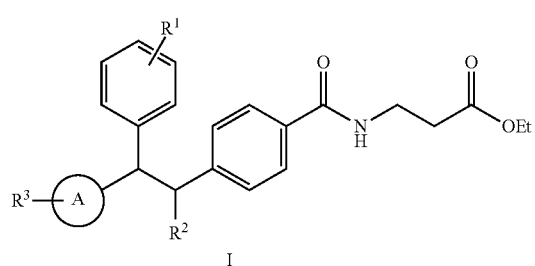

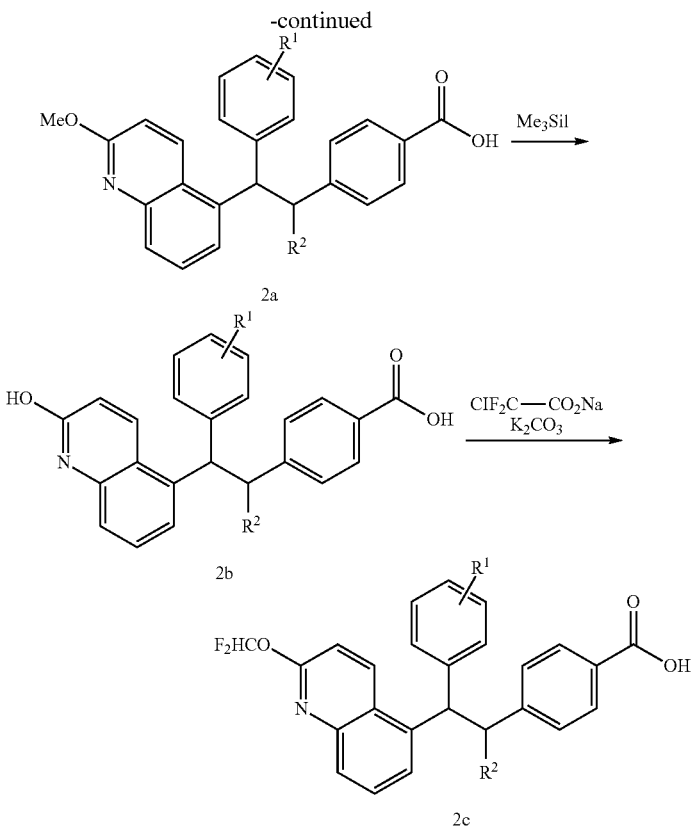

$R^1 = 4\text{-Cl}$
$R^2 = \text{n-Pr}$

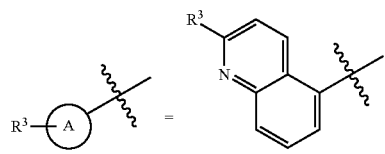

It is also possible to alter the $R^1$ substituents on advanced intermediates as shown in Scheme 6. For instance, the chloro substituent of intermediate 1a may be functionalized using a variety of metal-mediated cross-couplings obvious to those skilled in the art. In certain instances when the chloro substituent may not be reactive enough to serve as a substrate for these reactions, it can be converted to the more reactive bromide using a reagent such as $NiBr_2$ in a polar aprotic solvent like DMF with heating in a microwave reactor as described in Synlett, Arvela and Leadbeater, 2003, 1145-1148. Under these conditions, the ester of 1a is converted to the acid which can be reprotected as the methyl ester using a reagent such as trimethylsilyl diazomethane to afford intermediate 1b. The bromide of intermediate 1b can then be converted to various other substituents under a variety of cross-coupling conditions. For instance, secondary alkyl substituents may be introduced to afford intermediate 1c by heating the appropriately substituted potassium organotrifluoroborate, a palladium catalyst such as $Pd(OAc)_2$, a ligand such as n-butyldi-1-adamantylphosphine, and a base such as cesium carbonate in a mixed solvent system such as toluene and water as described in *Journal of the American Chemical Society*, Dreher, et. al., 2008, 130, 9257-9259.

Scheme 6

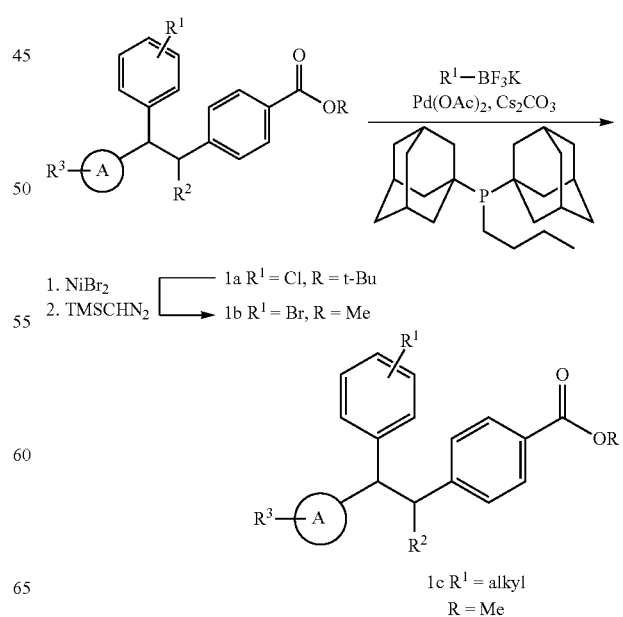

Another preparation of intermediate 1 which may be employed for compounds where the heteroaryl substituent (A) is a 2-quinazoline is presented in Scheme 7. Alkylation of ester 15 with benzyl bromide 16 can be mediated by bases such as LHMDS or KOtBu in polar aprotic solvents such as DMF or DMSO to provide a mixture of diastereomeric intermediates 17. Compounds 15 and 16 may be commercially available, or are readily prepared using methods familiar to those skilled in the art. The t-butyl ester of intermediate 17 can be selectively removed using an acid such as TFA as described for the conversion of intermediate 1 to 2 (Scheme 1). Acid 18 can then be coupled with an aniline to afford N-aryl amide 19 using any of the various known methods for peptide coupling, for instance using the coupling reagent PyBOP and the base DMAP in a solvent such as DMF. Aryl amide 19 can then be converted to 2-quinazoline-substituted intermediate 1 in the presence of trifluoromethanesulfonic anhydride (Tf$_2$O), 2-chloropyridine, and a nitrile in a solvent such as dichloromethane at temperatures from −78° C. to 140° C. as described in *Journal of the American Chemical Society*, Movassaghi and Hill, 2006, 128, 14254-14255.

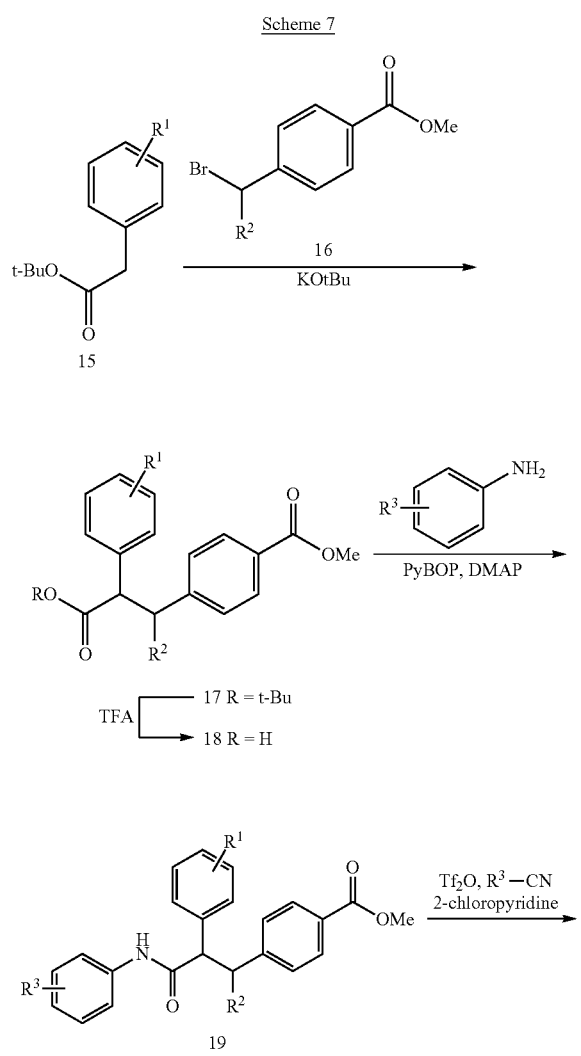

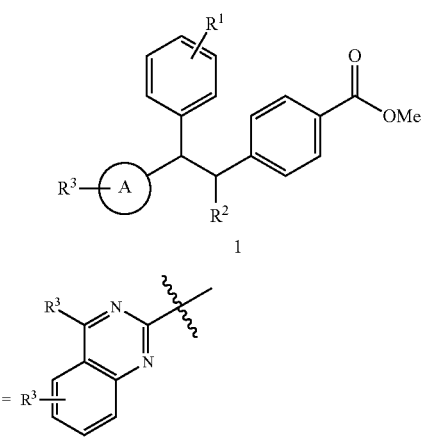

Numerous heteroaryl halides 8 are commercially available, and many more may be prepared using methods familiar to those skilled in the art. Some examples are described in the following references and in Scheme 8. For instance, various haloquinolines may be synthesized from the corresponding haloaniline using the method described in *Journal of Medicinal Chemistry*, Gerson, et. al., 1972, 15, 105-106. Bromination of quinolin-4-ols 20 (accessed from the corresponding aniline according to the procedure in *Bioorganic and Medicinal Chemistry Letters*, Madrid, et. al., 2005, 15, 1015-1018) with various reagents such as phosphorous tribromide or triphenylphosphine dibromide allows for the preparation of 4-bromoquinolines 8. Direct bromination of various heteroaromatic systems 21 may be accomplished with reagents such as bromine and NBS to afford heteroaryl bromides 8. Alternatively, heteroaromatic 21 may be functionalized by nitration with potassium nitrate and sulfuric acid to afford nitro compound 22. Reduction of compound 22 can be achieved with various reductants, such as sodium borohydride and nickel (II) chloride, to afford amine 23. Amine 23 may be converted to the heteroaryl bromide 8 by diazotization with acid and sodium nitrite followed by displacement with cuprous bromide. Heteroaryl halides 8 may also be functionalized at the position adjacent to nitrogen, after conversion to N-oxide 24 with an oxidant such as mCPBA. Compound 24 may be converted to nitrile 8a by heating in the presence of cyanotrimethylsilane. Alternatively, halides 8b may be accessed by treating compound 24 with the appropriate phosphoryl trihalide. Halides 8b may then be further elaborated to compound 8c by heating in the presence of an alkoxide base in an alcoholic or polar aprotic solvent.

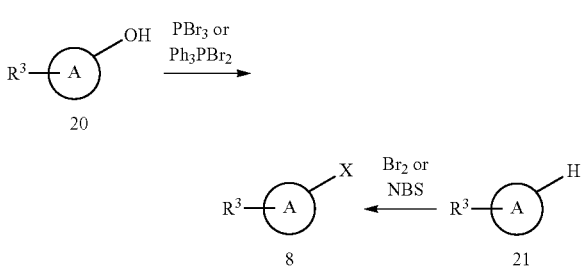

-continued

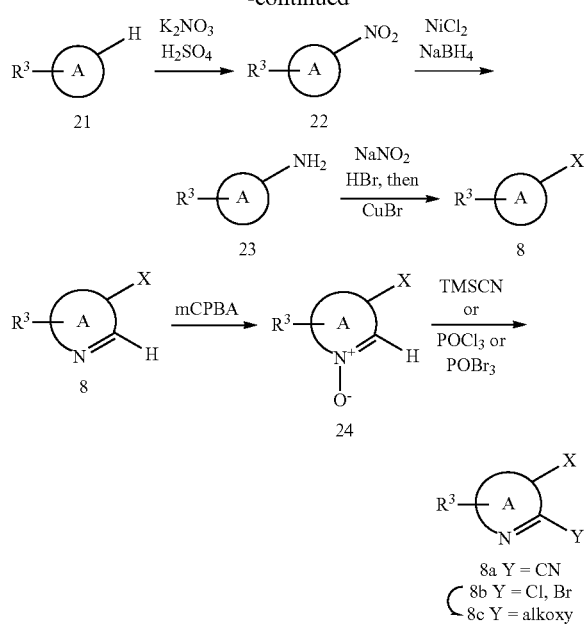

X = Br

Analytical HPLC Mass Spectrometry Conditions

| | |
|---|---|
| LC1: | Column: Waters Xterra MS C-18, 3.5μ, 3.0 × 50 mm |
| | Temperature: 50° C. |
| | Eluent: 10:90 to 98:2 v/v acetonitrile/water + 0.05% TFA over 3.75 min. |
| | Flow Rate: 1.0 mL/min, Injection 10 μL |
| | Detection: PDA, 200-600 nm |
| | MS: mass range 150-750 amu; positive ion electrospray ionization |
| LC2: | Column: Waters Xterra MS C-18, 3.5μ, 2.1 × 20 min |
| | Temperature: 50° C. |
| | Eluent: 5:95 to 98:2 v/v acetonitrile/water + 0.05% TFA over 1.25 min. |
| | Flow Rate: 1.5 mL/min, Injection 5 μL |
| | Detection: PDA, 200-600 nm |
| | MS: mass range 150-750 amu; positive ion electrospray ionization |
| LC3: | Column: Waters Xterra IS C-18, 3.5μ, 2.1 × 20 mm |
| | Temperature: 50° C. |
| | Eluent: 5:95 to 95:5 v/v acetonitrile/water + 0.05% TFA over 3.00 min. |
| | Flow Rate: 1.5 mL/min, Injection 5 μL |
| | Detection: PDA, 200-600 nm |
| | MS: mass range 150-750 amu; positive ion electrospray ionization |
| LC4: | Column: Waters Xterra IS C-18, 3.5μ, 2.1 × 20 mm |
| | Temperature: 50° C. |
| | Eluent: 10:90 to 98:2 v/v acetonitrile/water + 0.1% formic acid over 3.25 min. |
| | Flow Rate: 1.5 mL/min, Injection 5 μL |
| | Detection: PDA, 200-600 nm |
| | MS: mass range 150-750 amu; positive ion electrospray ionization |
| LC5: | Column: Waters Xterra IS C-18, 3.5μ, 2.1 × 20 mm |
| | Temperature: 50° C. |
| | Eluent: 10:90 to 98:2 v/v acetonitrile/water + 0.1% formic acid over 1.25 min. |
| | Flow Rate: 1.5 mL/min, Injection 5 μL |
| | Detection: PDA, 200-600 nm |
| | MS: mass range 150-750 amu; positive ion electrospray ionization |
| LC6: | Column: Waters Sunfire C18, 5μ, 4.6 × 50 mm |
| | Temperature: 50° C. |
| | Eluent: 10:90 to 100:0 v/v acetonitrile/water + 0.1% trifluoroacetic acid over 3.75 min. |
| | Flow Rate: 1.2 mL/min, Injection 10 μL |
| | Detection: PDA, 190-300 nm |
| | MS: mass range 150-700 amu; positive ion electrospray ionization |
| LC7: | Column: Waters Xterra MS C18, 5μ, 3.0 × 50 mm |
| | Temperature: 50° C. |
| | Eluent: 10:90 to 100:0 v/v acetonitrile/water + 0.05% trifluoroacetic acid over 3.75 min. |
| | Flow Rate: 1.0 mL/min, Injection 10 μL |
| | Detection: PDA, 200-600 nm |
| | MS: mass range 150-700 amu; positive ion electrospray ionization |

General chiral semi-preparative conditions: 2 cm×25 cm column chiral column available from Daicel Chemical Industries, LTD, 9 ml/min isocratic EtOH or IPA/heptane eluent.

Preparative reverse phase HPLC(RP-HPLC) conditions:
Column: Atlantis dC18, 5 μm, 19×150 mm
Flow Rate: 20.0 mL/min
Eluent: 10:90 to 100:0 v/v acetonitrile/water+0.1% TFA over 10.0 min.
Temperature: ambient
Detection: FDA, 254 nm Preparative thin layer chromatography (PTLC) was performed on 20×20 cm plates (500 μm thick silica gel). Silica gel chromatography was done on a Biotage Horizon flash chromatography system.

The following examples are provided so that the invention might be more fully understood. They should not be construed as limiting the invention in any way.

Intermediate 1

(R)-4-[2-(4-Chlorophenyl)-1-Propylethan-2-One-1-yl]Benzoic Acid Tert-Butyl Ester

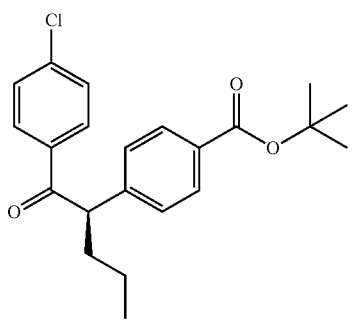 [SMILES: CCC[C@@H](C(=O)c1ccc(Cl)cc1)c1ccc(C(=O)OC(C)(C)C)cc1]

Step A. tert-Butyl 4-[2-(4-Chlorophenyl)-1-propyle-than-2-one-1-yl]benzoate

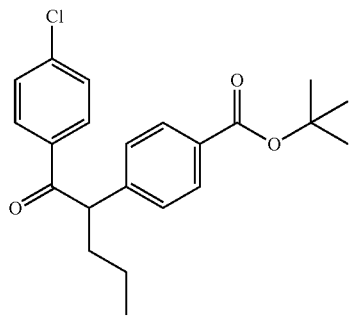 [SMILES: CCCC(C(=O)c1ccc(Cl)cc1)c1ccc(C(=O)OC(C)(C)C)cc1]

A 3-neck flask was charged with NaOtBu (2.85 g, 28.6 mmol) and dry THF (50 mL) under nitrogen. Tris(dibenzylideneacetone)dipalladium(0) (0.26 g, 0.28 mmol) and (S)-Tol-Binap (0.47 g, 0.69 mmol) were then added under nitrogen. After stirring for 15 min, 1-(4-chlorophenyl)pentan-1-one (4.21 g, 21.0 mmol) was added, followed by tert-butyl 4-bromobenzoate (5.0 g, 19.1 mmol) under nitrogen. The mixture was heated at 60° C. for 8 hours. The mixture was diluted with heptane (100 mL) and poured into a solution of saturated NaHCO$_3$ (aq) (60 mL) and ice (40 g). The resulting layers were separated, and the aqueous phase was back-extracted with methyl tert-butyl ether (50 mL). The combined organics were washed with saturated NaHCO$_3$ (aq) then 10% NaCl (aq). The organic solution was filtered through a bed of silica 60 (84 g, wetted with 1:1 methyl tert-butyl ether/heptane), and washed with 1:1 methyl tert-butyl ether/heptane (600 mL). The combined filtrate was concentrated to afford an orange oil that was used directly for the next step: $^1$H NMR (500 MHz, CDCl$_3$): δ 7.91 (d, J=8.1 Hz, 2 H); 7.86 (d, J=8.4 Hz, 2H); 7.35 (d, =8.4 Hz, 2H); 7.32 (d, J=8.2 Hz, 2H); 4.53 (t, J=7.2 Hz, 1H); 2.19-2.09 (m, 1H); 1.85-1.76 (m, 1H); 1.56 (s, 9H); 1.35-1.18 (m, 2H); 0.91 (t, J=7.3 Hz, 3H); LC1: 1.35 min. (M–tBu+H)=317.

Step B. tert-Butyl 4-[(1R,2R)-2-(4-Chlorophenyl)-1-propylethan-2-hydroxyl-1-yl]benzoate

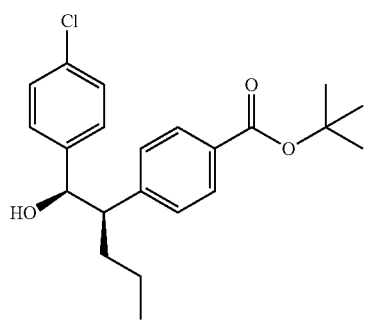 [SMILES: CCC[C@H](c1ccc(C(=O)OC(C)(C)C)cc1)[C@@H](O)c1ccc(Cl)cc1]

To degassed 2-propanol (5.0 mL) was added RuCl$_2$-[(S)-xyl-SEGPHOS][(S)-DAIPEN] (16.2 mg, 0.0134 mmol) and potassium t-butoxide (300 mg, 2.67 mmol). After this mixture was stirred at room temperature for 2 hours, the material obtained in Step A was added in 2-propanol (25 mL). This mixture was then treated with hydrogen (100 psi) at room temperature for 18 hours. The mixture was concentrated, then the residue was recrystallized from 2-propanol/water to afford the desired product: $^1$H NMR (400 MHz, CDCl$_3$) δ 7.96 (m, 2H), 7.32 (m, 2H), 7.26 (m, 2H), 7.22 (m, 2H), 4.76 (dd, J=7.7, 2.9 Hz, 1H), 2.89 (ddd, J=11.5, 7.7, 4.2 Hz, 1H), 1.84 (d, J=2.9 Hz, 1H), 1.62 (s, 9H), 1.61 (m, 1H), 1.41 (m, 1H), 1.05 (m, 2H), 0.76 (t, J=7.3 Hz, 3H); LC3: 2.38 min. (M–H$_2$O-tBu+H)=301; Chiral SFC Method: Chiralpak AD-H (250×4.6 mm), isocratic 15% MeOH/CO$_2$, 1.5 mL/min, 200 bar, 35° C., 215 nm, 15 minutes: desired alcohol RT=9.8 min; enantiomeric alcohol; RT=10.6 min; diastereomeric alcohols: RT=5.2 and 6.3 min.

Step C. tert-Butyl (R)-4-[2-(4-Chlorophenyl)-1-propylethan-2-one-1-yl]benzoate

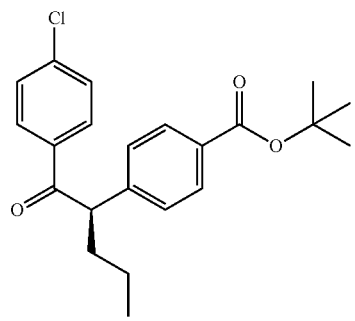 [SMILES: CCC[C@@H](C(=O)c1ccc(Cl)cc1)c1ccc(C(=O)OC(C)(C)C)cc1]

Pyridinium chlorochromate (4.9 g, 23 mmol) was added to a solution of the product from Step B (7.1 g, 19 mmol) in CH$_2$Cl$_2$ (200 mL), and the mixture was stirred at room temperature until reaction was complete as monitored by LC/MS. The mixture was diluted with 200 mL of Et$_2$O, filtered, and washed with Et$_2$O. The combined filtrate and washings were concentrated, then purified by silica gel chromatography with 0-5% EtOAc/hexanes to afford the title compound as a colorless oil which solidified upon standing: $^1$H NMR (500 MHz, CDCl$_3$): δ 7.91 (d, J=8.1 Hz, 2H); 7.86 (d, J=8.4 Hz, 2H); 7.35 (d, J=8.4 Hz, 2H); 7.32 (d, J=8.2 Hz, 2H); 4.53 (t, J=7.2 Hz, 1H); 2.19-2.09 (m, 1H); 1.85-1.76 (m, 1H); 1.56 (s, 9H); 1.35-1.18 (m, 2H); 0.91 (t, J=7.3 Hz, 3H); LC1: 1.35 min. (M-tBu+H) 317.

Intermediate 2

4-Bromo-6-Chloro-8-Methylquinoline

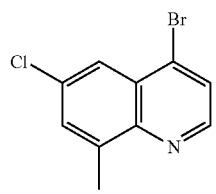

Intermediate 2 can be obtained from commercially available sources or produced in accordance with the example below.

Step A. 6-Chloro-8-methylquinolin-4-ol

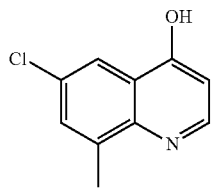

A solution of 2,2-dimethyl-1,3-dioxane-4,6-dione (1.58 g, 11.0 mmol) in trimethyl orthoformate (10 mL, 90 mmol) was refluxed for one hour. The mixture was cooled slightly, then a solution of 4-chloro-6-methylaniline (1.4 g, 10 mmol) in DMF (10 mL) was added. The mixture was refluxed for 2 hours then cooled to room temperature. The mixture was poured into cold water (150 mL) then extracted with EtOAc. The organic phase was washed with water then saturated NaCl (aq), dried over $Na_2SO_4$, filtered, then concentrated. The resulting light yellow, crystalline solid was used directly for the following step. LC4: 2.14 min. (M+H) 296.

The solid from the previous step was dissolved in diphenyl ether (10 mL) and heated to reflux for 30 minutes. The mixture was allowed to cool to room temperature then poured into hexanes. The resulting solid was collected by filtration and washed with hexanes. The material was dried in vacuo and used in the next step without purification. LC4: 2.34 min. (M+H) 194.

Step B. 4-Bromo-6-chloro-8-methylquinoline

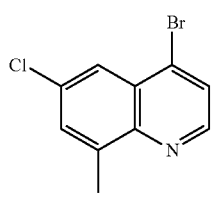

A mixture of 6-chloro-4-hydroxy-8-methylquinoline (1.9 g, 9.8 mmol) and triphenylphosphine dibromide (6.2 g, 14.7 mmol) in acetonitrile (50 mL) was refluxed for 2 hours. The mixture was allowed to cool to room temperature then concentrated. The residue was purified by silica gel chromatography eluting with 0-10% EtOAc/hexanes to afford the title compound as a white solid: $^1$H NMR (500 MHz, CDCl$_3$): δ 8.67 (d, J=4.7 Hz, 1H); 8.06 (d, J=2.2 Hz, 1H); 7.71 (d, J=4.6 Hz, 1H); 7.58 (s, 1H); 2.79 (s, 3H); LC1: 1.88 min. (M+H) 256.

Intermediate 3

5-Bromo-2-Methoxyquinoline

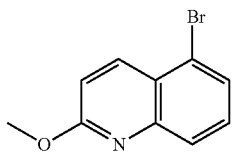

To a suspension of 5-bromo-2-chloroquinoline (2.81 g, 11.6 mmol) in MeOH (25 mL) was added sodium methoxide (30% w/w in MeOH, 10.4 mL, 54.7 mmol). The mixture was refluxed for 3 hours, allowed to cool to room temperature, diluted with water, then extracted with EtOAc. The combined extracts were washed with water then saturated NaCl (aq), dried over $Na_2SO_4$, filtered, then concentrated to afford the title compound as a white solid: $^1$H NMR (500 MHz, CDCl$_3$): δ 8.36 (d, J=9.1 Hz, 1H); 7.81 (d, J=8.4 Hz, 1H); 7.63 (dd, J=7.6, 1.1 Hz, 1H); 7.46 (t, 1H, J=7.9 Hz); 6.98 (d, J=9.1 Hz, 1H); 4.08 (s, 3H); LC1 1.85 min. (M+H) 238.

Intermediate 4

5-Bromo-8-Fluoro-2-Methoxyquinoline

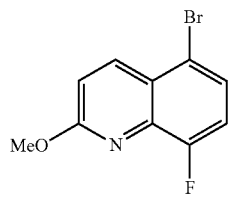 [SMILES: COc1ccc2c(Br)ccc(F)c2n1]

Step A. 5-Bromo-8-fluoroquinoline

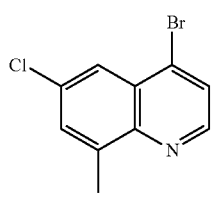

5-Bromo-2-fluoroaniline (1.0 g, 5.3 mmol) was mixed with glycerol (2.0 mL, 27 mmol), sodium 3-nitrobenzene sulfonate (1.2 g, 5.3 mmol) and concentrated sulfuric acid (8 mL), then the mixture was heated to 140° C. for 2 hours. The inital suspension became a dark brown solution. The mixture was allowed to cool to room temperature. The solution was made basic with 5N NaOH (30 mL), then extracted with EtOAc. The combined organic phase was washed with water then saturated NaCl (aq), dried over MgSO$_4$, filtered, then concentrated to afford the title compound as a white solid. $^1$H NMR (500 MHz, CDCl$_3$): δ 9.00 (d, J=4.2 Hz, H); 8.54 (d, J=8.6 Hz, 1H); 7.77 (dd, J=8.3, 4.5 Hz, 1H); 7.59 (dd, J=8.6, 4.2 Hz, 1H); 7.32 (dd, J=9.9, 8.3 Hz, 1H). LC4 1.81 min. (M+H)=226.

Step B. 5-Bromo-2-chloro-8-fluoroquinoline

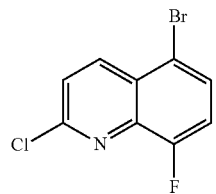 [SMILES: Fc1ccc(Br)c2ccc(Cl)nc12]

3-Chloroperoxybenzoic acid (8.72 g, 35.4 mmol) was added to 5-brorno-8-fluoroquinoline (4.0 g, 18 mmol) in CH$_2$Cl$_2$ (50 mL) at room temperature. After stirring for 16 hours, the solution was diluted with CH$_2$Cl$_2$ (200 mL) and washed with 4 M NaOH (aq) (100 mL), then saturated NaCl (aq) (100 mL). The organic layer was dried over Na$_2$SO$_4$, filtered, then concentrated. The residue was purified by silica gel chromatography eluting with 0-100% EtOAc/hexanes to afford the N-oxide as a white solid. $^1$H NMR (600 MHz, CDCl$_3$): δ 8.45 (d, J=6.1 Hz, 1H); 7.98 (d, J=8.8 Hz, 1H); 7.78 (dd, J=8.5, 3.8 Hz, 1H); 7.36 (dd, J=8.8, 6.1 Hz, 1H); 7.21 (dd, J=12.5, 8.4 Hz, 1H); LC4: 1.25 min. (M+H) 244.

A solution of the N-oxide from the previous step (1.0 g, 4.1 mmol) and POCl$_3$ (1.2 mL, 12 mmol) in CHCl$_3$ (10 mL) was refluxed for one hour, then allowed to cool to room temperature. The solution was washed with saturated NaHCO$_3$ (aq), dried over MgSO$_4$, filtered, then concentrated to afford the title compound as an off-white solid. $^1$H NMR (500 MHz, CDCl$_3$): δ 8.51 (d, J=8.9 Hz, 1H); 7.81 (dd, J=8.4, 4.4 Hz, 1H); 7.59 (d, J=8.9 Hz, 1H); 7.38 (t, J=9.0 Hz, 1H). LC1 1.67 min. (M+H)=260.

Step C. 5-Bromo-8-fluoro-2-methoxyquinoline

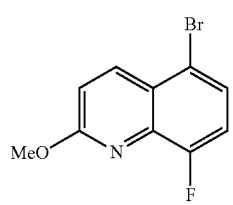 [SMILES: COc1ccc2c(Br)ccc(F)c2n1]

To a suspension of 5-bromo-2-chloro-8-fluoroquinoline (1.08 g, 4.2 mmol) in anhydrous methanol (10 mL) at 50° C. was added NaOMe (30% w/w, 0.9 g, 5.0 mmol). The resulting mixture was stirred at 50° C. for one hour, then allowed to cool to room temperature. The mixture was diluted with water, then extracted with EtOAc. The combined organics were washed with water then saturated Nael (aq), dried over MgSO$_4$, filtered, then concentrated. The residue was purified by silica gel chromatography eluting with 0-5% EtOAc/hexanes to afford the title compound as a white solid: $^1$H NMR (500 MHz, CDCl$_3$): δ 8.33 (dd, J=9.1, 1.6 Hz, 1H); 7.55 (dd, J=8.4, 4.4 Hz, 1H); 7.22 (dd, J=10.2, 8.4 Hz, 1H); 7.04 (d, J=9.2 Hz, 1H); 4.13 (s, 4H). LC4 2.37 min. (M+H) 256.

Intermediate 5

6-Bromo-8-Fluoro-2-Methoxyquinoline

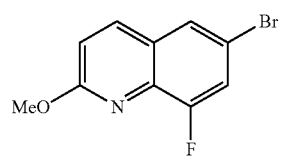 [SMILES: COc1ccc2cc(Br)cc(F)c2n1]

Step A. 6-Bromo-8-fluoroquinolone

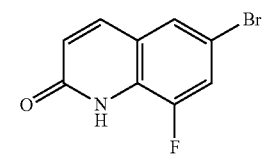 [SMILES: O=c1ccc2cc(Br)cc(F)c2[nH]1]

To a solution of 4-bromo-2-fluoroaniline (12.8 g, 67.6 mmol) and pyridine (13.1 mL, 162 mmol) in CH$_2$Cl$_2$ (50 mL) at 0° C. was added 3-ethoxyacryloyl chloride (10.0 g, 74.3 mmol) dropwise over 30 minutes. The mixture was then stirred at room temperature for 15 minutes. The precipitate was collected by filtration, washed with water, dried in vacuo, then used in the next step without purification. LC6: 3.16 min. (M+H) 288.

The product from the previous step was added slowly to concentrated H$_2$SO$_4$ (50 mL) at 0° C., then the mixture was stirred at room temperature for 18 hours. The mixture was poured onto crushed ice (300 mL) and stirred for 30 min. The precipitate was collected by filtration, washed with water, then dried in vacuo, then used in the next step without purification. LC6: 2.44 min. (M+H) 242.

Step B. 6-Bromo-2-chloro-8-fluoroquinoline

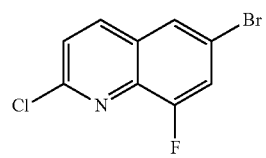 [SMILES: Fc1cc(Br)cc2ccc(Cl)nc12]

Using the POCl$_3$ procedure from INTERMEDIATE 4 Step B, 6-bromo-8-fluoroquinolone was converted to the title compound: LC6: 3.42 min. (M+H) 260.

Step C. 6-Bromo-8-fluoro-2-methoxyquinoline

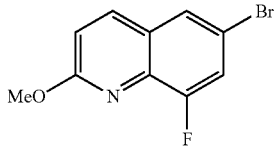

Using the procedure from INTERMEDIATE 3, 6-bromo-2-chloro-8-fluoroquinolone was converted to the title compound: $^1$H NMR (500 MHz, CDCl$_3$): δ 7.92 (dd, J=9.0, 1.0 Hz, 1H); 7.68 (s, 1H); 7.49 (dd, J=10.0, 2.0 Hz, 1H); 6.99 (d, J=9.0 Hz, 1H); 4.12 (s, 3H); LC6: (M+H) 256.

Intermediate 6

4-Bromo-7-Chloro-2-Methoxyquinoline

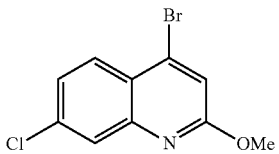 [SMILES: COc1cc(Br)c2ccc(Cl)cc2n1]

Step A. 4-Bromo-7-chloroquinoline

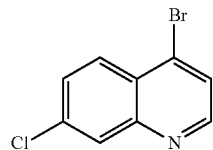 [SMILES: Clc1ccc2c(Br)ccnc2c1]

A suspension of 7-chloroquinolin-4-ol (10.0 g, 55.7 mmol) and triphenylphosphine dibromide (35.3 g, 83.6 mmol) in CH$_3$CN (370 mL) was refluxed for 16 hours then cooled to room temperature. The resulting precipitate was collected by vacuum filtration and washed with CH$_3$CN (2×70 mL). The precipitate was then partitioned between CH$_2$Cl$_2$ (300 mL) and 1 M NaOH (aq) (300 mL). The aqueous phase was extracted with CH$_2$Cl$_2$ (100 mL). The combined organics were dried over Na$_2$SO$_4$, filtered, and concentrated to afford the title compound as a white solid: $^1$H NMR (500 MHz, CDCl$_3$): δ 8.67 (d, J=4.7 Hz, 1H); 8.14 (d, J=9.0 Hz, 1H); 8.11 (d, J=2.1 Hz, 1H); 7.70 (d, J=4.7 Hz, 1H); 7.60 (dd, J=9.0, 2.1 Hz, 1H); LC4 1.86 min. (M+H)=244.

Step B. 2,4-Dibromo-7-chloroquinoline

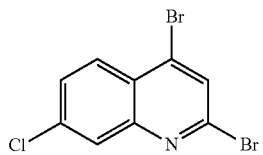 [SMILES: Clc1ccc2c(Br)cc(Br)nc2c1]

3-Chloroperoxybenzoic acid (2.68 g, 15.5 mmol) was added to 4-bromo-7-chloroquinoline (1.88 g, 7.75 mmol) in CH$_2$Cl$_2$ (80 mL) at room temperature. After stirring for 16 hours, the solution was diluted with CH$_2$Cl$_2$ (200 mL) and washed with 4 M NaOH (aq) (100 mL), then saturated NaCl (aq) (100 mL). The organic layer was dried over Na$_2$SO$_4$, filtered, and concentrated. The resulting solid was used directly for the following step. LC5 1.00 min. (M+H)=260.

A solution of the solid from the previous step and POBr$_3$ (5.0 g, 17 mmol) in CHCl$_3$ (75 mL) was heated at 50° C. for 6 hours, then cooled to room temperature. The solution was washed with 4 M NaOH (aq) (2×75 mL), dried over Na$_2$SO$_4$, filtered, and concentrated to afford the title compound as an off-white solid: $^1$H NMR (500 MHz, CDCl$_3$): δ 8.09 (d, J=8.9 Hz, 1H); 8.03 (d, J=2.1 Hz, 1H); 7.83 (s, 1H); 7.61 (dd, J=8.9, 2.1 Hz, 1H); LC4 2.33 min. (M+H)=322.

Step C. 4-Bromo-7-chloro-2-methoxyquinoline

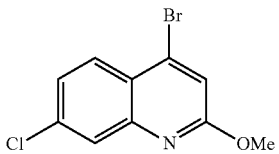 [SMILES: COc1cc(Br)c2ccc(Cl)cc2n1]

Sodium methoxide (0.5 M in MeOH, 2.0 mL, 1.0 mmol) was added to a solution of 2,4-dibromo-7-chloroquinoline (341 mg, 1.06 mmol) in MeOH (7 mL). The mixture was refluxed for one hour then cooled to room temperature. The resulting precipitate was collected by filtration to afford the title compound as an off-white solid: $^1$H NMR (500 MHz, CDCl$_3$): δ 8.00 (d, J=8.8 Hz, 1H); 7.85 (d, J=2.1 Hz, 1H); 7.40 (dd, J=8.8, 2.1 Hz, 1H); 7.22 (s, 1H); 4.04 (s, 3H); LC4 2.45 min. (M+H)=274.

The regiochemistry of methoxide addition was confirmed by observation of a nuclear Overhauser effect to the C3 and C8 protons upon irradiation of the methoxy group.

Intermediate 7

5-Bromo-7-Chloroquinoline

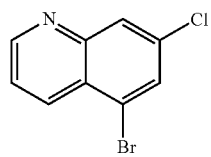 [SMILES: Clc1cc(Br)c2cccnc2c1]

Step A. 8-Amino-5-bromoquinoline

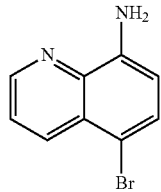 [SMILES: Nc1ccc(Br)c2cccnc12]

To a solution of 8-aminoquinoline (4.0 g, 28 mmol) in CH₃CN (185 mL) was added N-bromosuccinimide (2.47 g, 13.9 mmol). After stirring for 15 minutes, a second portion of N-bromosuccinimide (2.71 g, 15.2 mmol) was added. After stirring for an additional 30 minutes, the mixture was concentrated. The residue was dissolved in EtOAc, then washed with water (2×100 mL) and saturated NaCl (aq) (100 mL). The organics were dried over Na₂SO₄, filtered, then concentrated. The residue was purified by silica gel chromatography eluting with 10-15% EtOAc/hexanes to afford the title compound as a white solid: $^1$H NMR (500 MHz, CDCl₃): δ 8.79 (dd, J=1.5, 4.1 Hz, 1H), 8.46 (dd, J=1.5, 8.5 Hz, 1H), 7.60 (d, J=8.1 Hz, 1H), 7.52 (dd, J=4.1, 8.5 Hz, 1H), 6.83 (d, J=8.1 Hz, 1H); LC7: 2.48 min. (M+H) 225.

Step B. 8-Amino-5-bromo-7-chloroquinoline

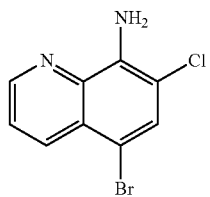 [SMILES: Nc1c(Cl)cc(Br)c2cccnc12]

To a solution of 8-amino-5-bromoquinoline (440 mg, 1.97 mmol) in CH₃CN (39 mL) was added N-chlorosuccinimide (250 mg, 1.87 mmol). The mixture was stirred at 75° C. until no further conversion of the starting material was observed by LC/MS and TLC analysis. The mixture was allowed to cool to room temperature then concentrated. The residue was dissolved in EtOAc, then washed with water (2×50 mL) then saturated NaCl (aq) (50 mL). The organic phase was dried over Na₂SO₄, filtered, then concentrated. The residue was purified by silica gel chromatography eluting with 15% EtOAc/hexanes to afford the title compound as a solid: $^1$H NMR (500 MHz, CDCl₃): δ 8.81 (dd, J=1.4, 4.1 Hz, 1H) 8.43 (dd, J=1.4, 8.5 Hz, 1H), 7.71 (s, 1H), 7.51 (dd, J=4.1, 8.5 Hz, 1H); LC6: 4.27 min. (M+H) 259.

Step C. 5-Bromo-7-chloroquinoline

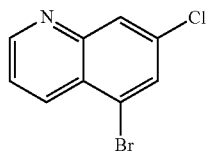 [SMILES: Clc1cc(Br)c2cccnc2c1]

To a suspension of 8-amino-5-bromo-7-chloroquinoline (700 mg, 2.72 mmol) in water (27 mL) at 0° C. was added concentrated sulfuric acid until the solid was mostly dissolved and the solution was a bright yellow. A solution of NaNO₂ (375 mg, 5.44 mmol) in water (7 mL) was added dropwise to the stirring quinoline solution. After stirring at 0° C. for an additional 15 minutes, the cold solution was slowly added to stirring H₃PO₂ (6.5 mL, 54 mmol) at 65° C. Following complete addition of the cold solution, the mixture continued to be stirred at 65° C., and additional H₃PO₂ was added until the solution became colorless and no additional product formation was observed by LC/MS. Upon completion, the mixture was allowed to cool to room temperature, neutralized with 1M NaOH (aq), then extracted twice with EtOAc. The combined organics were washed with water (2×50 mL) then saturated NaCl (aq) (50 mL). The organics were dried over Na₂SO₄, filtered, then concentrated. The residue was purified by silica gel chromatography eluting with 0-5% EtOAc/hexanes to afford the title compound as a white solid: $^1$H NMR (500 MHz, CDCl₃): δ 8.95 (dd, J=1.4, 4.1 Hz, 1H), 8.50 (d, J=8.5 Hz, 1H), 8.10 (d, =0.9 Hz, 1H), 7.83 (d, J=1.8 Hz, 1H), 7.52 (dd, J=4.1, 8.5 Hz, 1H); LC6: 3.90 min. (M+H) 244.

Intermediate 8

5-Bromo-2-Chloro-3-Methylquinoline

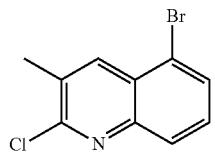

To a solution of 5-bromo-2-chloroquinoline (1.0 g, 4.1 mmol) in anhydrous THF (20 mL) at −78° C. was added LDA (2.0 M in heptane/THF/ethylbenzene, 3.1 mL, 6.2 mmol) dropwise. After stirring for one hour, iodomethane (1.28 mL, 20.6 mmol) was added, and the mixture was stirred at −78° C. for another hour. The mixture was poured into saturated NH₄Cl (aq) then extracted twice with EtOAc. The organic extracts were concentrated and the residue was purified by reverse-phase HPLC to afford the title compound: $^1$H NMR (500 MHz, CDCl₃): δ 8.34 (s, 1H); 7.96 (d, J=8.3 Hz, 1H); 7.80 (d, J=7.5 Hz, 1H); 7.53 (d, J=7.8 Hz, 1H); 2.60 (s, 3H) LC3: 1.41 min. (M+H) 258.

Intermediate 9

5-Bromoquinoline-2-Carbonitrile

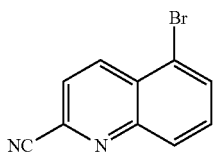 [SMILES: N#Cc1ccc2c(Br)cccc2n1]

To a solution of 5-bromoquinoline (1.67 g, 8.03 mmol) in anhydrous CH₂Cl₂ (40 mL) was added 3-chloroperoxybenzoic acid (5.54 g, 32.1 mmol). The mixture was stirred at room temperature overnight, then potassium carbonate (4.79 g, 34.7 mmol) was added and the mixture was stirred for 30 minutes. The resulting precipitate was removed by filtration, and the filtrate was concentrated. The resulting material was used in the next step without purification: LC3: 2.73 min. (M+H) 224.

The product of the previous step (500 mg, 2.23 mmol) was mixed with triethylamine (0.93 mL, 6.7 mmol) and trimethylsilyl cyanide (1.19 mL, 8.93 mmol) in anhydrous CH₃CN (7 mL) in a sealed tube. The mixture was stirred at 100° C. overnight, then allowed to cool to room temperature. The mixture was diluted with saturated NaHCO₃ (aq), then extracted with EtOAc. The organics were dried over Na₂SO₄, filtered, then concentrated. The residue was purified by silica gel chromatography eluting with 0-100% EtOAc/hexanes to afford the title compound: ¹H NMR (500 MHz, CDCl₃): δ 8.72 (d, J=8.6 Hz, 1H); 8.17 (d, J=8.3 Hz, 1H); 7.99 (d, J=7.5 Hz, 1H); 7.81 (d, 0.1=8.5 Hz, 1H); 7.71 (t, J=7.8 Hz, 1H) LC3: 2.73 min, (M+H) 233.

Intermediate 10

4-Bromo-8-Chloroisoquinoline

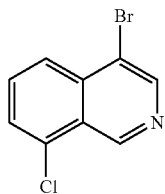 [SMILES: Clc1cccc2c(Br)cncc12]

To a solution of 8-chloroisoquinoline (1.0 g, 6.1 mmol) in nitrobenzene (20 mL) at 180° C. was added bromine (0.35 mL, 6.7 mmol) over 10 min. Heating and stirring were continued for 2 hours. The mixture was allowed to cool to about 80° C., then 2M HCl in Et₂O (5 mL) was added, followed by Et₂O (5 mL) and hexanes (60 mL). The resulting slurry was filtered, washed with hexane and dried. The collected solid was dissolved in water, then the solution was adjusted to pH 9 with Na₂CO₃ (aq). The solution was extracted with EtOAc. The organic layer was dried over Na₂SO₄, filtered, and concentrated. The residue was purified by silica gel chromatography eluting with 0-20% EtOAc/hexanes to afford the title compound as a white solid: ¹H NMR (500 MHz, CDCl₃): δ 9.62 (s, 1H); 8.83 (s, 1H); 8.13 (t, J=5.0 Hz, 1H); 7.74 (d, J=5.0 Hz, 2H). LC6: 4.08 min, (M+H): 242.

Intermediate 11

5-BromO-1,3-Dimethoxyisoquinoline

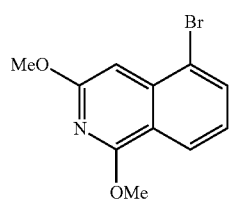 [SMILES: COc1cc2c(Br)cccc2c(OC)n1]

Step A. 5-Bromo-1,3-dichloroisoquinoline

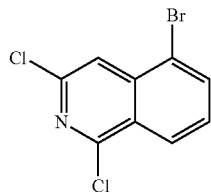 [SMILES: Clc1cc2c(Br)cccc2c(Cl)n1]

To a solution of 1,3-dichloroisoquinoline (1.0 g, 5.1 mmol) in CH₃CN (25 mL) was added concentrated sulfuric acid (1.0 mL, 18 mmol), followed by N-bromosuccinimide (1.1 g, 6.1 mmol). The mixture was stirred at room temperature for 60 hours. The precipitate was collected by filtration, washed with water, then dried in air to afford the title compound: ¹H NMR (500 MHz, CDCl₃): δ 8.35 (d, J=9.0 Hz, 1H), 8.09 (s, 1H), 8.08 (d, J=9.0 Hz, 1H), 7.57 (t, J=8.0 Hz, 1H). LC6: 3.74 min. (M+H): 278.

Step B. 5-Bromo-3-chloro-1-methoxyisoquinoline

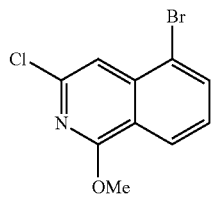 [SMILES: COc1nc(Cl)cc2c(Br)cccc12]

A mixture of 5-bromo-1,3-dichloroisoquinoline (580 mg, 2.1 mmol) and NaOMe (0.5 M in MeOH, 5.0 mL, 2.5 mmol) was heated at 70° C. for one hour. The mixture was poured into water then extracted with EtOAc. The organic layer was dried over Na₂SO₄, filtered, then concentrated to afford the title compound: ¹H NMR (500 MHz, CDCl₃): δ 8.23 (d, J=9.0 Hz, 1H), 7.96 (d, J=7.5 Hz, 1H); 7.65 (s, 1H), 7.39 (t, J=8.5 Hz, 1H), 4.20 (s, 3H). LC6: 3.86 min. (M+H) 272.

Step C. 5-Bromo-1,3-dimethoxyisoquinoline

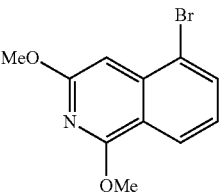

To a solution of 5-bromo-3-chloro-1-methoxyisoquinoline (420 mg, 1.54 mmol) in DMSO (4.0 mL) was added NaOMe (0.5 M in MeOH, 4.0 mL, 2.0 mmol). The solution was heated at 90° C. for 1.5 hours in a microwave reactor. The mixture was poured into water then extracted with EtOAc. The organics were dried over Na₂SO₄, filtered, and concentrated. The residue was purified by silica gel chromatography eluting with 15% EtOAc/hexanes to afford the title compound: ¹H NMR (500 MHz, CDCl₃): δ 8.15 (d, J=8.5 Hz, 1H), 7.87 (d, J=8.0 Hz, 1H); 7.18 (t, J=8.0 Hz, 1H), 6.85 (s, 11-1), 4.18 (s, 3H), 4.05 (s, 3H). LC6: 3.67 min, (M+H): 268.

Intermediate 12

5-Bromo-3-Methoxy-1-Methylisoquinoline

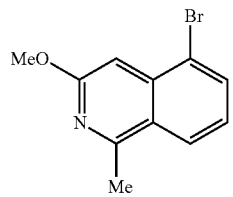 [SMILES: COc1cc2c(Br)cccc2c(C)n1]

Step A. 3-Chloro-1-methylisoquinoline

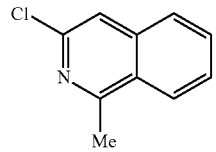 [SMILES: Cc1nc(Cl)cc2ccccc12]

A mixture of 1,3-dichloroisoquinoline (2.0 g, 10.1 mmol), trimethylaluminum (2.0 M in heptane, 6.1 mL, 12.1 mmol), and tetrakis(triphenylphosphine)palladium(0) (117 mg, 0.1 mmol) in THF (8 mL) was heated in a microwave reactor at 100° C. for 15 min. After quenching by addition of water (30 mL), the mixture was extracted with EtOAc. The organics were dried over Na$_2$SO$_4$, filtered, and concentrated. The residue was purified by silica gel chromatography eluting with 10% EtOAc/hexanes to afford the title compound: $^1$H NMR (500 MHz, CDCl$_3$): δ 8.12 (dd, J=8.5, 0.5 Hz, 1H); 7.76 (d, J=8.0 Hz, 1H); 7.10 (dt, J=8.5, 0.5 Hz, 1H), 7.62-7.60 (m, 2H); 2.97 (s, 3H). LC6: 2.85 min, (M+H): 178.

Step B. 3-Chloro-1-methyl-5-nitroisoquinoline

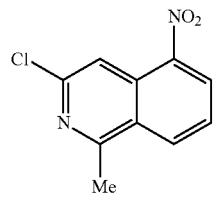 [SMILES: Cc1nc(Cl)cc2c([N+](=O)[O-])cccc12]

To concentrated H$_2$SO$_4$ (10 mL) at 0° C. was slowly added 1-methyl-3-ehloroisoquinoline (1.6 g, 9.0 mmol), followed by K$_2$NO$_3$ (1.1 g, 11 mmol). The mixture was stirred at 0° C. for one hour then allowed to warm to room temperature. The mixture was poured onto crushed ice (100 mL) and NH$_4$OH (aq) was slowly added until the solution reached pH 9. The resulting precipitate was collected by vacuum filtration to afford the title compound as a yellow solid: $^1$H NMR (500 MHz, CDCl$_3$): δ 8.57 (d, J=7.5 Hz, 1H); 8.51 (d, J=8.5 Hz, 1H); 8.48 (s, 1H); 7.74 (t, J=8.5 Hz, 1H), 3.08 (s, 3H). LC6: 2.93 min, (M+H): 223.

Step C. 5-Amino-3-chloro-1-methylisoquinoline

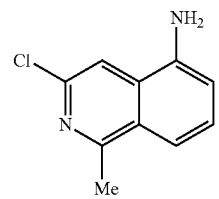 [SMILES: Cc1nc(Cl)cc2c(N)cccc12]

To a solution of 3-chloro-1-methyl-5-nitroisoquinoline (2.0 g, 9.0 mmol) in dioxane (48 mL) and MeOH (10 mL) was added nickel (11) chloride hydrate (66 mg, 0.4 mmol), followed by sodium borohydride (0.7 g, 18 mmol). After stirring for two hours, the mixture was quenched by the addition of water (30 mL). The mixture was extracted with EtOAc, then the combined organics were washed with 10% NH$_4$OH (aq) then saturated NaCl (aq). The organics were dried over Na$_2$SO$_4$, filtered, and concentrated. The residue was purified by silica gel chromatography eluting with 20% EtOAc/hexanes to afford the title compound: $^1$H NMR (500 MHz, CDCl$_3$): δ 7.55 (s, 1H), 7.53 (d, J=8.5 Hz, 1H); 7.39 (t, J=8.5 Hz, 1H); 6.96 (d, J=8.0 Hz, 1H); 2.98 (s, 3H).

Step D. 5-Bromo-3-chloro-1-methylisoquinoline

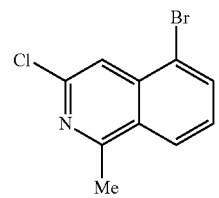 [SMILES: Cc1nc(Cl)cc2c(Br)cccc12]

To a solution of 5-amino-3-chloro-1-methylisoquinoline (460 mg, 2.4 mmol) in HBr (48%, 6 mL) and water (3 mL) at 0° C. was added slowly NaNO$_2$ (165 mg, 2.4 mmol) in water (3 mL). The reaction was stirred at 0° C. for 10 minutes, then the excess NaNO$_2$ was quenched by addition of a small amount of urea. The diazonium solution was then added slowly to a stirred solution of CuBr (411 mg, 2.9 mmol) in HBr (48%, 4 mL) at 75° C. The mixture was stirred for an additional 5 minutes at 75° C., then at room temperature for 18 hours. The mixture was poured onto crushed ice, adjusted to pH 9 with NH$_4$OH, then extracted with EtOAc. The combined organics were washed with water then saturated NaCl (aq), dried over Na$_2$SO$_4$, filtered, then concentrated. The residue was purified by silica gel chromatography eluting with 10% EtOAc/hexanes to afford the title compound: $^1$H NMR (500 MHz, CDCl₃): δ 8.09 (d, J=6.0 Hz, 1H), 7.98 (d, J=6.0 Hz, 1H); 7.97 (s, 1H), 7.44 (t, J=6.0 Hz, 1H); 2.98 (s, 3H). LC1: 2.68 min, (M+H): 256.

Step E. 5-Bromo-3-methoxy-1-methylisoquinoline

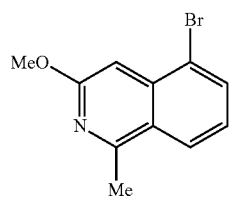 [SMILES: COc1cc2c(Br)cccc2c(C)n1]

Using the procedures from INTERMEDIATE 11 Step C, 5-bromo-3-chloro-1-methylisoquinoline was converted to the title compound: ¹H NMR (500 MHz, CDCl₃): δ 8.05 (d, J=8.5 Hz, 1H); 7.89 (d, J=8.5 Hz, 1H); 7.26 (t, J=8.5 Hz, 1H); 7.22 (s, 1H); 4.08 (s, 3H); 2.96 (s, 3H); LC6: 3.08 min. (M+H) 252.

Intermediate 13

5-Bromo-1-Methoxy-3-Methylisoquinoline

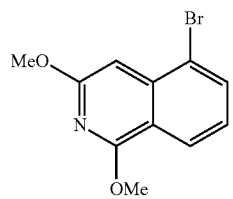 [SMILES: COc1cc2c(Br)cccc2c(OC)n1]

Step A. 3-Methyl-5-bromoisoquinoline

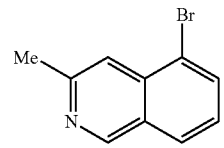 [SMILES: Cc1cc2c(Br)cccc2cn1]

Using the procedures from INTERMEDIATE 12 Steps B-D, 3-methylisoquinoline was converted to the title compound: ¹H NMR (500 MHz, CDCl₃): δ 9.18 (s, 1H), 7.97 (d, J=7.0 Hz, 1H), 7.94 (d, J=8.0 Hz, 1H); 7.84 (s, 1H), 7.42 (t, J=8.0 Hz, 1H); 2.80 (s, 3H). LC6: 2.62 min, (M+H): 222.

Step B. 5-Bromo-1-methoxy-3-methylisoquinoline

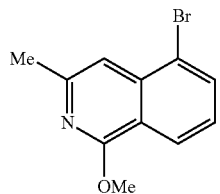 [SMILES: COc1nc(C)cc2c(Br)cccc12]

Using the procedures from INTERMEDIATE 4 Steps B and C, 5-bromo-3-methylisoquinoline was converted to the title compound: ¹H NMR (500 MHz, CDCl₃): δ 8.19 (d, J=8.0 Hz, 1H), 7.89 (d, J=7.5 Hz, 1H); 738 (s, 1H), 7.30 (t, J=8.5 Hz, 1H); 4.16 (s, 3H), 2.62 (s, 3H). LC6: 2.30 min. (M+H) 238.

Example 1

N-(4-{(1S) 1-[(4-Chlorophenyl)(6-Chloro-8-Methylquinolin-4-Yl)Methyl]Butyl}Benzoyl)-β-Alanine

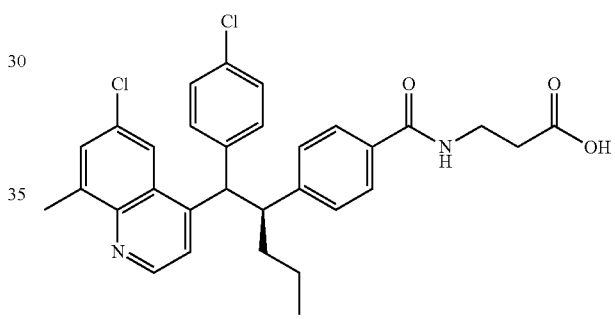

Step A. tert-Butyl 4-{(1R)-1-[(4-chlorophenyl)(6-chloro-8-methylquinolin-4-yl)(hydroxyl)methyl]butyl}benzoate

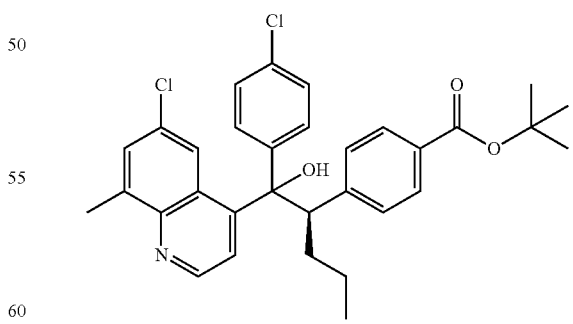

To a solution of n-BuLi (2.0 Min hexanes, 8.2 mL, 16.4 mmol) in anhydrous THF (15 mL) at −78° C. was added dropwise a solution of INTERMEDIATE 2 (4.5 g, 17.5 mmol) in THF (20 mL). After stirring for 15 minutes, a solution of INTERMEDIATE 1 (4.0 g, 10.7 mmol) in THF (20 mL) was added. The mixture was stirred at −78° C. for 30 minutes, then quenched with saturated NH₄Cl (aq). The mixture was extracted twice with EtOAc. The combined extracts were dried over MgSO₄, filtered, and concentrated. The residue was purified by silica gel chromatography eluting with 0-20% EtOAc/hexanes to afford the title compound: ¹H NMR (500 MHz, CDCl₃): δ 9.03 (d, J=4.6 Hz, 1H); 8.25 (s, 1H); 7.74 (d, J=8.1 Hz, 2H); 7.68 (d, J=4.6 Hz, 1H); 7.41 (s, 1H); 7.11 (d, J=8.0 Hz, 2H); 6.95 (s, 4H); 3.68 (d, J=10.8 Hz, 1H); 2.84 (s, 1H); 2.76 (s, 3H); 1.95 (m, 2H); 1.58 (s, 9H); 1.20 (m, 2H); 0.88 (m, 31:1); LC1 2.47 min. (M+H) 550.

Step B. tert-Butyl 4-{(1S)-1-[(4-chlorophenyl)(6-chloro-8-methylquinolin-4-yl)methyl]butyl}benzoate

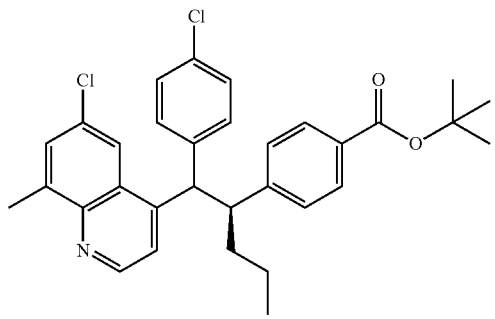 [SMILES: CCC[C@H](c1ccc(C(=O)OC(C)(C)C)cc1)C(c1ccc(Cl)cc1)c1ccnc2c(C)cc(Cl)cc12]

Method (a): To a suspension of NaH (60 mass % in mineral oil, 48 mg, 1.2 mmol) in THF (1.0 mL) at 0° C., was added the product from step A (166 mg, 0.301 mmol) in THF (2.0 mL). The mixture was stirred and allowed to warm to room temperature for one hour. The mixture was cooled to 0° C., then CS₂ (0.18 mL, 3.0 mmol) was added. The mixture was stirred and allowed to warm to room temperature for 30 minutes. The mixture was cooled to 0° C., then MeI (0.19 mL, 3.0 mmol) was added and the mixture was stirred and allowed to warm to room temperature for 16 hours. After quenching with methanol, the mixture was diluted with EtOAc and water. The organic phase was washed with water then saturated NaCl (aq), dried over MgSO₄, then concentrated. Purification by silica gel chromatography eluting with 0-10% EtOAc/hexanes gave the desired xanthate: LC4: 3.23 min. (M+H) 624.

The xanthate obtained (40 mg, 0.063 mmol) was mixed with nBu₃SnH (36 mg, 0.13 mmol) and AIBN (5 mg, 0.03 mmol), in toluene (3 mL). The apparatus was evacuated and refilled with dry nitrogen three times. The mixture was then placed in an oil bath at 100° C. After stirring for one hour, the solution was cooled to room temperature then concentrated. The residue was purified by preparative TLC eluting with 20% EtOAc/hexanes to provide the title compound. ¹H NMR indicates it is a mixture of two diastereomers in a ratio of 1:1.

Method (b): To a solution of the tertiary alcohol intermediate from Step A (4.84 g, 8.8 mmol) in THF (60 mL) at 0° C. was added LHMDS (1.0 M in toluene, 17.6 mL, 17.6 mmol). After stirring for five minutes, methyl oxalyl chloride (2.45 mL, 26.4 mmol) was added. After stirring for 30 minutes, the mixture was poured into water and diluted with EtOAc. The organic phase was washed three times with water and once with saturated NaCl (aq), dried over MgSO₄, filtered, then concentrated. The resulting colorless oil was used directly for the following step: LC1: 2.68 min. (M+H) 636.

The residue was azeotroped with toluene and dried in vacuo. It was then dissolved in toluene (60 mL) and nBu₃SnH (4.7 mL, 17.6 mmol) and AIBN (0.29 g, 1.76 mmol) were added. The apparatus was evacuated and refilled with dry nitrogen three times. The mixture was then placed in an oil bath at 100° C. After stirring for four hours, LC/MS analysis showed remaining starting material. Additional nBu₃SnH (2.4 mL, 8.8 mmol) and AIBN (0.15 g, 0.90 mmol) were added, and the apparatus was evacuated and refilled with dry nitrogen three times. The mixture was then placed in an oil bath at 100° C. After stirring for two hours, LC/MS showed complete conversion of starting material. The solution was cooled to room temperature then concentrated. The residue was purified by silica gel chromatography eluting with 0-20% EtOAc/hexanes to afford a mixture of the title compounds as a colorless oil (1:1 d.r. by ¹H NMR analysis). LC1: 2.54 min. (M+H) 534.

Step C. N-(4-{(1S)-1-[(4-chlorophenyl)(6-chloro-8-methylquinolin-4-yl)methyl]butyl}benzoyl)-β-alanine

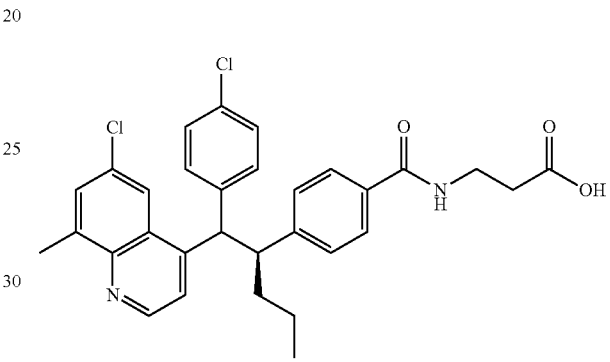

The product of Step C (4.16 g, 7.8 mmol) was dissolved in CH₂Cl₂ (6 mL) then TFA (6 mL) was added. After stirring at room temperature for 2 hours, the solution was concentrated. The resulting oil was used directly for the following step.

The residue from the previous step was dissolved in DMF (40 mL), then t-butyl β-alaninate hydrochloride (2.83 g, 15.6 mmol), EDC (5.97 g, 31.1 mmol), HOBt (0.60 g, 3.9 mmol) and diisopropylethylamine (27 mL, 156 mmol) were added. The resulting mixture was stirred at room temperature for 16 h. The mixture was diluted with EtOAc, washed with water then saturated NaCl (aq), dried over MgSO₄, filtered, and concentrated. The residue was purified, and the diastereomers separated, by silica gel chromatography eluting with 0-20% EtOAc/hexanes to afford each diastereomeric product as a colorless oil.

A solution of the faster-eluting diastereomer in CH₂Cl₂ (2.5 mL) was treated with TFA (2.5 mL). After stirring at room temperature for two hours, the solution was concentrated. The residue was purified by preparative reverse-phase HPLC, eluting with 10-70% acetonitrile/water+0.1% TFA. Following lyophilization, this afforded the title compound (Diastereomer A) as a white solid: ¹H NMR (500 MHz, CDCl₃): δ 9.29 (d, J=5.2 Hz, 1H); 8.13 (s, 1H); 7.88 (d, J=5.2 Hz, 1H); 7.67 (s, 1H); 7.63 (d, J=7.9 Hz, 2H); 7.22 (d, J=8.0 Hz, 2H); 7.02 (d, J=8.4 Hz, 2H); 6.96 (d, J=8.4 Hz, 2H); 6.75 (t, 1H, J=6.4 Hz); 4.88 (d, J=11.2 Hz, 1H); 3.73 (q, J=5.8 Hz, 2H); 3.58 (m, 1H); 2.87 (s, 3H); 2.73 (t, 2H, J=5.9 Hz); 1.54-1.61 (m, 2H), 1.10-1.03 (m, 2H); 0.73 (t, 3H, J=7.3 Hz); LC4 2.46 min. (M+H) 549.

The slower-eluting (lower Rf) diastereomer was hydrolyzed in a manner similar to the faster-eluting (higher Rf) diastereomer to afford diastereomer B as a white solid: ¹H NMR (500 MHz, CDCl₃): δ 9.09 (d, J=5.6 Hz, 1H); 8.18 (s, 1H); 7.90 (d, J=5.3 Hz, 1H); 7.67 (s, 1H); 7.52 (d, J=7.9 Hz, 2H); 7.41-7.33 (m, 4H); 7.21 (d, =7.9 Hz, 2H); 6.90 (t, J=5.9 Hz, 1H); 5.04 (d, J=11.3 Hz, 1H); 3.68-3.54 (m, 3H); 2.77 (s, 3H); 2.59 (t, J=5.8 Hz, 2H); 1.67-1.54 (m, 2H); 1.13-1.03 (m, 2H); 0.77 (t, J=7.3 Hz, 3H).

The absolute stereochemistry of the two diastereomers in EXAMPLE 1 is shown in the figure below. The stereochemistry assignment is based on the X-ray crystallography of diastereomer B and the observed Nuclear Overhauser Effect (NOE, represented by an asterisk) and a low energy conformational model of the two diastereomers.

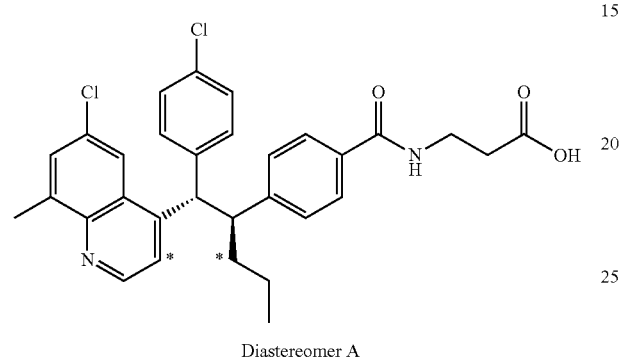

Diastereomer A

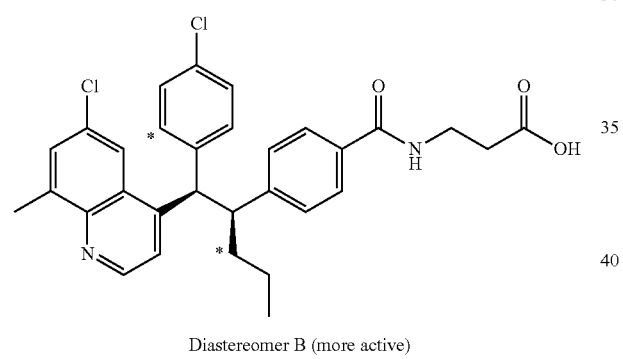

Diastereomer B (more active)

Example 2

N-(4-{(1S)-1-[(4-Chlorophenyl)(2-Methoxyquinolin-5-Yl)Methyl]Butyl}Benzoyl)-β-Alanine

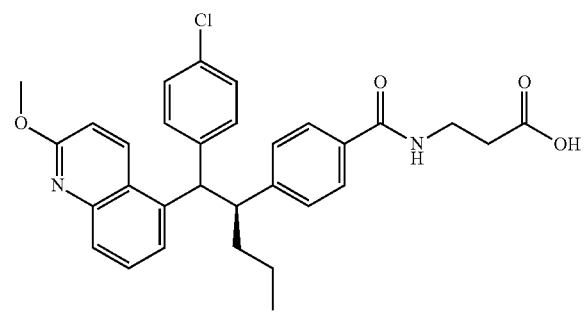 [SMILES: CCC[C@H](c1ccc(C(=O)NCCC(=O)O)cc1)C(c1ccc(Cl)cc1)c1cccc2nc(OC)ccc12]

Step A. tert-Butyl 4-{(1R)-1-[(4-chlorophenyl)(2-methoxylquinolin-5-yl)(hydroxyl)methyl]butyl}benzoate

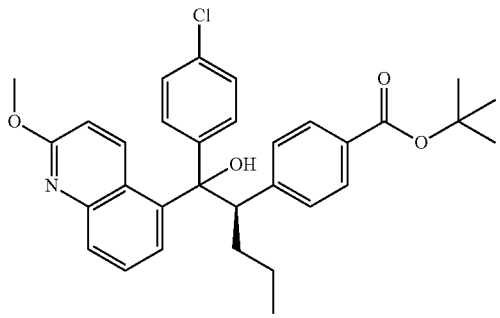 [SMILES: CCC[C@H](c1ccc(C(=O)OC(C)(C)C)cc1)C(O)(c1ccc(Cl)cc1)c1cccc2nc(OC)ccc12]

To a solution of INTERMEDIATE 3 (140 mg, 0.60 mmol) in anhydrous THF (6 mL) at −78° C. was added nBuLi (2.5 M in hexanes, 0.2 mL, 0.5 mmol) dropwise. After stirring for 30 minutes, a solution of INTERMEDIATE 1 (185 mg, 0.50 mmol) in THF (2 mL) was added. After stirring at −78° C. for one hour, the cold solution was poured into saturated NH₄Cl (aq). The mixture was extracted twice with EtOAc, dried over MgSO₄, filtered, then concentrated. The residue was purified by silica gel chromatography eluting with 0-20% EtOAc/hexanes to afford the title compound: LC1: 2.62 min. (M+H) 532.

Step B. 4-{(1S)-1-[(4-chlorophenyl)(2-methoxyquinolin-5-yl)methyl]butyl}benzoic acid

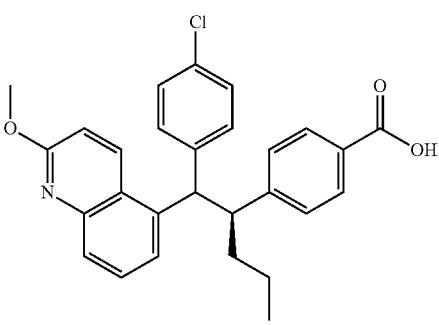 [SMILES: CCC[C@H](c1ccc(C(=O)O)cc1)C(c1ccc(Cl)cc1)c1cccc2nc(OC)ccc12]

The product of step A (85 mg, 0.160 mmol) was dissolved in CH₂Cl₂ (15 mL) and triethylsilane (0.26 ml, 1.6 mmol) was added. The solution was cooled to −78° C., then BF₃ gas was slowly bubbled through the solution until it was saturated (less than one minute, at the time fuming BF₃ was observed from a small needle venting from the flask). The mixture was allowed to warm gradually to −20° C. When all starting material was consumed by LC/MS analysis, 1 N HCl (aq) was added and the mixture was allowed to warm to room temperature. The mixture was extracted twice with CH₂Cl₂. The combined organic extracts were washed with water, dried over MgSO$_4$, then concentrated. This afforded the title compound, which was used in the next step without purification: LC1 2.29 min. (M+H) 460.

Step C. N-(4-{(1S)-1-[(4-chlorophenyl)(2-methoxyquinolin-5-yl)methyl]butyl}benzoyl)-β-alanine

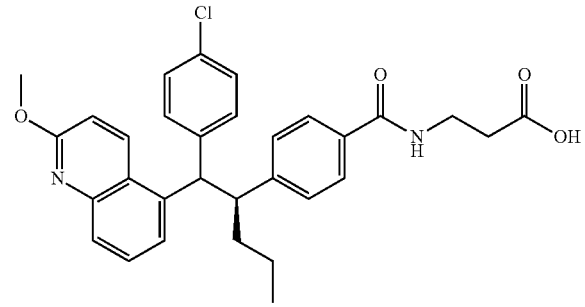 [SMILES: CCC[C@H](c1ccc(C(=O)NCCC(=O)O)cc1)C(c1ccc(Cl)cc1)c1cccc2nc(OC)ccc12]

The product of Step B was dissolved in CH$_2$Cl$_2$ (8 mL), then tert-butyl β-alaninate hydrochloride (64.8 mg, 0.359 mmol), EDC (92 mg, 0.48 mmol), HOBt (36.6 mg, 0.239 mmol) and diisopropylethylamine (0.21 mL, 1.20 mmol) were added. The resulting mixture was stirred at room temperature until all starting material was consumed by LC/MS analysis. The mixture was diluted with CH$_2$Cl$_2$, washed with water then saturated NaCl (aq), dried over MgSO$_4$, then concentrated. The residue was purified, and the two diastereomers were separated, by preparative TLC eluting with 25% EtOAc/hexanes.

Each diastereomer was independently dissolved in CH$_2$Cl$_2$ (0.5 mL) then treated with TFA (0.5 mL). After stirring at room temperature for two hours, the solutions were concentrated. The residues were purified by reverse-phase HPLC eluting with 10-75% acetonitrile/water containing 0.1% TFA. Following lyophilization, this afforded the two diastereomers of the title compound as white solids:

Diastereomer A (from the faster-eluting t-butyl ester precursor): $^1$H NMR (500 MHz, CDCl$_3$): δ 8.45 (d, J=9.3 Hz, 1H); 7.86 (d, J=8.3 Hz, 1H); 7.74 (t, J=7.4 Hz, 1H); 7.63 (d, J=7.4 Hz, 1H); 7.60 (d, J=8.0 Hz, 2H); 7.20 (d, J=8.0 Hz, 2H); 6.97-6.92 (m, 5H); 6.78 (t, J=5.8 Hz, 1H); 4.79 (d, J=11.2 Hz, 1H); 4.11 (s, 3H); 3.73 (q, J=5.7 Hz, 4H); 3.57 (dt, J=8.1, 2.7 Hz, 2H); 2.74 (t, J=6.0 Hz, 2H); 1.66-1.74 (m, 1H); 1.46-1.56 (m, 1H); 1.05-1.00 (m, 2H); 0.71 (t, J=7.1 Hz, 3H); LC1 2.13 min. (M+H) 531.

Diastereomer B (from the slower-eluting t-butyl ester precursor, more active diastereomer): $^1$H NMR (500 MHz, CDCl$_3$): δ 8.58 (d, J=9.5 Hz, 1H); 7.72 (d, J=7.7 Hz, 1H); 7.60-7.52 (m, 2H); 7.43 (d, 0.1=7.9 Hz, 2H); 7.36 (d, J=8.4 Hz, 2H); 7.31 (d, J=8.3 Hz, 2H); 7.12 (d, J=7.9 Hz, 2H); 6.99 (d, J=9.4 Hz, 1H); 7.02-6.72 (m, 1H); 4.83 (d, J=11.3 Hz, 1H); 4.07 (s, 3H); 3.58-3.49 (m, 3H); 2.54 (s, 2H); 1.72-1.54 (m, 2H); 1.12-0.98 (m, 2H); 0.76 (t, J=7.3 Hz, 3H); LC1 2.14 min (M+H) 531.

Example 3

N-(4-{(1S)-1-[(4-Chlorophenyl)(7-Trifluoromethylquinolin-3-Yl)Methl]Butyl}Benzoyl)-β-Alanine

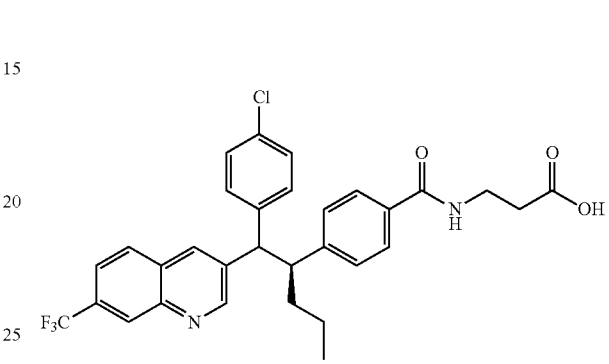

Step A. tert-Butyl 4-{(1R)-1-[(4-chlorophenyl)(7-trifluoromethylquinolin-3-yl)(hydroxyl)methyl]butyl}benzoate

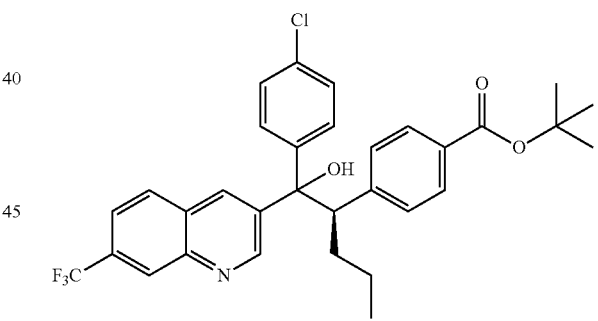

To a solution of 3-bromo-7-trifluoromethylquinoline (220 mg, 0.80 mmol) in anhydrous THF (6 mL) at −78° C. was added nBuLi (2.5M in hexanes, 0.30 mL, 0.75 mmol) dropwise. After stirring for 30 minutes, a solution of INTERMEDIATE 1 (200 mg, 0.54 mmol) in THF (2 mL) was added. After stirring at −78° C. for one hour, the mixture was poured into saturated NH$_4$Cl (aq). The mixture was extracted twice with EtOAc. The organic extracts were dried over MgSO$_4$, filtered, then concentrated. The residue was purified by silica gel chromatography eluting with 0-10% EtOAc/hexanes to afford the title compound: $^1$H NMR (500 MHz, CDCl$_3$): δ 9.18 (d, J=2.3 Hz, 1H); 8.39 (m, 2H); 7.96 (d, J=8.5 Hz, 1H); 7.80 (d, J=8.1 Hz, 2H); 7.75 (dd, J=8.1, 1.5 Hz, 1H); 7.25-7.18 (tn, 4H); 7.14-7.08 (m, 2H); 3.92 (dd, J=11.9, 2.5 Hz, 1H); 2.94 (s, 1H); 1.94-1.83 (m, 1H); 1.57 (s, 9H); 1.17-1.06 (m, 2H); 0.77 (t, J=7.3 Hz, 3H); LC1 2.69 min. (M+H) 570.

Step B. 4-{(1S)-1-[(4-chlorophenyl)-(7-trifluoromethylquinolin-3-yl)methyl]butyl}benzoic acid

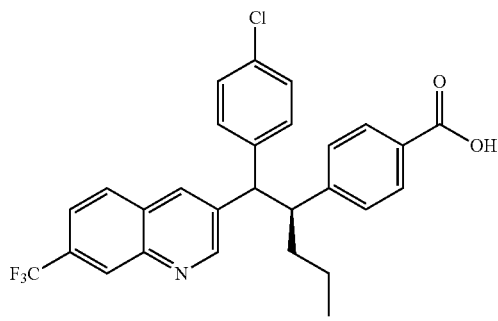 [SMILES: CCC[C@H](c1ccc(C(=O)O)cc1)C(c1ccc(Cl)cc1)c1cnc2cc(C(F)(F)F)ccc2c1]

The product of step A (98 mg, 0.173 mmol) was dissolved in CH$_2$Cl$_2$ (15 mL) and triethylsilane (0.28 ml, 1.72 mmol) was added. The solution was cooled to −78° C., then BF$_3$ gas was slowly bubbled through the solution until it was saturated (less than one minute, at the time fuming BF$_3$ was observed from a small needle venting from the flask). The mixture was allowed to warm gradually to −20° C. When all starting material was consumed by LC/MS analysis, saturated NaHCO$_3$ (aq) was added and the mixture was allowed to warm to room temperature. The mixture was extracted twice with EtOAc. The combined organic extracts were washed with water, dried over MgSO$_4$, filtered, then concentrated. This afforded a mixture of diastereomers of the title compound, which was used in the next step without purification: LC1 2.39 min, (M+H) 498, Step C. N-(4-{(1S)-1-[(4-chlorophenyl)(7-trifluoromethylquinolin-5-yl)methyl]butyl}benzoyl)-β-alanine

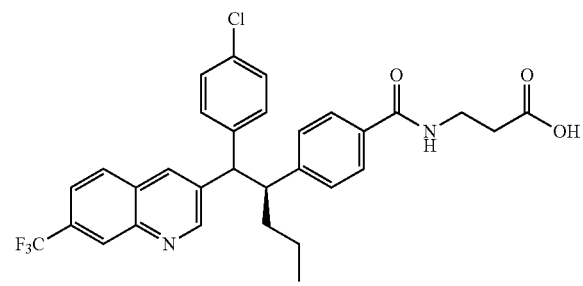 [SMILES: CCC[C@H](c1ccc(C(=O)NCCC(=O)O)cc1)C(c1ccc(Cl)cc1)c1cnc2cc(C(F)(F)F)ccc2c1]

The product of Step B was dissolved in DMF (2 mL), then tert-butyl β-alaninate hydrochloride (53 mg, 0.29 mmol), EDC (56 mg, 0.29 mmol), HOBt (22 mg, 0.15 mmol) and diisopropylethylamine (0.26 mL, 1.5 mmol) were added. The resulting mixture was stirred at room temperature until all starting material was consumed by LC/MS analysis. The mixture was diluted with EtOAc, washed with water then saturated NaCl (aq), dried over MgSO$_4$, then concentrated to afford the title compound. The two diastereomers were inseparable by TLC analysis, so the mixture was used in the next step without additional purification.

The product from the previous step was dissolved in CH$_2$Cl$_2$ (0.5 mL) then TFA (0.5 mL) was added. Once all starting material was consumed by LC/MS analysis, the solution was concentrated. The residue was purified by reverse-phase HPLC, eluting with 10-60% acetonitrile/water+0.1% TFA. Following lyophilization, this afforded the two diastereomeric title compounds as white solids.

Faster-eluting diastereomer: $^1$H NMR (500 MHz, CDCl$_3$): δ 9.33 (d, J=2.1 Hz, 1H); 8.57 (s, 1H); 8.45 (s, 1H); 8.10 (d, J=8.6 Hz, 1H); 7.90 (d, J=8.7 Hz, 1H); 7.62 (d, J=7.9 Hz, 2H); 7.09 (s, 4H); 6.84 (t, J=6.1 Hz, 1H); 4.46 (d, J=11.4 Hz, 1H); 3.73 (q, J=5.8 Hz, 2H); 3.66-3.59 (m, 1H); 2.73 (t, J=5.8 Hz, 2H); 1.60-1.48 (m, 2H); 1.08-1.01 (m, 2H); 0.72 (t, J=7.3 Hz, 3H); LC1 2.26 min, (M+H) 569.

Slower-eluting diastereomer (more active diastereomer): $^1$H NMR (500 MHz, CDCl$_3$): δ 8.89 (s, 1H); 8.35 (s, 1H); 8.09 (s, 1H); 7.87 (d, J=8.6 Hz, 1H); 7.75 (d, J=8.4 Hz, 1H); 7.56 (d, J=7.7 Hz, 2H); 7.39 (s, 4H); 7.22 (d, J=8.1 Hz, 2H); 6.84 (m, 1H); 4.39 (d, J=11.6 Hz, 1H); 3.66 (q, J=6.4 Hz, 2H); 3.57 (m, 1H); 2.68-2.63 (m, 2H); 1.52-1.75 (m, 2H); 1.09-1.03 (m, 2H); 0.77 (t, J=7.3 Hz, 3H); LC1 2.28 min. (M+H) 569.

The compounds in TABLES 1-5 were prepared using the chemistry described for the preparation of INTERMEDIATES 1-13 and in EXAMPLES 1-3. The compounds in TABLES 1-4 were prepared as enantiopure compounds. In these tables, and for the enantiopure compounds in TABLE 5, the data listed is for the most active stereoisomer. The R$^1$ and R$^3$ groups that are shown in tables 1-7 are specified when they represent a value other than a hydrogen atom. The remaining R$^1$ and R$^3$ groups that are unspecified are hydrogen atoms. Racemic compounds were prepared from their corresponding racemic intermediates. The data for the racemic compounds is for the more active diastereomer.

TABLE 1

| EXAMPLE | R$^1$ | R$^2$ | R$^3$ | LC-MS data |
|---|---|---|---|---|
| 4 | 4-Cl | n-Pr | 2-Me, 8-OMe | LC1 2.01 min. (M + H) 545 |
| 5 | 4-Cl | n-Pr | 2-Me, 6-OMe | LC1 1.92 min. (M + H) 545 |
| 6 | 4-Cl | n-Pr | 6-CF$_3$ | LC1 2.08 min. (M + H) 569 |
| 7 | 4-Cl | n-Pr | 7-Cl | LC4 2.34 min. (M + H) 535 |
| 8 | 4-Cl | n-Pr | 2-CF$_3$ | LC4 2.54 min. (M + H) 569 |
| 9 | 4-Cl | n-Pr | 6-OMe, 8-Me | LC5 1.21 min. (M + H) 545 |
| 10 | 4-Cl | n-Pr | 6-OMe, 8-Cl | LC4 2.40 min. (M + H) 565 |
| 11 | 4-Cl | n-Pr | 6-CF$_3$, 8-Me | LC4 2.59 min. (M + H) 583 |
| 12 | 4-Cl | n-Pr | 7-CF$_3$ | LC5 1.30 min. (M + H) 569 |
| 13 | 4-Cl | n-Pr | 6-CF$_3$, 8-F | LC5 1.33 min. (M + H) 587 |
| 14 | 4-Cl | n-Pr | 6-OMe, 8-CF$_3$ | LC4 2.55 min. (M + H) 599 |

TABLE 1-continued

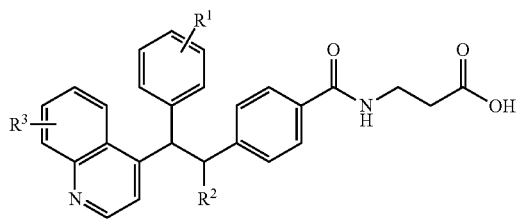

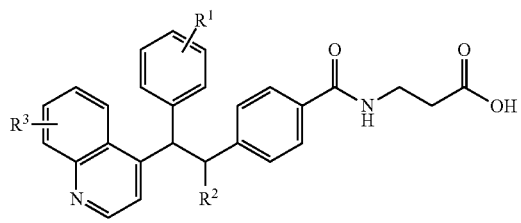

| EXAMPLE | R¹ | R² | R³ | LC-MS data |
|---|---|---|---|---|
| 15 | 4-Cl | n-Pr | 6,8-diF | LC4 2.44 min. (M + H) 537 |
| 16 | 4-Cl | n-Pr | 6-Cl, 8-F | LC4 2.46 min. (M + H) 553 |
| 17 | 4-Cl | n-Pr | 2-OMe | LC4 2.53 min. (M + H) 531 |
| 18 | 4-OCF₃ | n-Pr | 6-Cl, 8-Me | LC5 1.34 min. (M + H) 599 |
| 19 | 4-Cl | n-Pr | 8-CF₃ | LC5 1.33 min. (M + H) 569 |
| 20 | 3-CF₃ | n-Pr | 7-Cl | LC4 2.41 min. (M + H) 569 |
| 21 | 4-Cl | n-Pr | 6-Me, 8-Cl | LC4 2.46 min. (M + H) 549 |
| 22 | 4-Cl | n-Pr | 2-CF₃, 6-Cl | LC1 2.43 min. (M + H) 603 |
| 23 | 4-Cl | n-Pr | 2-Me, 6-Cl | LC1 1.91 min. (M + H) 549 |
| 24 | 4-Cl | n-Pr | 7-OCF₃ | LC2 1.17 min. (M + H) 585 |
| 25 | 4-Cl | Et | 7-Cl | LC2 1.12 min. (M + H) 521 |
| 26 | 4-OCF₃ | n-Pr | 7-Cl | LC2 1.16 min. (M + H) 585 |
| 27 | 4-Cl | n-Pr | 7-F | LC4 2.31 min. (M + H) 519 |
| 28 | 4-Cl | n-Pr | 7-F, 8-Me | LC1 1.87 min. (M + H) 533 |
| 29 | 4-Cl | n-Pr | 2-OMe, 8-F | LC1 1.89 min. (M + H) 549 |
| 30 | 4-Cl | n-Pr | 7-OMe | LC1 1.82 min. (M + H) 531 |
| 31 | 4-Cl | n-Pr | 6-F, 8-CF₃ | LC1 2.30 min. (M + H) 587 |
| 32 | 4-Cl | n-Pr | 7-Me | LC1 2.82 min. (M + H) 515 |
| 33 | 4-Cl | n-Pr | 7,8-diCl | LC4: 2.43 min. (M + H) 62 |
| 34 | 4-Cl | n-Pr | 7-Cl, 8-F | LC4: 2.33 min. (M + H) 553 |
| 35 | 4-Cl | n-Pr | 6-F, 8-Me | LC4: 2.24 min. (M + H) 533 |
| 36 | 4-Cl | n-Pr | 7-Cl, 8-Me | LC4: 2.46 min. (M + H) 549 |
| 37 | 4-Cl | n-Pr | 2-Me, 7-Cl | LC4: 2.09 min. (M + H) 549 |
| 38 | 4-Cl | n-Pr | 2-CF₃, 7-Cl | LC4: 2.64 min. (M + H) 603 |
| 39 | 4-Cl | n-Pr | 2-OMe, 7-Cl | LC4: 2.56 min. (M + H) 565 |
| 40 | 4-Cl | n-Pr | 6-Cl, 8-CF₃ | LC4: 2.37 min. (M + H) 603 |
| 41 | 4-Cl | n-Pr | 6-F, 7-CF₃ | LC4: 2.48 min. (M + H) 588 |
| 42 | 4-Cl | n-Pr | 7-CF₃, 8-F | LC4: 2.43 min. (M + H) 588 |
| 43 | 4-Cl | n-Pr | 6-Cl | LC4: 2.23 min. (M + H) 535 |
| 44 | 4-Cl | n-Pr | 7,8-diF | LC4: 2.07 min. (M + H) 537 |
| 45 | 4-Cl | n-Pr | 6-CF₃, 8-Cl | LC3: 2.52 min. (M + H) 603 |
| 46 | 4-Cl | n-Pr | 6-Cl, 8-Cl | LC 3: 2.64 min. (M + H) 567 |
| 47 | 4-Cl | n-Pr | 6-Cl, 7-Cl | LC2: 1.28 min. (M + H) 571 |
| 48 | 4-Cl | n-Pr | 6-Cl, 7-F | LC3: 2.39 min. (M + H) 553 |
| 49 | 4-Cl | n-Pr | 6-Me, 7-Cl | LC1: 2.12 min. (M + H) 549 |
| 50 | 4-Cl | n-Pr | 6-Cl, 7-Me | LC1: 2.12 min. (M + H) 549 |
| 51 | 4-Cl | n-Pr | 6-OCF₃, 8-Cl | LC2: 1.25 min. (M + H) 620 |
| 52 | 4-Cl | n-Pr | 6-OCF₃, 8-Me | LC2: 1.21 min. (M + H) 600 |
| 53 | 4-Cl | n-Pr | 6,7-diCl, 8-F | LC4: 2.61 min. (M + H) 587 |
| 54 | 4-Cl | n-Pr | 6-Me, 7,8-diF | LC4: 2.32 min. (M + H) 551 |
| 55 | 4-Cl | —CH₂CH₂CF₃ | 7-Cl | LC1: 1.81 min. (M + H) 589 |
| 56 | 4-Cl | —CH₂CH₂CF₃ | 6-CF₃, 8-F | LC1: 2.21 min. (M + H) 641 |
| 57 | 4-Cl | —CH₂CH₂CF₃ | 6-Me, 8-Cl | LC1: 2.10 min. (M + H) 603 |
| 58 | 4-Cl | Et | 7-OCF₃ | LC1: 2.04 min. (M + H) 571 |
| 59 | 4-CF₃ | Et | 7-Cl | LC1: 1.78 min. (M + H) 555 |
| 60 | 4-OCF₃ | Et | 7-Cl | LC1: 1.81 min. (M + H) 571 |
| 61 | 4-Cl | n-Pr | 6-Me, 7-CF₃ | LC2: 1.37 min. (M + H) 583 |
| 62 | 4-OCF₃ | n-Pr | 7-F | LC1: 1.71 min. (M + H) 569 |
| 63 | 4-OCF₃ | n-Pr | 6-Cl, 8-F | LC1: 2.13 min. (M + H) 603 |
| 64 | 4-OCF₃ | n-Pr | 6-Me, 7-F | LC1: 1.87 min. (M + H) 583 |
| 65 | 4-OCF₃ | n-Pr | 6-Cl, 7-Me | LC1: 1.97 min. (M + H) 599 |
| 66 | 4-Cl | n-Pr | 6-F, 7-Me | LC1: 1.88 min. (M + H) 533 |
| 67 | 4-CF₃ | n-Pr | 7-F | LC1: 1.83 min. (M + H) 553 |
| 68 | 4-CF₃ | n-Pr | 6-Me, 7-F | LC1: 1.89 min. (M + H) 567 |
| 69 | 4-CF₃ | n-Pr | 6-Cl, 7-Me | LC1: 1.96 min. (M + H) 583 |
| 70 | 4-CF₃ | n-Pr | 6-F, 7-Me | LC1: 1.94 min. (M + H) 567 |
| 71 | 4-CF₃ | n-Pr | 6-Cl, 8-Me | LC1: 2.04 min. (M + H) 583 |
| 72 | 4-Cl | n-Pr | 6-F, 7-Me, 8-F | LC1: 2.06 min. (M + H) 551 |
| 73 | 4-Cl | n-Pr | 7-Me, 8-F | LC1: 1.80 min. (M + H) 533 |
| 74 | 4-Cl | n-Pr | 6-Me, 7-F | LC1: 1.84 min. (M + H) 533 |
| 75 | 4-Cl | —CH₂CH₂CF₃ | 7-F | LC1: 1.80 min. (M + H) 573 |
| 76 | 4-Cl | —CH₂CH₂CF₃ | 6-Me, 7-F | LC1: 1.86 min. (M + H) 587 |
| 77 | 4-Cl | —CH₂CH₂CF₃ | 6-F, 7-Me | LC1: 1.92 min. (M + H) 587 |
| 78 | 4-Cl | —CH₂CH₂CF₃ | 6-Cl, 8-Me | LC1: 2.02 min. (M + H) 605 |
| 79 | 4-Cl | —CH₂CH₂CF₃ | 6-Cl, 7-Me | LC1: 1.78 min. (M + H) 605 |

TABLE 1-continued

| EXAMPLE | R¹ | R² | R³ | LC-MS data |
|---|---|---|---|---|
| 80 | 4-Cl | —CH₂CH₂CF₃ | 6-Me, 8-F | LC1: 1.81 min. (M + H) 587 |
| 81 | 4-Cl | —CH₂CH₂CF₃ | 5-Me, 7-F | LC1: 1.92 min. (M + H) 587 |
| 82 | 4-Cl | —CH₂CH₂CF₃ | 5-F, 7-Me | LC1: 1.93 min. (M + H) 587 |
| 83 | 4-Cl | n-Pr | 6-Me, 8-F | LC1: 1.79 min. (M + H) 533 |
| 84 | 3-Cl, 4-Cl | n-Pr | 6-Cl, 8-Me | LC1: 2.03 min. (M + H) 585 |
| 85 | 3-Cl, 4-Cl | n-Pr | 7-F | LC1: 1.73 min. (M + H) 553 |
| 86 | 3-Cl, 4-Cl | n-Pr | 6-Me, 8-F | LC1: 1.90 min. (M + H) 567 |
| 87 | 3-Cl, 4-Cl | n-Pr | 6-Cl, 7-Me | LC1: 1.87 min. (M + H) 585 |
| 88 | 3-Cl, 5-Cl | n-Pr | 6-Cl, 8-Me | LC1: 2.06 min. (M + H) 585 |
| 89 | 3-Cl, 5-Cl | n-Pr | 7-F | LC1: 1.90 min. (M + H) 553 |

TABLE 2

| EXAMPLE | R¹ | R² | R³ | LC-MS data |
|---|---|---|---|---|
| 90 | 4-Cl | n-Pr | H | LC1 1.84 min. (M + H) 501 |
| 91 | 4-Cl | n-Pr | 2-Me, 8-OMe | LC1 1.89 min. (M + H) 545 |
| 92 | 4-OCF₃ | n-Pr | 2-OMe | LC1 2.28 min. (M + H) 581 |
| 93 | 3-Cl | n-Pr | 2-OMe | LC1 2.15 min. (M + H) 531 |
| 94 | 3,5-diF | n-Pr | 2-OMe | LC5 1.27 min. (M + H) 533 |
| 95 | 4-OMe | n-Pr | 2-OMe | LC5 1.26 min. (M + H) 527 |
| 96 | 3-F, 4-Cl | n-Pr | 2-OMe | LC2 1.23 min. (M + H) 549 |
| 97 | 3-CF₃ | n-Pr | 2-OMe | LC5 1.32 min. (M + H) 565 |
| 98 | 4-Me | n-Pr | 2-OMe | LC4 2.46 min. (M + H) 511 |
| 99 | 4-Cl | n-Pr | 2-OMe, 8-F | LC1 2.28 min. (M + H) 549 |
| 100 | 4-Cl | n-Pr | 7-Cl | LC6: 3.57 min. (M + H) 535 |
| 101 | 4-Cl | n-Pr | 2-Cl | LC2: 1.52 min. (M + H) 535 |
| 102 | 4-Cl | n-Pr | 2-OMe, 7-Cl | LC6: 3.85 min. (M + H) 566 |

TABLE 2-continued

| EXAMPLE | R¹ | R² | R³ | LC-MS data |
|---|---|---|---|---|
| 103 | 4-Cl | n-Pr | 2-OEt | LC3: 2.53 min. (M + H) 545 |
| 104 | 4-Cl | n-Pr | 2-OCH₂CF₃ | LC2: 1.16 min. (M + H) 599 |
| 105 | 4-Cl | n-Pr | 2-O(n-Pr) | LC2: 1.46 min. (M + H) 559 |
| 106 | 4-Cl | n-Pr | 2-O(i-Pr) | LC3: 2.27 min. (M + H) 559 |
| 107 | 4-Cl | n-Pr | 2-O(i-Bu) | LC2: 1.52 min. (M + H) 573 |
| 108 | 4-Cl | n-Pr | 2-O(cyclobutyl) | LC2: 1.48 min. (M + H) 571 |
| 109 | 4-Cl | n-Pr | 2-O(cyclopentyl) | LC2: 1.48 min. (M + H) 585 |
| 110 | 4-Cl | n-Pr | 2-O(cyclohexyl) | LC2: 1.52 min. (M + H) 599 |
| 111 | 4-Cl | n-Pr | 2-OMe, 3-Me | LC2: 1.25 min. (M + H) 546 |
| 112 | 4-Cl | n-Pr | 2-OCH₂CH₂OMe | LC2: 1.25 min. (M + H) 575 |
| 113 | 4-Cl | n-Pr | 2-OCH₂CH₂NMe₂ | LC2: 1.16 min. (M + H) 588 |
| 114 | 4-Cl | n-Pr | 2-CN | LC2: 1.21 min. (M + H) 526 |
| 115 | 4-OCF₃ | Et | 2-OMe | LC4: 2.55 min. (M + H) 567 |
| 116 | 4-CF₃ | Et | 2-OMe | LC4: 2.51 min. (M + H) 551 |
| 117 | 4-Cl | Et | 2-OMe | LC7: 3.38 min. (M + H) 517 |
| 118 | 4-F | n-Pr | 2-OMe | LC7: 3.31 min. (M + H) 515 |
| 119 | 4-Cl | Me | 2-OMe | LC7: 3.32 min. (M + H) 503 |

TABLE 3

| EXAMPLE | R¹ | R² | R³ | LC-MS data |
|---|---|---|---|---|
| 120 | 4-Cl | n-Pr | 2-OMe | LC1 2.18 min. (M + H) 531 |
| 121 | 4-Cl | n-Pr | H | LC1 1.89 min. (M + H) 501 |
| 122 | 4-Cl | n-Pr | 2-OMe, 8-Me | LC7 3.81 min. (M + H) 545 |
| 123 | 4-Cl | n-Pr | 2-OMe, 7-Me | LC7 3.46 min. (M + H) 545 |

TABLE 3-continued

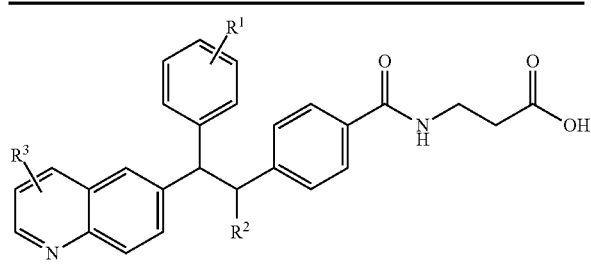

| EXAMPLE | R¹ | R² | R³ | LC-MS data |
|---|---|---|---|---|
| 124 | 4-Cl | n-Pr | 2-Cl, 7-Me | LC6 4.31 min. (M + H) 549 |
| 125 | 4-Cl | n-Pr | 2-OMe | LC7 3.53 min. (M + H) 565 |
| 126 | 4-Cl | —CH$_2$C(CH$_3$)$_3$ | 2-OMe | LC6: 4.37 min. (M + H) 559 |
| 127 | 4-Cl | —CH$_2$CH$_2$CF$_3$ | 2-OMe | LC6: 4.11 min. (M + H) 585 |
| 128 | 4-Cl | n-Pr | 2-OMe, 5-F | LC6: 4.35 min. (M + H) 549 |
| 129 | 4-Cl | n-Pr | 2-OMe, 8-F | LC6: 4.37 min. (M + H) 549 |

TABLE 4

| EXAMPLE | R¹ | R² | R³ | LC-MS data |
|---|---|---|---|---|
| 130 | 4-Cl | n-Pr | 6-Cl | LC6: 3.24 min. (M + H 535. |

TABLE 4-continued

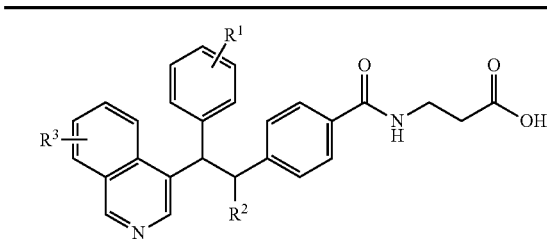

| EXAMPLE | R¹ | R² | R³ | LC-MS data |
|---|---|---|---|---|
| 131 | 4-Cl | n-Pr | 8-Cl | LC6: 3.43 min. (M + H) 535 |
| 132 | 4-Cl | n-Pr | 7,8-diCl | LC6: 3.97 min. (M + H) 569 |
| 133 | 4-Cl | —CH$_2$CH$_2$CF$_3$ | 8-Cl | LC6: 3.50 min. (M + H) 589 |
| 134 | 4-OCF$_3$ | n-Pr | 8-Cl | LC6: 3.53 min. (M + H) 585 |
| 135 | 4-CF$_3$ | n-Pr | 8-Cl | LC6: 3.50 min. (M + H) 569 |
| 136 | 4-Cl | n-Pr | 7-Cl | LC3: 2.33 min. (M + H) 535 |
| 137 | 4-CF$_3$ | n-Pr | 7-Cl | LC6: 3.42 min. (M + H) 569 |
| 138 | 4-Cl | —CH$_2$CH$_2$CF$_3$ | 7-Cl | LC6: 3.41 min. (M + H) 589 |
| 139 | 4-OCF$_3$ | n-Pr | 7-Cl | LC6: 3.48 min. (M + H) 585 |
| 140 | 4-CF$_3$ | n-Pr | 7,8-Cl | LC7: 3.49 min. (M + H) 603 |
| 141 | 4-Cl | —CH$_2$CH$_2$CF$_3$ | 7,8-Cl | LC6: 3.97 min. (M + H) 625 |
| 142 | 4-OCF$_3$ | n-Pr | 7,8-Cl | LC6: 4.06 min. (M + H) 619 |

TABLE 5

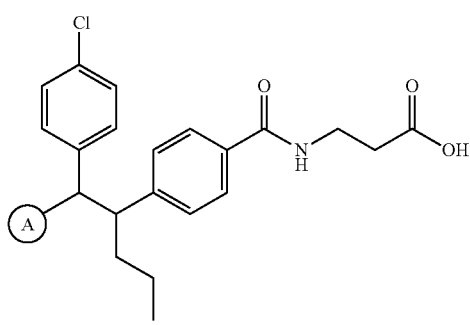

| EXAMPLE | A | enantiopurity | LC-MS data |
|---|---|---|---|
| 143 | | racemic | LC1 1.95 min. (M + H) 501 |

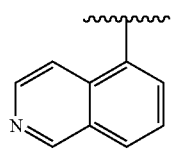 [SMILES: *c1cccc2cnccc12]

TABLE 5-continued

| EXAMPLE | A | enantiopurity | LC-MS data |
|---|---|---|---|
| 144 | 7-methoxyisoquinolin-3-yl | racemic | LC1 1.94 min. (M + H) 529 |
| 145 | 2-methoxy-1,8-naphthyridin-3-yl | racemic | LC1 2.02 min. (M + H) 532 |
| 146 | 2-methoxyquinolin-8-yl | enantiopure | LC1 2.41 min. (M + H) 531 |
| 147 | 7-methoxyquinolin-3-yl | enantiopure | LC1 1.86 min. (M + H) 531 |
| 148 | 7-chloroquinolin-3-yl | enantiopure | LC1 2.08 min. (M + H) 535 |
| 149 | 3-methoxyisoquinolin-7-yl | enantiopure | LC1 2.11 min. (M + H) 531 |
| 150 | 3-methoxyquinolin-7-yl | enantiopure | LC1 2.03 min. (M + H) 531 |
| 151 | 8-methoxy-2-methylquinolin-7-yl | enantiopure | LC1 1.88 min. (M + H) 545 |

TABLE 5-continued
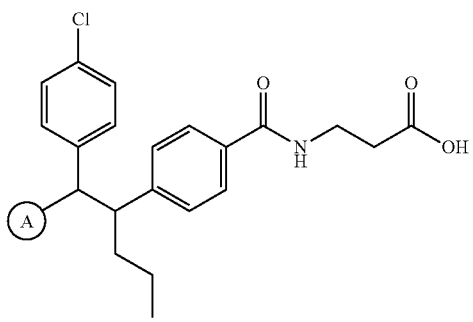
| EXAMPLE | A | enantiopurity | LC-MS data |
|---|---|---|---|
| 152 | 5-(1-methoxyisoquinolinyl) | enantiopure | LC4 2.45 min. (M + H) 531 |
| 153 | 5-(3-methoxy-1-methylisoquinolinyl) | enantiopure | LC6 3.31 min. (M + H) 545 |
| 154 | 5-(1,3-dimethoxyisoquinolinyl) | enantiopure | LC6 3.37 min. (M + H) 561 |
| 155 | 5-(1-methoxy-3-methylisoquinolinyl) | enantiopure | LC6 3.71 min. (M + H) 545 |
| 156 | 8-(3-methoxyisoquinolinyl) | enantiopure | LC6 3.91 min. (M + H) 531 |

Example 157

N-(4-{(1S)-1-[(4-Chlorophenyl)(6,7-Difluoroquinolin-4-Yl)Methyl]Butyl}Benzoyl)-β-alanine

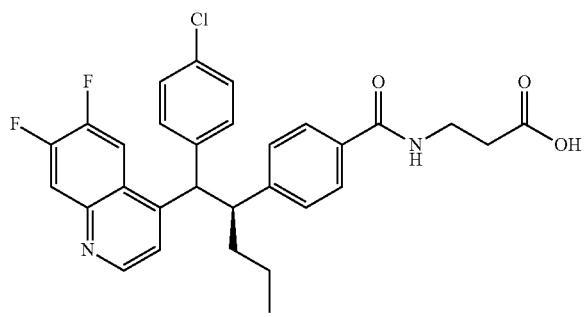 [SMILES: CCC[C@H](c1ccc(C(=O)NCCC(=O)O)cc1)C(c1ccc(Cl)cc1)c1ccnc2cc(F)c(F)cc12]

Step A. 6,7-Difluoroquinolin-4-ol and 5,6-Difluoroquinolin-4-ol

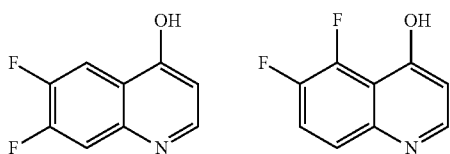 [SMILES: Oc1ccnc2cc(F)c(F)cc12 ; Oc1ccnc2ccc(F)c(F)c12]

Trimethyl orthoformate (40 mL, 362 mmol) and 2,2-dimethyl-1,3-dioxane-4,6-dione (6.24 g, 43.4 mmol) were refluxed for one hour, during which time the solution gradually became orange. The solution was cooled slightly, then 3,4-difluoroaniline (5.1 g, 39.5 mmol) in DMF (40 ml) was added. The mixture was refluxed for two hours, then cooled to room temperature and poured into 500 mL of cold water. The resulting off-white precipitate was collected by filtration, washed with water (2×100 mL), then dried in vacuo. The light orange material was suspended in EtOAc (50 mL), collected by filtration, and washed with EtOAc (2×30 mL). The resulting white solid was used directly for the next step. LC4: 1.60 min. (M+H) 284.

The solid from the previous step was dissolved in diphenyl ether (35 mL) and heated to 220-250° C. for 10-15 min. Gas evolution was observed and the solution turned dark brown. The mixture was allowed to cool then poured into hexanes (150 mL). The resulting light brown precipitate was collected by filtration and washed with hexanes (2×50 mL), then dried in vacuo to provide a mixture of the two title compounds in a 4:1 ratio. 6,7-Difluoroquinolin-4-ol: $^1$H NMR (500 MHz, d$_6$-Acetone): δ 10.80 (br, 1H); 7.96 (dd, J=11.0, 9.0 Hz, 1H); 7.89 (d, J=7.3 Hz, MX 7.51 (dd, J=11.2, 6.6 Hz, 1H); 6.05 (d, J=7.6, 1 H); LC4: 0.1-0.5 min. (M+H) 181. 5,6-Difluoroquinolin-4-ol: $^1$H NMR (500 MHz, d$_6$-Acetone): δ 10.80 (br, 1H); 7.79 (d, J=7.5 Hz, 1H); 7.58 (q, J=9.3 Hz, 1H); 7.41-7.37 (m, 1H); 5.97 (d, J=7.6, 1 H); LC4: 0.1-0.5 min. (M+H) 181.

Step B. 4-Bromo-6,7-difluoroquinoline and 4-Bromo-5,6-difluoroquinoline

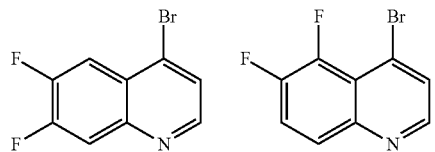

A suspension of 6,7-difluoroquinolin-4-ol and 5,6-difluoroquinolin-4-ol (4:1 ratio, 2.06 g, 11.3 mmol) and triphenylphosphine dibromide (7.50 g, 17.8 mmol) in CH$_3$CN (40 mL) was refluxed for 16 h. The mixture was cooled to room temperature then concentrated. The residue was dissolved in CH$_2$Cl$_2$ (100 mL) and washed with 1 M NaOH (aq) (100 mL). The aqueous phase was extracted with CH$_2$Cl$_2$ (50 mL). The combined organics were dried over Na$_2$SO$_4$, filtered, and concentrated. The residue was purified by silica gel chromatography eluting with 0-20% EtOAc/hexanes to afford the title compounds as white solids. 4-Bromo-6,7-difluoroquinoline: $^1$H NMR (500 MHz, CDCl$_3$): δ 8.65 (d, J=4.8 Hz, 1H); 7.97 (dd, J=11.0, 8.2 Hz, 1H); 7.88 (dd, J=10.7, 7.8 Hz, 1H); 7.70 (d, J=4.6 Hz, 1H); LC4: 1.46 min. (M+H) 244. 4-Bromo-5,6-difluoroquinoline: $^1$H NMR (500 MHz, CDCl$_3$): δ 8.62 (d, J=4.6 Hz, 1H); 7.95 (ddd, J=9.4, 4.6, 2.1 Hz, 1H); 7.75 (d, J=4.6 Hz, 1H); 7.63 (ddd, J=9.4, 9.4, 7.7 Hz, 1H); LC4: 1.46 min. (M+H) 244.

Step C. 4-Bromo-6,7-difluoro-8-(trimethylsilyl)quinoline

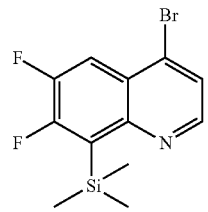 [SMILES: C[Si](C)(C)c1c(F)c(F)cc2c(Br)ccnc12]

Diisopropylamine (0.770 mL, 5.41 mmol) was added dropwise to nBuLi (2.3 M in hexanes, 2.14 mL, 4.92 mmol) in THF (25 mL) at −78° C. After stirring for 15 minutes, a solution of 4-bromo-6,7-difluoroquinoline (1.20 g, 4.92 mmol) in THF (25 mL) was added slowly via cannula. After stirring an additional 1.5 hours, chlorotrimethylsilane (0.690 mL, 5.40 mmol) was added dropwise. After stirring one additional hour, the solution was poured into saturated NH$_4$Cl (aq) (100 mL) then diluted with water (100 mL) and EtOAc (200 mL). The organic layer was separated, dried over Na$_2$SO$_4$, filtered, and concentrated. The residue was purified by silica gel chromatography eluting with 0-10% EtOAc/hexanes to afford the title compound as a light yellow solid: $^1$H NMR (500 MHz, CDCl$_3$): δ 8.60 (d, J=4.7 Hz, 1H); 7.93 (dd, J=10.8, 8.6 Hz, 1H); 7.64 (d, J=4.7 Hz, 1H); 0.49 (s, 9H); LC4: 2.86 min. (M+H) 316.

Step D. tert-Butyl 4-((1R)-1-{(4-chlorophenyl)[6,7-difluoro-8-(trimethylsilyl)quinolin-4-yl]hydroxymethyl}butyl)benzoate

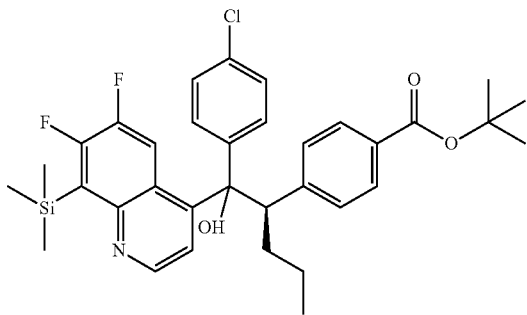 [SMILES: CCC[C@H](c1ccc(C(=O)OC(C)(C)C)cc1)C(O)(c1ccc(Cl)cc1)c1ccnc2c([Si](C)(C)C)c(F)c(F)cc12]

A solution of 4-bromo-6,7-difluoro-8-(trimethylsilyl)quinoline (213 mg, 0.674 mmol) in THF (1.5 mL) was added dropwise to a solution of nBuLi (2.3 Min. hexanes, 0.281 mL, 0.668 mmol) in THF (1.0 mL) at −78° C. After stirring for ten minutes, a solution of INTERMEDIATE 1 (150 mg, 0.402 mmol) in THF (1.5 mL) was added dropwise. After stirring an additional 15 minutes, the solution was poured into 1:1 water: saturated NH$_4$Cl (aq) (20 mL) and diluted with EtOAc (20 mL). The layers were separated, and the aqueouse layer was extracted with EtOAc (10 mL). The combined organics were dried over Na$_2$SO$_4$, filtered, and concentrated. The residue was purified by silica gel chromatography eluting with 0-12% EtOAc/hexanes to afford a single diastereomer of the title compound as a light yellow solid: $^1$H NMR (500 MHz, CDCl$_3$): δ 8.94 (d, J=4.6 Hz, 1H); 8.15 (t, J=10.8 Hz, 1H); 7.74 (d, J=−8.0 Hz, 2H); 7.59 (d, J=4.7 Hz, 1H); 7.10 (d, J=8.0 Hz, 2H); 6.96 (d, J=8.6 Hz, 2H); 6.93 (d, J=8.6 Hz, 2H); 3.67 (d, J=11.4 Hz, 1H); 2.79 (s, 1H); 2.06-1.98 (m, 1H); 1.97-1.88 (m, 1H); 1.58 (s, 9H); 1.41-1.27 (m, 1H); 1.30-1.18 (m, 1H); 0.88 (t, J=7.3 Hz, 3H); 0.48 (s, 9H); LC4: 2.99 min (M+H) 610.

Step E. tert-Butyl 4-((1S)-1-{(4-chlorophenyl)[6,7-difluoro-8-(trimethylsilyl)quinolin-4-yl]methyl}butyl)benzoate

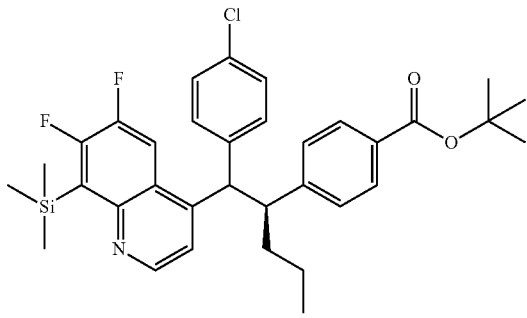 [SMILES: CCC[C@H](c1ccc(C(=O)OC(C)(C)C)cc1)C(c1ccc(Cl)cc1)c1ccnc2c([Si](C)(C)C)c(F)c(F)cc12]

A solution of LHMDS in THF (1.0 M, 0.628 mL, 0.628 mmol) was added dropwise to a solution of tert-butyl 4-((1R)-1-{(4-chlorophenyl)[6,7-difluoro-8-(trimethylsilyl)quino-lin-4-yl]hydroxymethyl}butyl)benzoate (191.7 mg, 0.314 mmol) in THF (3.1 mL) at −78° C. After stirring for ten minutes, methyl oxalylchloride (0.087 mL, 0.942 mmol) was added dropwise. After stirring an additional ten minutes, the solution was poured into water (12 mL) and diluted with EtOAc (12 mL). The layers were separated, and the organic layer was washed with water (3×10 mL). The organic layer was dried over Na$_2$SO$_4$, filtered, and concentrated. The resulting colorless oil was used directly for the following step. LC4: 3.32 min. (M+H) 696.

The residue from the previous step was azeotroped from toluene and dried in vacuo. It was then dissolved in toluene (4.5 mL) then AIBN (51.7 mg, 0.315 mmol) and nBu$_3$SnH (0.252 mL, 0.944 mmol) were added. The apparatus was evacuated and refilled with dry nitrogen three times. The mixture was then placed in an oil bath at 100° C. After stirring for one hour, the solution was cooled to room temperature then concentrated. The residue was purified by silica gel chromatography eluting with 0-10% EtOAc/hexanes to afford a mixture of the title compounds as a colorless oil (1:1.2 d.r.).

Major isomer: $^1$H NMR (500 MHz, CDCl$_3$): δ 8.90 (d, J=4.6 Hz, 1H); 7.87 (dd, J=11.9, 8.6 Hz, 1H); 7.83 (d, J=7.7 Hz, 2H); 7.56 (d, J=4.7 Hz, 1H); 7.34 (d, J=8.3 Hz, 2H); 7.28 (d, J=8.4 Hz, 2H); 7.22 (d, J=8.1 Hz, 2H); 7.18 (d, J=7.9 Hz, 2H); 6.99 (d, J=8.7 Hz, 2H); 6.96 (d, J=8.7 Hz, 2H); 4.70 (d, J=11.4 Hz, 1H); 3.58-3.52 (m, 1H); 1.52 (s, 9H); 1.39-1.25 (m, 2H); 1.08-0.98 (m, 2H); 0.73 (t, J=7.3 Hz, 3H); 0.49 (s, 9H); LC4: 3.13 min. (M+H) 594.

Minor isomer: $^1$H NMR (500 MHz, CDCl$_3$): δ 8.62 (d, J=4.6 Hz, 1H); 7.80 (dd, =11.6, 8.4 Hz, 1H); 7.76 (d, J=8.0 Hz, 2H); 7.38 (d, J=4.6 Hz, 1H); 7.34 (d, J=8.3 Hz, 2H); 7.28 (d, J=8.4 Hz, 2H); 7.22 (d, J=8.1 Hz, 2H); 4.81 (d, J=11.3 Hz, 1H); 3.58-3.52 (m, 1H); 1.58 (s, 9H); 1.39-1.25 (m, 2H); 1.08-0.98 (m, 2H); 0.73 (t, J=7.3 Hz, 3H); 0.39 (s, 9H); LC4: 3.13 min. (M+H) 594.

Step F. tert-Butyl 4-((1S)-1-{(4-chlorophenyl)[6,7-difluoroquinolin-4-yl]methyl}butyl)benzoate

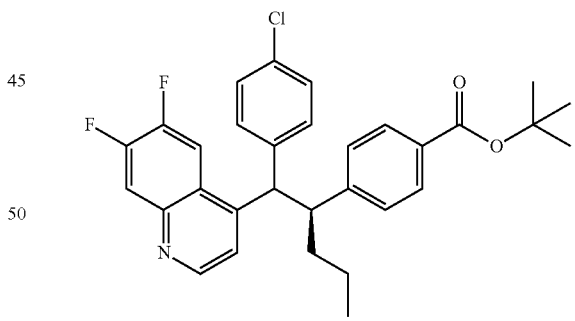

A solution of TBAF in THF (1.0 M, 0.39 mL, 0.39 mmol) was added to a solution of tert-butyl 4-((1S)-1-{(4-chlorophenyl)[6,7-difluoro-8-(trimethylsilyl)quinolin-4-yl]methyl}butypbenzoate (1:1.2 d.r., 116.5 mg, 0.196 mmol) in THF (2.8 mL). After stirring at room temperature for one hour, the solution was concentrated. The residue was purified by silica gel chromatography eluting with 10-50% EtOAc/hexanes to afford a mixture of the title compounds as a colorless oil (1:1.2 d.r.).

Major isomer: $^1$H NMR (500 MHz, CDCl$_3$): δ 8.95 (d, J=4.7 Hz, 1H); 7.91 (dd, J=11.6, 8.1 Hz, 1H); 7.89-7.81 (m, 1H); 7.84 (d, J=7.8 Hz, 2H); 7.62 (d, J=4.7 Hz, 1H); 7.18 (d, J=7.8 Hz, 2H); 7.00 (d, J=8.4 Hz, 2H); 6.96 (d, J=8.5 Hz, 2H); 4.72 (d, =11.3 Hz, 1H); 3.59-3.51 (m, 1H); 1.64-1.47 (m, 2H); 1.58 (s, 9H); 1.08-1.00 (m, 2H); 0.72 (t, J=5.2 Hz, 3H); LC4: 2.52 min. (M+H) 522.

Minor isomer: $^1$H NMR (500 MHz, CDCl$_3$): δ 8.68 (d, J=4.7 Hz, 1H); 7.89-7.81 (m, 1H); 7.73 (d, J=8.0 Hz, 2H); 7.70 (dd, J=11.0, 8.0 Hz, 1H); 7.43 (d, J=4.8 Hz, 1H); 7.36 (d, J=8.3 Hz, 2H); 7.30 (d, J=8.3 Hz, 2H); 7.20 (d, J=7.7 Hz, 2H); 4.81 (d, J=11.3 Hz, 1H); 3.59-3.51 (m, 1H); 1.64-1.47 (m, 2H); 1.51 (s, 9H); 1.08-1.00 (m, 2H); 0.75 (t, J=5.3 Hz, 3H); 0.72 (t, J=5.2 Hz, 3H); LC4: 2.52 min. (M+H) 522.

Step G. tert-Butyl N-(4-{(1S)-1-[(4-chlorophenyl)(6,7-difluoroquinolin-4-yl)methyl]butyl}benzoyl)-β-alaninate

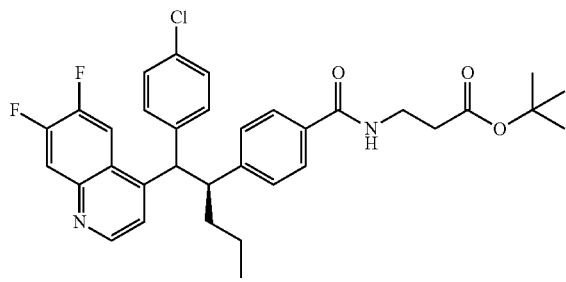 [SMILES: CCC[C@H](c1ccc(C(=O)NCCC(=O)OC(C)(C)C)cc1)C(c1ccc(Cl)cc1)c1ccnc2cc(F)c(F)cc12]

To a solution of tert-butyl 4-((1S)-1-{(4-chlorophenyl)[6,7-difluoroquinolin-4-yl]methyl}butyl)benzoate (1:1.2 d.r., 75 mg, 0.144 mmol) in CH$_2$Cl$_2$ (2.0 mL) was added TFA (1.0 mL). After stirring at room temperature overnight, the solution was concentrated. The residue was diluted with CH$_2$Cl$_2$ (5 mL) and concentrated again. The resulting light orange foam was used directly for the following step. LC5: 1.24 min. (M+H)=466.

The residue from the previous step was dissolved in CH$_2$Cl$_2$ (2.0 mL) then t-butyl β-alaninate hydrochloride (52.2 mg, 0.287 mmol), iPr$_2$NEt (0.502 mL, 2.87 mmol) and BOP (127 mg, 0.287 mmol) were added. After stirring at room temperature for 30 minutes, the solution was washed with 0.5 M HCl (aq) (2×2 mL) then 1 M NaOH (aq) (2 mL). The individual aqueous layers were extracted with CH$_2$Cl$_2$ (2 mL). The combined organics were dried over Na$_2$SO$_4$, filtered, and concentrated. The residue was purified by silica gel chromatography eluting with 15-70% EtOAc/hexanes to afford the title compounds as colorless oils.

Major isomer (faster-eluting on silica gel): $^1$H NMR (500 MHz, CDCl$_3$): δ 8.95 (d, J=4.7 Hz, 1H); 7.90 (dd, J=10.2, 6.0 Hz, 1H); 7.86 (dd, J=9.4, 5.8 Hz, 1H); 7.64-7.60 (m, 3H); 7.19 (d, J=8.0 Hz, 2H); 6.98 (d, J=8.5 Hz, 2H); 6.94 (d, J=8.5 Hz, 2H); 6.81 (t, 3-6.0 Hz, 1H); 4.69 (d, J=11.3 Hz, 1H); 3.67 (q, J=5.9 Hz, 2H); 3.54 (td, J=11.2, 3.2 Hz, 1H); 2.55 (t, J=5.9 Hz, 2H); 1.66 (t, 36.2 Hz, 2H); 1.47 (s, 9H); 1.06 (h, J=7.5 Hz, 2H); 0.73 (t, J=7.3 Hz, 3H): LC4: 2.60 min. (M+H) 593.

Minor isomer (slower-eluting on silica gel): $^1$H NMR (500 MHz, CDCl$_3$): δ 8.68 (d, J=4.7 Hz, 1H); 7.83 (dd, J=11.9, 8.2 Hz, 1H); 7.69 (dd, J=11.0, 8.0 Hz, 1H); 7.51 (d, =8.0 Hz, 2H); 7.42 (d, J=4.8 Hz, 1H); 7.35 (d, 3-8.4 Hz, 2H); 7.30 (d, J=8.4 Hz, 2H); 7.21 (d, J=8.1 Hz, 2H); 6.69 (t, J=5.9 Hz, 1H); 4.81 (d, J=11.3 Hz, 1H); 3.59 (q, J=5.9 Hz, 2H); 3.55 (td, J=10.9, 3.4 Hz, 1H); 2.48 (t, J=5.8 Hz, 2H); 1.59-1.46 (m, 2H); 1.43 (s, 9H); 1.08-0.98 (m, 2H); 0.75 (t, 37.3 Hz, 3H); LC4: 2.64 min. (M+H) 593.

Step H. N-(4-{(1S)-1-[(4-Chlorophenyl)(6,7-difluoroquinolin-4-yl)methyl]butyl}benzoyl)-β-alanine

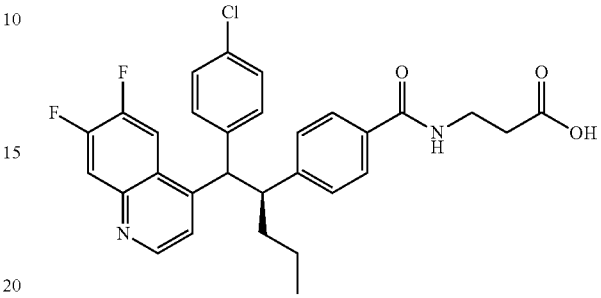

A solution of the slower-eluting isomer of tert-butyl N-(4-{(1S)-1-[(4-chlorophenyl)(6,7-difluoroquinolin-4-yl)methyl]butyl}benzoyl)-β-alaninate from Step G (34 mg, 0.058 mmol) in CH$_2$Cl$_2$ (2.0 mL) was treated with TFA (1.0 mL). After stirring at room temperature overnight, the solution was concentrated. The residue was purified by preparative reverse phase HPLC, eluting with acetonitrile/water+0.1% formic acid. Following lyophilization, this afforded the title compound as a fluffy, white solid: $^1$H NMR (500 MHz, CDCl$_3$): δ 8.95 (s, 1H); 8.10-8.01 (m, 2H); 7.85 (d, J=5.0 Hz, 1H); 7.53 (d, J=7.8 Hz, 2H); 7.38 (d, J=8.4 Hz, 2H); 7.34 (d, J=8.4 Hz, 2H); 7.21 (d, J=7.8 Hz, 2H); 6.97 (s, 1H); 4.93 (d, J=11.4 Hz, 1H); 3.65-3.54 (m, 3H); 2.56 (t, J=5.5 Hz, 2H); 1.65-1.53 (m, 2H); 1.13-0.97 (m, 2H); 0.75 (t, J=7.2 Hz, 3H); LC4: 2.26 min. (M+H) 537.

The compounds in TABLE 6 were prepared using the procedures described for INTERMEDIATE 1 and EXAMPLE 157. All compounds were prepared as enantiopure compounds, and the data provided is for the most active stereoisomer.

TABLE 6

| EXAMPLE | R$^1$ | R$^2$ | R$^3$ | LC-MS data |
|---|---|---|---|---|
| 158 | 4-CF$_3$ | n-Pr | 6,7-diF | LC4: 2.34 min. (M + H) 587 |
| 159 | 3-Cl | n-Pr | 6,7-diF | LC4: 1.95 min. (M + H) 537 |
| 160 | 4-Me | n-Pr | 6,7-diF | LC4: 1.90 min. (M + H) 517 |
| 161 | 4-F | n-Pr | 6,7-diF | LC4: 2.14 min. (M + H) 521 |
| 162 | 3,5-diCl | n-Pr | 6,7-diF | LC4: 2.41 min. (M + H) 571 |
| 163 | 4-Cl | Me | 6,7-diF | LC4: 2.10 min. (M + H) 509 |
| 164 | 4-Cl | Et | 6,7-diF | LC4: 2.17 min. (M + H) 523 |

TABLE 6-continued

[Structure with R1, R2, R3 substituents on quinoline-phenyl-benzamide-β-alanine scaffold]

| EXAMPLE | R¹ | R² | R³ | LC-MS data |
|---|---|---|---|---|
| 165 | 4-Cl | —CH₂CH₂CF₃ | 6,7-diF | LC4: 2.25 min. (M + H) 591 |
| 166 | 4-CF₃ | Et | 6,7-diF | LC4: 2.22 min. (M + H) 557 |
| 167 | 4-Cl | n-Pr | 6-CF₃, 7-F | LC4: 2.43 min. (M + H) 587 |
| 168 | 4-Cl | —CH₂CH₂CF₃ | 6-Cl, 7-F | LC4: 2.32 min. (M + H) 607 |

Example 169

N-[4-((1S)-1-{(4-Chlorophenyl)[2-(Difluoromethoxy)Quinolin-5-Yl]Methyl}Butyl)Benzoyl]-β-Alanine

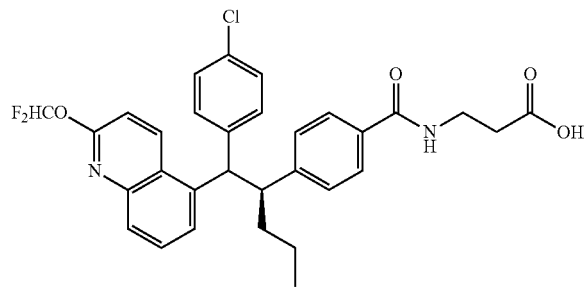 [SMILES: CCC[C@H](c1ccc(C(=O)NCCC(=O)O)cc1)C(c1ccc(Cl)cc1)c1cccc2nc(OC(F)F)ccc12]

Step A. 4-((1S)-1-{(4-chlorophenyl)[2-(difluoromethoxy)quinolin-5-yl]methyl}butyl)benzoic acid

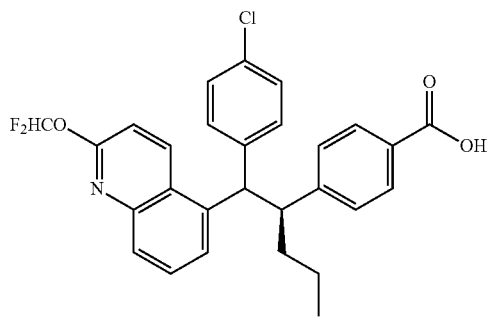 [SMILES: CCC[C@H](c1ccc(C(=O)O)cc1)C(c1ccc(Cl)cc1)c1cccc2nc(OC(F)F)ccc12]

A solution of 4-{(1S)-1-[(4-chlorophenyl)(2-methoxyquinolin-5-yl)methyl]butyl}benzoic acid (EXAMPLE 2, Step B, 750 mg, 1.6 mmol) and iodotrimethylsilane (1.63 g, 8.2 mmol) in CH₂Cl₂ (40 mL) was heated at 50° C. for 18 hours. The reaction mixture was allowed to cool to room temperature then diluted with CH₂Cl₂ (40 mL). The solution was washed with sodium sulfide (aq) then saturated NaCl (aq), dried over Na₂SO₄, filtered, then concentrated. The resulting material was used directly for the following step. LC2: 1.14 and 1.18 min. (M+H) 446.

The residue from the previous step was dissolved in N-methylpyrollidine (2 mL) and water (0.5 mL). Potassium carbonate (110 mg, 4.89 mmol) and sodium chlorodifluoroacetate (100 mg, 4.1 mmol) were added. The reaction vessel was purged with nitrogen then heated at 140° C. in a microwave reactor for 45 min. The mixture was diluted with EtOAc (20 mL), washed with saturated NaCl (aq), dried over Na₂SO₄, filtered, then concentrated. The residue was subjected to the same conditions a second time. Following concentration, the mixture was purified by reverse-phase HPLC eluting with 30-100% acetonitrile/water+0.1% TFA. Following lyophilization, this afforded the title compound as a mixture of diastereomers. LC2: 1.17 and 1.12 min. (M+H) 496.

Step B. N-[4-((1S)-1-{(4-chlorophenyl)[2-(difluoromethoxy)quinolin-5-yl]methyl}butyl)benzoyl]-β-alanine Using the procedures from EXAMPLE 2 Step C, 4-((1S)-1-{(4-chlorophenyl)[2-(difluoromethoxy)quinolin-5-yl]methyl}butyl)benzoic acid was converted to the title compound: Slower-eluting diastereomer by reverse-phase HPLC (more active diastereomer): $^1$H NMR (500 MHz, CDC10: δ 8.51 (d, J=9.5 Hz, 1H), 7.62-7.51 (m, 3H), 7.47 (d, J=8.0 Hz, 2H), 7.38 (d, J=8.5 Hz, 2H), 7.30 (d, J=8.5 Hz, 2H), 7.24 (d, J=8.0 Hz, 2H), 6.99 (d, J=9.0 Hz, 1H), 6.79 (t, J=6.0 Hz, 1H), 4.91 (d, J=11.5 Hz, 1H), 3.68-3.59 (m, 3H), 2.67 (t, J=6.0 Hz, 2H), 1.66-1.64 (m, 1H), 1.56-1.53 (m, 1H), 1.08-1.03 (m, 2H), 0.78 (t, J=7.0 Hz, 3H); LC2: 1.22 min. (M+H) 567.

Example 170

N-(4-{(1S)-1-[(4-Chlorophenyl)(2-(1H-Pyrol-2-Yl) Quinolin-5-Yl)Methyl]Butyl}Benzoyl)-β-Alanine

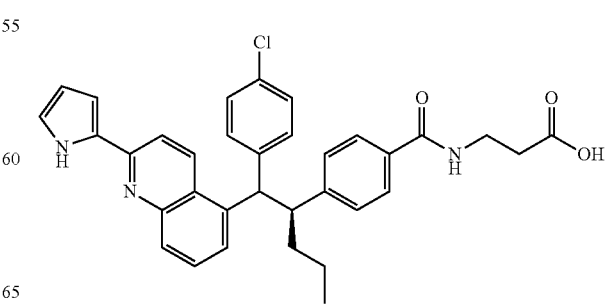

Step A. Ethyl N-(4-{(1S)-1-[(4-chlorophenyl)(2-chloroquinolin-5-yl)methyl]butyl}benzoyl)-β-alaninate

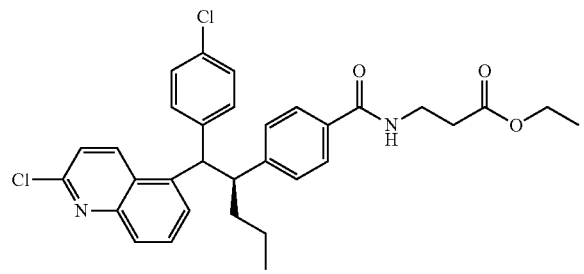 [SMILES: CCC[C@H](c1ccc(C(=O)NCCC(=O)OCC)cc1)C(c1ccc(Cl)cc1)c1cccc2nc(Cl)ccc12]

Using the procedures from EXAMPLE 2 Steps A-C, 5-bromo-3-chloroquinoline was converted to the title compound: LC3: 3.08 min. (M+H) 563.

Step B. N-(4-{1-[(4-chlorophenyl)-(2-(1H pyrazol-5-yl)quinolin-5-yl)methyl]butyl}benzoyl)-β-alanine

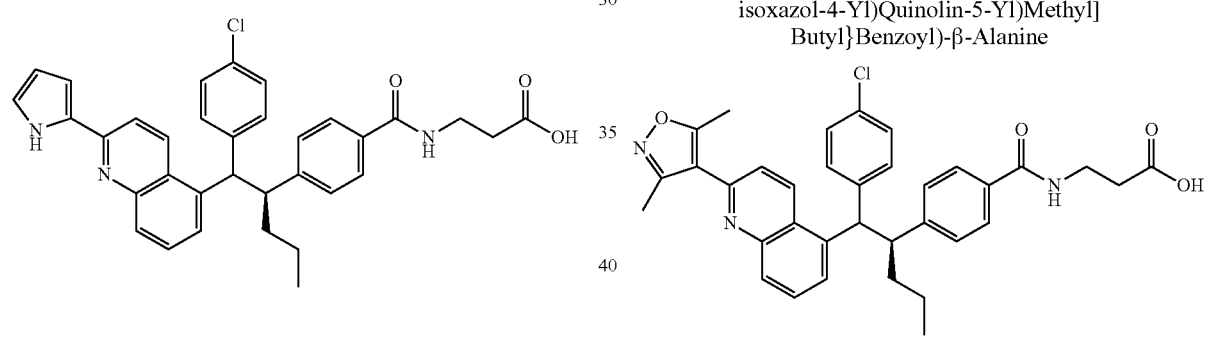

The product of Step A (50 mg, 0.089 mmol) was mixed with 1H-pyrole-2-boronic acid (10.9 mg, 0.098 mmol), tetrakis(triphenylphosphine)palladium(0) (10.2 mg, 0.009 mmol), and sodium bicarbonate (2.0 M in water, 0.098 mL, 0.195 mmol) in THF (10 mL). The resulting mixture was stirred in a microwave reactor at 150° C. for 1 hour, then treated with acetic acid (0.10 mL). The mixture was purified by preparative reverse phase HPLC, eluting with 10-90% acetonitrile/water+0.1% formic acid. Following lyophilization, this afforded the two diastereomers of the title compound as white solids.

Faster-eluting diastereomer: $^1$H NMR (500 MHz, CDCl$_3$): δ 9.39 (d, 39.5 Hz, 1H); 8.16-8.19 (m, 2H); 8.04-8.09 (m, 2H); 7.59-7.64 (m, 4H); 7.37-7.41 (m, 5H); 7.17-7.32 (m, 3H); 6.98 (d, J=8.4 Hz, 1H); 5.13 (d, J=11.6 Hz, 1H); 3.81 (bt, 1H); 3.59 (m, 2H); 2.60 (m, 2H); 1.59-1.67 (m, 2H), 1.01-1.13 (m, 2H); 0.71 (t, J=7.3 Hz, 3H); LC3: 2.50 min. (M+H) 566.

Slower-eluting diastereomer (more active diastereomer): $^1$H NMR (500 MHz, CDCl$_3$): δ 9.32 (d, 9.3 Hz, 1H); 8.02-8.07 (m, 2H); 7.68-7.80 (m, 2H); 7.63-7.65 (m, 5H); 7.49-7.52 (m, 4H); 7.32-7.39 (m, 4H); 6.50 (s, 1H); 5.24 (d, J=11.5 Hz, 1H); 3.80 (m, 1H); 3.48 (t, J=6.8 Hz, 2H); 2.50 (t, J=6.8 Hz, 2H); 1.61-1.68 (m, 2H), 1.01-1.09 (m, 2H); 0.76 (t, J=7.5 Hz, 3H); LC3: 2.44 min. (M+H) 566.

Example 171

N-(4-{(1S)-1-[(4-Chlorophenyl)(2-(1H-Pyrazol-5-Yl)Quinolin-5-Yl)Methyl]Butyl}Benzoyl)-β-Alanine

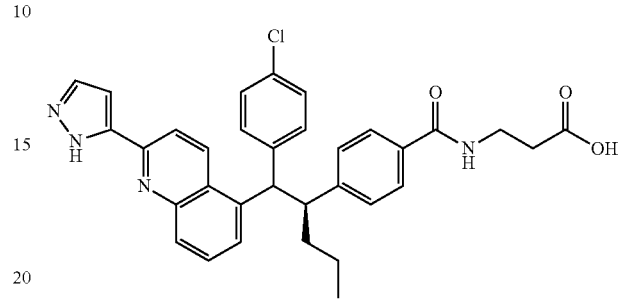

Using the procedures from EXAMPLE 170 Step B, 1H-pyrazole-5-boronic acid was converted to the title compound: LC3: 2.22 min. (M+H) 567.

Example 172

N-(4-{(1S)-1-[(4-Chlorophenyl)(2-(3,5-Dimethyl-isoxazol-4-Yl)Quinolin-5-Yl)Methyl]Butyl}Benzoyl)-β-Alanine

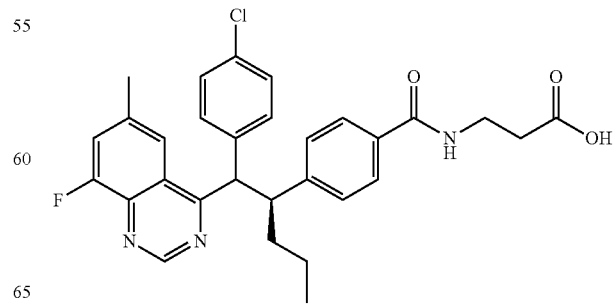

Using the procedures from EXAMPLE 170 Step B, 3,5-dimethylisoxazole-4-boronic acid was converted to the title compound: LC3: 2.47 min. (M+H) 596.

Example 173

N-(4-{(1S)-1-[(R)-(4-Chlorophenyl)(8-Fluoro-6-Methylquinazolin-4-Yl)Methyl]Butyl}Benzoyl)-β-Alanine

Step A. N-(4-{(1S)-1-[2-(2-amino-3-fluoro-5-methylphenyl)-1-(4-chlorophenyl)-2-oxoethyl]butyl}benzoyl)-β-alanine

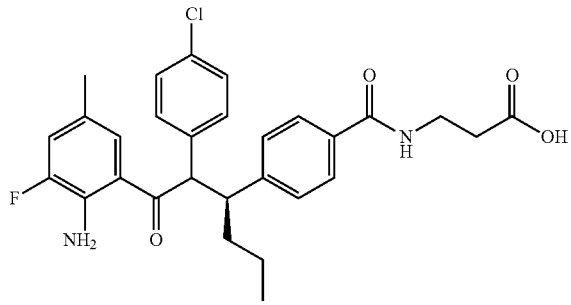

N-(4-{(1S)-1-[(R)-(4-chlorophenyl)-(7-fluoro-5-methyl-1H-indol-4-yl)methyl]butyl}benzoyl)-β-alanine (455 mg, 0.87 mmol) was dissolved in methanol (100 mL) and cooled to −78° C. Ozone was bubbled through the solution until the blue color of ozone was observed. Nitrogen was then bubbled through the solution until the blue color of ozone dissipated. Dimethyl sulfide (1.3 mL, 17 mmol) was added, and the mixture was stirred at room temperature overnight, then concentrated. The resulting yellow solid was dissolved in EtOAc, washed with water then saturated NaCl (aq), dried over MgSO$_4$, filtered, then concentrated. NMR and LC/MS analysis showed it was a mixture (1:3) of the title compound and the aniline-N-formylated title compound. This mixture was used for the next step without purification. Title compound: LC1: 2.27 min. (M+H) 525. Formylated compound: LC I: 2.09 min. (M+H) 553.

The mixture of products from the previous step (335 mg, 0.606 mmol) was refluxed in THF (20 mL) with HCl (10% in water, 3.0 mL, 9.9 mmol) for one hour. After being allowed to cool to room temperature, the mixture was diluted with saturated NH$_4$Cl (aq) then extracted with EtOAc. The organic phase was washed with saturated NaCl (aq), dried over MgSO$_4$, filtered, then concentrated. This afforded the title compound as a solid which was used for the next step without purification. LC1: 2.27 min. (M+H) 525.

Step B. N-(4-{(1S)-1-[(R)-(4-chlorophenyl)(8-fluoro-6-methylquinazolin-4-yl)methyl]butyl}benzoyl)-β-alanine

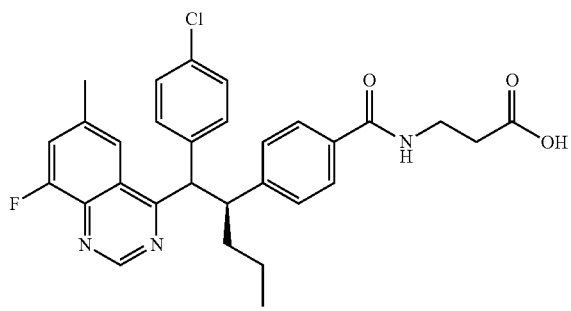 [SMILES: CCC[C@H](c1ccc(C(=O)NCCC(=O)O)cc1)C(c1ccc(Cl)cc1)c1ncnc2c(F)cc(C)cc12]

The product of the previous step (20 mg, 0.04 mmol) was dissolved in 0.3 mL of formamide and boron trifluoride diethyletherate (0.03 mL, 0.24 mmol) was added. The mixture was heated in a microwave synthesizer at 175° C. for 20 minutes. The mixture was purified by reverse-phase HPLC eluting with 5-75% acetonitrile/water+0.1% TFA. Following lyophilization, this afforded the title compound as a white solid. Slower-eluting diastereomer (more active diastereomer): $^1$H NMR (600 MHz, CDCl$_3$): δ 9.25 (s, 1H); 7.68 (s, 1H); 7.57 (d, J=8.1 Hz, 2H); 7.47 (d, J=7.9 Hz, 2H); 7.30 (t, J=8.7 Hz, 6H); 6.76-6.72 (m, 1H); 5.04 (d, J=11.1 Hz, 1H); 4.05-3.99 (m, 1H); 3.72-3.57 (m, 2H); 2.65 (t, J=6.5 Hz, 4H); 2.55 (s, 3H); 1.59-1.46 (m, 2H); 1.07-0.97 (m, 2H); 0.75 (t, J=7.3 Hz, 3H).

Example 174

N-(4-{1-[(4-Chlorophenyl)(4-Ethyl-6-Methoxyquinazolin-2-Yl)Methyl]Butyl}Benzoyl)-β-Alanine

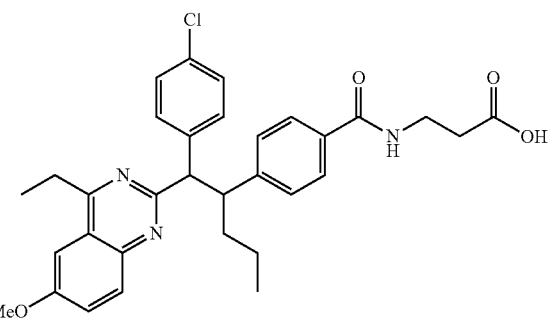

Step A. tert-Butyl 4-chlorophenylacetate

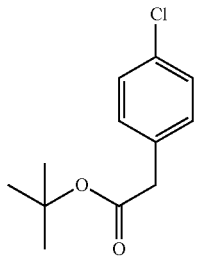

To a solution of 4-chlorophenylacetic acid (10.0 g, 58.6 mmol) in CH$_2$Cl$_2$ was added 2-Cert-butyl-1,3-diisopropylisourea (50 g, 250 mmol) dropwise at −10° C. The mixture was stirred at room temperature overnight, then the precipitate was, removed by filtration. The filtrate was washed with 1M HCl (aq) and saturated NaCl (aq), dried over Na$_2$SO$_4$, filtered, and concentrated. The residue was purified by silica gel chromatography eluting with 2% EtOAc/petroleum ether to afford the title compound: $^1$H NMR (CD$_3$OD, 300 MHz) δ 7.26-7.30 (m, 2H), 7.18-7.21 (m, 2H), 3.49 (s, 2H), 1.43 (s, 9H).

Step B. Methyl 4-{1-[2-tert-butoxy-1-(4-chlorophenyl)-2-oxoethyl]butyl}benzoate

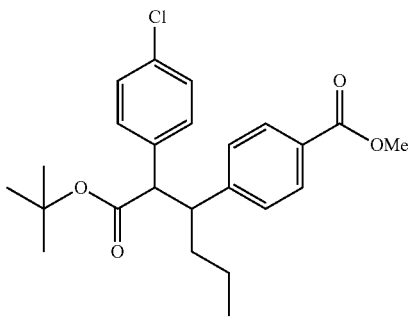 [SMILES: CCCC(c1ccc(C(=O)OC)cc1)C(C(=O)OC(C)(C)C)c1ccc(Cl)cc1]

The product of Step A (1.80 g, 7.94 mmol) was added to a suspension of KOtBu (980 mg, 8.73 mmol) in anhydrous DMF (15 mL) at 0° C. After stirring for two minutes, a solution of methyl 4-(1-bromobutyl)benzoate in DMF (5 mL) was added dropwise. The mixture was allowed to warm to room temperature. After stirring for 20 minutes, water was added then the solution was extracted with $CH_2Cl_2$ (2×100 mL). The combined organic layers were washed with saturated $NH_4Cl$ (aq) (20 mL) then saturated NaCl (aq) (20 mL), dried over $Na_2SO_4$, filtered, then concentrated. The residue was purified by silica gel chromatography eluting with 2% EtOAc/petroleum ether to afford the title compound: $^1$H NMR ($CD_3OD$, 300 MHz) δ 7.98-8.02 (m, 2H), 7.77-7.81 (m, 2H), 7.38-7.44 (m, 2H), 7.09-7.13 (m, 2H), 3.91 (s, 3H), 3.79-3.81 (m, 1H), 3.34-3.40 (m, 1H), 1.20-1.30 (m, 2H), 1.03 (s, 9H), 0.91-1.02 (m, 2H), 0.68 (t, J=7.4 Hz, 3H).

Step C. Methyl 4-(1-{1-(4-chlorophenyl)-2-[(4-methoxyphenyl)amino]-2-oxoethyl}butyl)benzoate

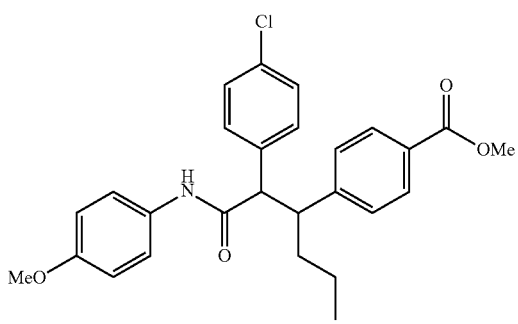 [SMILES: CCCC(c1ccc(C(=O)OC)cc1)C(C(=O)Nc1ccc(OC)cc1)c1ccc(Cl)cc1]

To a solution of the product from Step B (17 g, 40 mmol) in $CH_2Cl_2$ (100 mL) was added TFA (100 mL). After stirring overnight at room temperature, the solution was concentrated. The residue was dissolved in $CH_2Cl_2$ (40 mL), then hexanes (200 mL) was added slowly to the stirring $CH_2Cl_2$ solution. The resulting white precipitate was collected by filtration, washed with hexanes, then dried in vacuo to afford the title compound as a white solid: $^1$H NMR ($CD_3OD$, 300 MHz) δ 7.86-7.88 (m, 2H), 7.20-7.23 (m, 2H), 6.90-6.96 (m, 4H), 3.81 (s, 3H), 3.67 (d, J=11.2 Hz, 1H), 3.15-3.25 (m, 1H), 1.19-1.29 (m, 2H), 0.78-0.88 (m, 2H), 0.58 (t, J=7.0 Hz, 3H).

To a solution of the product from the previous step (3.00 g, 8.33 mmol) in DMF (20 mL) was added p-anisidine (1.50 g, 8.33 mmol), PyBOP (6.50 g, 12.5 mmol) and DMAP (3.05 g, 25.0 mmol). After stirring at room temperature overnight, the solution was poured into ice water (150 mL) then extracted with EtOAc (3×50 mL). The combined organic layers were washed with water (200 mL) then saturated NaCl (aq) (100 mL), dried over $Na_2SO_4$, filtered, then concentrated. The residue was purified by silica gel chromatography eluting with 15% EtOAc/petroleum ether to afford the title compound. Major isomer $^1$H NMR ($CD_3OD$, 400 MHz) δ 7.92-7.95 (m, 2H), 7.52-7.54 (m, 2H), 7.44-7.46 (m, 2H), 7.36-7.38 (m, 2H), 6.92-6.95 (m, 2H), 6.66-6.68 (m, 2H), 3.85 (s, 3H), 3.83-3.84 (m, 1H), 3.66 (s, 3H), 3.42-3.47 (m, 1H), 1.25-1.33 (m, 1H), 1.05-1.15 (m, 1H), 0.91-1.02 (m, 2H), 0.69 (t, J=7.4 Hz, 3H). MS 466 (M+H).

Step D. Methyl 4-{(1-[(4-chlorophenyl)(4-ethyl-6-methoxyquinazolin-2-yl)methyl]butyl}benzoate

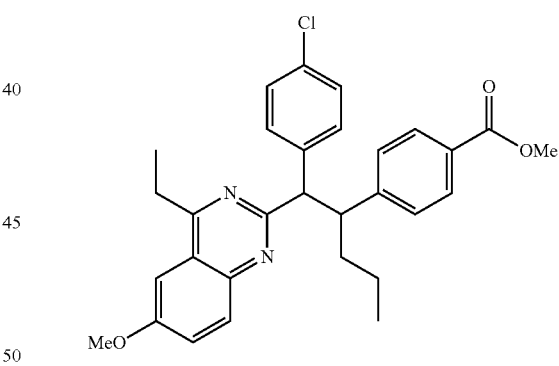

To a solution of the product of Step C (600 mg, 1.29 mmol) and 2-chloropyridine (175 mg, 1.54 mmol) in $CH_2Cl_2$ (6 mL) at −78° C. was added trifluoromethanesulfonic anhydride (400 mg, 1.42 mmol) dropwise over one minute. After stirring for five minutes, the reaction mixture was placed in an ice water bath and warmed to 0° C. Propionitrile (80 mg, 1.45 mmol) was added dropwise, then the solution was allowed to warm to room temperature. After stirring for 5 minutes, the solution was heated at 140° C. for 30 minutes in a microwave reactor. The mixture was poured into 1 M $Na_2CO_3$ (aq) (5 mL), then extracted with EtOAc (25 mL). The organic layer was washed with saturated NaCl (aq) (5 mL), dried over $Na_2SO_4$, filtered, then concentrated. The residue was purified by preparative TLC to afford the title compound as a mixture of diastereomers. MS 503 (M+H).

Step E. Ethyl N-(4-{1-[(4-chlorophenyl)(4-ethyl-6-methoxyquinazolin-2-yl)methyl]butyl}benzoyl)-β-alaninate

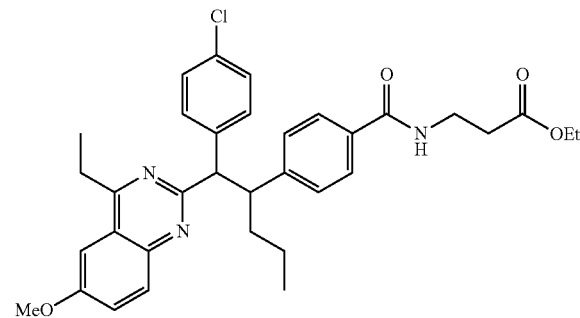 [SMILES: CCCC(c1ccc(C(=O)NCCC(=O)OCC)cc1)C(c1ccc(Cl)cc1)c1nc(CC)c2cc(OC)ccc2n1]

To the product of Step D (240 mg, 0.47 mmol) in MeOH (20 mL) was added NaOH (0.5 M in water, 5 mL, 2.5 mmol). After stirring at room temperature for 16 hours, the solution was concentrated. The mixture was then diluted with EtOAc and water, and the layers were separated. The aqueous layer was then acidified to pH 4 with 3 M AcOH (aq) then extracted twice with EtOAc. The organic layer was washed with saturated NaCl (aq), dried over $Na_2SO_4$, filtered, then concentrated. The resulting material was used directly for the next step.

The residue from the previous step was dissolved in $CH_2Cl_2$ (4 mL) then ethyl β-alaninate hydrochloride (103 mg, 0.564 mmol), HOBt (103 mg, 0.705 mmol), EDC (136 mg, 0.705 mmol), and $iPr_2NEt$ (0.410 mL, 2.35 mmol) were added. After stirring at room temperature overnight, the solution was concentrated. The residue was purified, and the two diastereomers were separated, by preparative TLC.

Faster-eluting diastereomer: $^1$H NMR ($CDCl_3$, 400 MHz), δ 7.68-7.75 (m, 3H), 7.46 (s, 1H), 7.44 (s, 1H), 7.27-7.36 (m, 4H), 7.06 (d, J=2.8 Hz, 1H), 6.68 (t, J=6.0 Hz, 1H), 4.50 (d, J=11.6 Hz, 1H), 4.11 (q, J=7.2 Hz, 2H), 3.84-3.92 (m, 4H), 3.58-3.64 (m, 2H), 3.07-3.16 (m, 2H), 2.54 (t, J=6.0 Hz, 2H), 1.48-1.52 (m, 2H), 1.39 (t, J=7.2 Hz, 2H), 1.22 (t, J=7.2 Hz, 2H), 0.92-1.05 (m, 2H), 0.69 (t, j=7.2 Hz, 3H). MS 587 (M+H).

Slower-eluting diastereomer: $^1$H NMR ($CDCl_3$, 400 MHz), δ 8.02 (d, J=9.2 Hz, 1H), 7.57 (s, 1H), 7.55 (s, 1H), 7.50-7.53 (m, 1H), 7.40 (s, 1H), 7.38 (s, 1H), 7.20-7.27 (m, 2H), 6.95-7.02 (m, 2H), 6.81 (t, J=6.0 Hz, 1H), 4.63 (d, J=11.6 Hz, 1H), 4.16 (q, J=7.2 Hz, 2H), 3.89-3.95 (m, 4H), 3.63-3.71 (m, 2H), 3.27-3.36 (m, 2H), 2.60 (t, J=6.0 Hz, 2H), 1.62-1.70 (m, 1H), 1.51 (t, J=7.20 Hz, 2H), 1.20-1.28 (m, 4H), 0.97-1.05 (m, 2H), 0.67 (t, J=7.2 Hz, 3H). MS 587 (M+H).

Step F. N-(4-{1-[(4-chlorophenyl)(4-ethyl-6-methoxyquinazolin-2-yl)methyl]butyl}benzoyl)-β-alanine

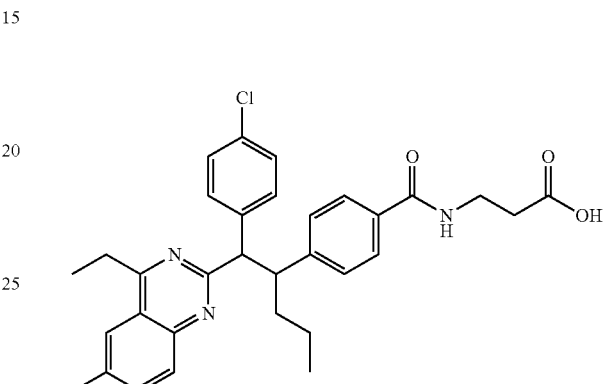

Each of the two diastereomers from Step E (20 mg, 0.036 mmol) were independently dissolved in EtOH (2 mL) then treated with NaOH (1.0 M in water, 0.5 mL, 0.5 mmol). After stirring at room temperature for 4 hours, the solution was diluted with 3M MOH (aq), then extracted with EtOAc (50 mL). The organic layer was dried over anhydrous $Na_2SO_4$, filtered, then concentrated to afford the title compound.

Diastereomer A (derived from less polar ester, more active diastereomer): $^1$H-NMR ($CD_3OD$, 400 MHz), δ 7.87 (d, J=9.2 Hz, 1H), 7.63 (s, 1H), 7.61 (s, 1H), 7.54 (d, J=3.2 Hz, 1H), 7.49-7.52 (m, 3H), 7.29 (s, 1H), 7.27 (s, 1H), 7.01 (s, 1H), 6.99 (s, 1H), 4.47 (d, J=11.2 Hz, 1H), 3.90-4.01 (m, 4l-1), 3.54-3.61 (m, 2H), 2.61 (t, J=7.2 Hz, 2H), 1.62-1.67 (m, 1H), 1.50 (t, J=7.2 Hz, 2H), 1.24-1.32 (m, 1H), 0.95-1.05 (m, 2H), 0.68 (t, 0.1=7.2 Hz, 3H). MS 560 (M+H).

Diastereomer B (derived from more polar ester): $^1$H-NMR ($CD_3OD$, 400 MHz), δ 7.75 (s, 1H), 7.73 (s, 1H), 7.66 (d, J=5.2 Hz, 1H), 7.52 (s, 1H), 7.70 (s, 1H), 7.40-7.45 (m, 1H), 7.32-7.37 (m, 4H), 7.24 (d, J=2.8 Hz, 1H), 4.50 (d, J=11.6 Hz, 1H), 4.11 (q, J=7.2 Hz, 2H), 3.90-3.96 (m, 1H), 3.84 (s 1H), 3.47-3.53 (m, 2H), 3.15-3.22 (m, 2H), 2.52 (t, J=7.2 Hz, 2H), 1.47-1.52 (m, 2H), 1.41 (t, J=7.2 Hz, 2H), 1.00-1.08 (m, 2H), 0.69 (t, J=7.2 Hz, 3H). MS 560 (M+H).

The compounds in TABLE 7 were prepared as racemic mixtures using the chemistry described for the preparation of EXAMPLE 174. The data listed is for the more active diastereomer.

TABLE 7

| EX. | R1 | R2 | MS Data | ¹H NMR data |
|---|---|---|---|---|
| 175 | Et | 7-CF₃ | 598 (M + H) | (CDCl₃, 400 MHz), δ 8.35 (s, 1 H), 8.22 (d, J = 8.8 Hz, 1H), 7.74-7.77 (m, 1 H), 7.61 (s, 1 H), 7.59 (s, 1 H), 7.37 (s, 1 H), 7.35 (s, 1 H), 7.27-7.29 (m, 2 H), 7.02 (s, 1 H), 7.00 (s, 1 H), 6.86 (t, J = 6.0 Hz, 1 H), 4.59 (d, J = 11.2 Hz, 1H), 3.92-3.99 (m, 1 H), 3.71-3.76 (m, 2 H), 3.38-3.42 (m, 2 H), 7.62 (t, J = 6.0 Hz, 2 H), 1.61-1.68 (m, 1 H), 1.51 (t, J = 7.2 Hz, 3 H), 1.36-1.42 (m, 1 H), 0.97-1.05 (m, 2 H), 0.66 (t, J = 7.2 Hz, 3 H). |
| 176 | Et | 5-CF₃ | 598 (M + H) | (CDCl₃, 400 MHz), δ 8.23 (d, J = 8.0 Hz, 1H), 8.03 (d, J = 7.6 Hz, 1H), 7.81-7.86 (m, 1 H), 7.61 (s, 1 H), 7.59 (s, 1 H), 7.36 (s, 1 H), 7.34 (s, 1 H), 7.25 (s, 1 H), 7.23 (s, 1 H), 7.02 (s, 1 H), 7.00 (s, 1 H), 6.84 (t, J = 6.0 Hz, 1 H), 4.57 (d, J = 11.2 Hz, 1H), 3.94-3.97 (m, 1H), 3.70-3.75 (m, 2 H), 3.43-3.49 (m, 2 H), 2.73 (t, J = 6.0 Hz, 2 H), 1.60-1.67 (m, 1 H), 1.46 (t, J = 7.2 Hz, 3 H), 1.30-1.39 (m, 1 H), 0.99-1.04 (m, 2 H), 0.68 (t, J = 7.2 Hz, 3 H). |
| 177 | Et | 6-OCF₃ | 614 (M + H) | (CDCl₃, 400 MHz), δ 8.124 (d, J = 8.0 Hz, 1 H), 7.80-7.88 (m, 2 H), 7.68 (s, 1 H), 7.66 (s, 1 H), 7.54 (s, 1 H), 7.52 (s, 1 H), 7.32-7.38 (m, 4 H), 7.17 (s, 1 H), 5.02 (d, J = 11.6 Hz, 1 H), 3.84-3.92 (m, 1 H), 3.57-3.62 (m, 2 H), 3.30-3.39 (m, 2 H), 2.61 (t, J = 6.0 Hz, 2 H), 1.47-1.56 (m, 5 H), 0.98-1.04 (m, 2 H), 0.73 (t, J = 7.2 Hz, 3 H). |
| 178 | Cyclohexyl | 6-OMe | 614 (M + H) | (CD₃OD, 400 MHz), δ 7.88 (d, J = 9.2 Hz, 1 H), 7.27-7.65 (m, 9 H), 7.03 (d, J = 8.4 Hz, 1 H), 4.45 (d, J = 11.6 Hz, 1 H), 3.94-4.01 (m, 4 H), 3.62-3.70 (m, 1 H), 3.58 (t, J = 7.2 Hz, 2 H), 2.61 (t, J = 7.2 Hz, 2 H), 1.86-2.08 (m, 8 H), 1.45-1.74 (m, 4 H), 0.95-1.10 (m, 2 H), 0.72 (t, J = 7.2 Hz, 3 H) |
| 179 | Cyclohexyl | 7-CF₃ | 652 (M + H) | (CDCl₃, 400 MHz), δ 8.32 (s, 1 H), 8.25 (d, J = 8.8 Hz, 1 H), 7.74 (d, J = 8.8 Hz, 1 H), 7.00-7.65 (m, 8 H), 6.85 (t, J = 5.8 Hz, 1 H), 4.55 (d, J = 11.6 Hz, 1 H), 3.90-3.98 (m, 1 H), 3.72 (q, J = 5.6 Hz, 2 H), 3.52-3.60 (m, 1 H), 2.72 (t, J = 5.8 Hz, 2 H), 1.81-2.05 (m, 8 H), 1.43-1.69 (m, 4 H), 0.94-1.06 (m, 2 H), 0.69 (t, J = 7.2 Hz, 3 H). |
| 180 | Cyclohexyl | 6-OCF₃ | 668 (M + H) | (CD₃OD, 400 MHz), δ 8.165 (d, J = 1.6 Hz, 1 H), 8.08 (d, J = 9.2 Hz, 1 H), 7.88 (dd, J = 8.8, 5.6 Hz, 1 H), 7.02-7.65 (m, 8 H), 4.53 (d, J = 11.6 Hz, 1 H), 3.95-4.05 (m, 1 H), 3.55-3.70 (m, 3 H), 2.61 (t, J = 6.8 Hz, 2 H), 1.83-2.05 (m, 7 H), 1.30-1.70 (m, 5 H), 1.00-1.10 (m, 2 H), 0.74 (t, J = 7.2 Hz, 3 H). |
| 181 | 4-(OMe)Ph | 6-OMe | 638 (M + H) | (CD₃OD, 400 MHz), δ 7.52-7.76 (m, 5 H), 7.10-7.45 (m, 10 H), 4.58 (d, J = 11.6 Hz, 1 H), 3.87-3.96 (m, 4 H), 3.72 (s, 3 H), 3.50 (t, J = 6.8 Hz, 2 H), 2.51 (t, J = 6.8 Hz, 2 H), 1.45-1.65 (m, 2 H), 0.98-1.06 (m, 2 H), 0.72 (t, J = 6.8 Hz, 3 H). |
| 182 | 4-(OMe)Ph | 7-CF₃ | 676 (M + H) | (CD₃CN, 400 MHz), δ 8.11-8.17 (m, 1 H), 7.65-7.36 (m, 5 H), 7.30-7.50 (m, 6 H), 6.95-7.13 (m, 3 H), 4.71 (d, J = 11.6 Hz, 1 H), 3.88-3.98 (m, 4 H), 3.47 (q, J = 6.4 Hz, 2 H), 2.49 (t, J = 6.6 Hz, 2 H), 1.40-1.68 (m, 2 H), 0.96-1.06 (m, 2 H), 0.72 (t, J = 7.4 Hz, 3 H). |
| 183 | 4-(OMe)Ph | 5-CF₃ | 676 (M + H) | (CD₃CN, 400 MHz), δ 8.04 (dd, J = 1.6, 8 Hz, 1 H), 7.70-7.95 (m, 4 H), 6.95-7.46 (m, 10 H), 4.60 (d, J = 11.6 Hz, 1 H), 3.81-3.87 (m, 4 H), 3.46 (q, J = 6.4 Hz, |

TABLE 7-continued

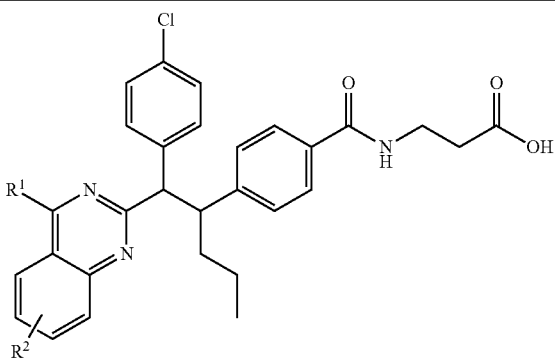

| EX. | R1 | R2 | MS Data | $^1$H NMR data |
|---|---|---|---|---|
| | | | | 2 H), 2.49 (t, J = 6.6 Hz, 2 H), 1.55-1.65 (m, 1 H), 1.41-1.50 (m, 1 H), 0.96-1.03 (m, 2 H), 0.72 (t, J = 7.4 Hz, 3 H). |
| 184 | 4-(OMe)Ph | 6-OCF$_3$ | 692 (M + H) | (CD$_3$OD, 400 MHz), δ 7.98 (dd, J = 8.4, 2.0 Hz, 1 H), 7.15-7.80 (m, 14 H), 4.67 (d, J = 11.6 Hz, 1 H), 3.90-4.00 (m, 4 H),k 3.50 (t, J = 6.8 Hz, 2 H), 2.53 (t, J = 6.8 Hz, 2 H), 1.47-1.65 (m, 2 H), 1.00-1.10 (m, 2 H), 0.75 (t, J = 7.2 Hz, 3 H). |

Example 185

N-[4-{(1S)-1-(4-Cyclopentylphenyl)[7-(Trifluoromethyl)Quinolin-3-Yl]Methyl}Butyl)Benzoyl]-β-Alanine

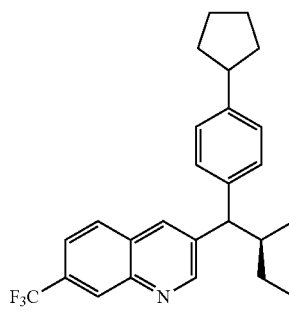

Step A. tert-Butyl 4-{(1S)-1-[(4-chlorophenyl)-(7-trifluoromethylquinolin-3-yl)methyl]butyl}benzoate

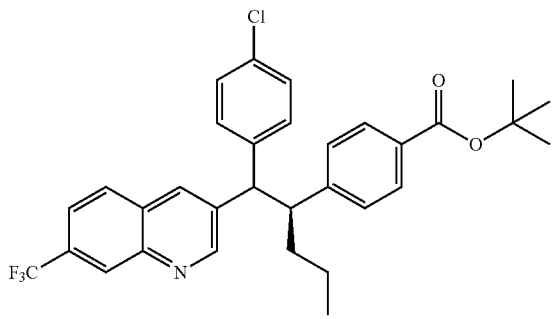 [SMILES: CCC[C@H](c1ccc(C(=O)OC(C)(C)C)cc1)C(c1ccc(Cl)cc1)c1cnc2cc(C(F)(F)F)ccc2c1]

Using the procedures from EXAMPLE 1, Step B, Method (b), 4-{(1S)-1-[(4-chlorophenyl)-(7-trifluoromethylquinolin-3-yl)methyl]butyl}benzoic acid (EXAMPLE 3, Step A) was converted to the title compound as a 1:1 mixture of diastereomers by $^1$H NMR. LC4 3.09 min. (M+H) 554.

Step B. Methyl 4-{(1S)-1-[(4-bromophenyl)-(7-trifluoromethylquinolin-3-yl)methyl]butyl}benzoate

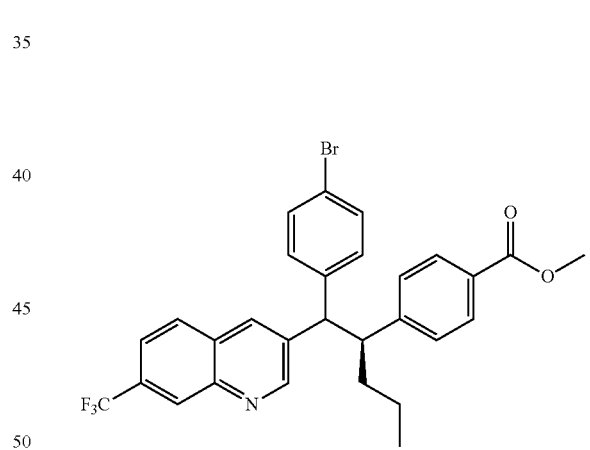

A suspension of tert-butyl 4-{(1S)-1-[(4-chlorophenyl)-(7-trifluoromethylquinolin-3-yl)methyl]butyl}benzoate (200 mg, 0.361 mmol) and NiBr$_2$ (158 mg, 0.722 mmol) in DMF (0.70 mL) was heated at 170° C. for 15 minutes in a microwave reactor. The mixture was diluted with water then extracted with EtOAc. The organic phase was washed with saturated NaCl (aq), dried over MgSO$_4$, filtered, then concentrated. The resulting material was used directly in the next step. LC4 2.69 min. (M+H) 542.

Trimethylsilyl diazomethane (2.0 M in hexanes, 0.2 mL, 0.4 mmol) was added to a solution of the residue from the previous step in methanol (1.0 mL) and benzene (2.0 mL). After stirring at room temperature for 30 minutes, the solution was concentrated. The residue was purified by silica gel chromatography eluting with 0-20% EtOAc/hexanes to afford the title compound as a light yellow foam as a 1:1 mixture of diastereomers by ¹H NMR. LC4 2.91 min. (M+H) 556.

Step C. Methyl 4-{(1S)-1-(4-cyclopentylphenyl)[7-(trifluoromethyl)quinolin-3-yl]methyl}butyl)benzoate

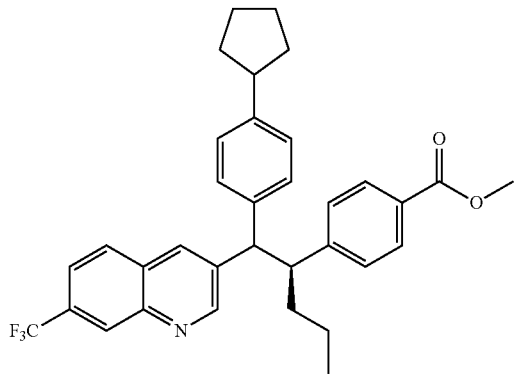 [SMILES: CCC[C@H](c1ccc(C(=O)OC)cc1)C(c1ccc(C2CCCC2)cc1)c1cnc2cc(C(F)(F)F)ccc2c1]

A mixture of methyl 4-{(1S)-1-[(4-bromophenyl)-(7-trifluoromethylquinolin-3-yl)methyl]butyl}benzoate (115 mg, 0.207 mmol), palladium (11) acetate (4.6 mg, 0.021 mmol), n-butyldi-1-adamantylphosphine (15 mg, 0.041 mmol), Cs₂CO₃ (202 mg, 0.620 mmol), and potassium cyclopentyltrifluoroborate (44 mg, 0.25 mmol) in toluene (1.0 mL) and water (0.1 mL) was heated at 100° C. for 24 hours. After being allowed to cool to room temperature, the mixture was diluted with water then extracted with EtOAc. The organic phase was washed with water then saturated NaCl (aq), dried over MgSO₄, filtered, then concentrated. The residue was purified by silica gel chromatography eluting with 0-20% EtOAc/hexanes to afford the title compound as a colorless oil as a 1:1 mixture of diastereomers by ¹H NMR. LC4 3.10 min. (M+H) 546.

Step D. N-[4-((1S)-1-{(4-cyclopentylphenyl)[7-(trifluoromethyl)quinolin-3-yl]methyl}butyl)benzoyl]-β-alanine

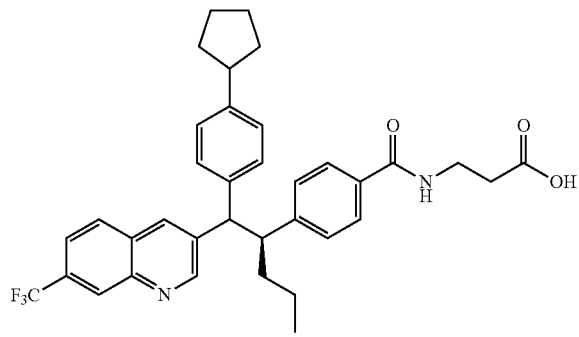 [SMILES: CCC[C@H](c1ccc(C(=O)NCCC(=O)O)cc1)C(c1ccc(C2CCCC2)cc1)c1cnc2cc(C(F)(F)F)ccc2c1]

Using the saponification procedure from EXAMPLE 174 Step E then the coupling and final deprotection procedures from EXAMPLE 1 Step C, methyl 4-((1S)-1-{(4-cyclopentylphenyl)[7-(trifluoromethyl)quinolin-3-yl]methyl}butyl)benzoate was converted to the title compound:

Diastereomer A (from the faster-eluting t-butyl ester precursor) ¹H NMR (500 MHz, CDCl₃): δ 9.29 (s, 1H); 8.56 (s, 1H); 8.44 (s, 1H); 8.08 (d, J=8.6 Hz, 1H); 7.87 (d, J=8.7 Hz, 1H); 7.61 (d, J=7.9 Hz, 2H); 7.23 (d, J=7.9 Hz, 2H); 7.05 (d, J=7.9 Hz, 2H); 6.98 (d, J=8.0 Hz, 2H); 6.87 (t, J=6.1 Hz, 1H); 4.44 (d, J=11.1 Hz, 2H); 3.74-3.63 (m, 3H); 2.85-2.75 (m, 1H); 2.71 (t, J=5.7 Hz, 2H); 1.91 (s, 2H); 1.73-1.65 (m, 2H); 1.64-1.46 (m, 4H); 1.44-1.33 (m, 2H); 1.08-0.99 (m, 2H); 0.71 (t, J=7.3 Hz, 3H). LC4 2.74 min, (M+H) 603.

Diastereomer B (from the slower-eluting t-butyl ester precursor, more active diastereomer) ¹H NMR (500 MHz, CDCl₃): δ 8.95 (s, 1H); 8.39 (s, 1H); 8.22 (s, 1H); 7.92 (d, J=8.7 Hz, 1H); 7.77 (d, J=8.7 Hz, 1H); 7.56 (d, J=7.8 Hz, 2H); 7.35 (d, J=7.9 Hz, 2H); 7.27 (d, J=7.9 Hz, 2H); 7.22 (d, J=7.9 Hz, 2H); 7.01 (t, J=5.9 Hz, 1H); 4.41 (d, J=11.7 Hz, 1H); 3.66-3.55 (m, 3H); 3.02-2.92 (m, 1H); 2.63 (t, J=5.7 Hz, 2H); 2.11-1.98 (m, 2H); 1.83-1.62 (m, 5H); 1.62-1.52 (m, 3H); 1.08-0.99 (m, 2H); 0.75 (t, J=7.3 Hz, 3 Ft). LC4 2.81 min, (M+H) 603.

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. J Biol Chem 272, 7765-9 (1997); Cascieri et al. J Biol Chem 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/−compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. The IC₅₀ values were calculated using non-linear regression analysis assuming single site competition. IC₅₀ values for the compounds of the invention are generally in the range of as low as about 1 nM to as high as about 500 nM, and thus have utility as glucagon antagonists. The IC₅₀ values are shown below in TABLE 8 for the more active isomer of indicated compounds.

TABLE 8

| Example | IC₅₀ (nM) |
| --- | --- |
| 1 | 1.0 |
| 2 | 0.5 |
| 3 | 5.0 |
| 7 | 0.5 |
| 10 | 0.6 |
| 23 | 1.4 |
| 24 | 0.1 |
| 35 | 0.8 |
| 37 | 0.4 |
| 50 | 0.5 |
| 52 | 1.1 |
| 55 | 0.2 |
| 62 | 0.2 |
| 72 | 0.2 |
| 77 | 0.2 |
| 84 | 0.3 |
| 108 | 0.4 |
| 112 | 0.9 |
| 115 | 0.3 |

TABLE 8-continued

| Example | IC$_{50}$ (nM) |
|---|---|
| 120 | 1.8 |
| 131 | 0.5 |
| 138 | 0.4 |
| 139 | 0.3 |
| 146 | 12 |
| 157 | 0.3 |
| 159 | 0.6 |
| 171 | 18 |
| 173 | 1.4 |
| 174 | 1.7 |
| 179 | 4.5 |

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England. Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:
1. A compound represented by formula I:

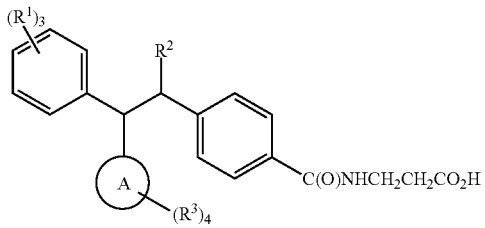

or a pharmaceutically acceptable salt thereof wherein:
ring A represents a quinolinyl group;
each $R^1$ represents H or is selected from the group consisting of halo, CN, OH, NO$_2$, CO$_2R^a$, NR$^a$R$^b$, S(O)$_p$R$^a$, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo and C$_{1-6}$alkoxy;

p represents 0, 1 or 2;
each $R^a$ and $R^b$ independently represents H or C$_{1-4}$alkyl optionally substituted with 1-5 halo atoms up to perhalo; and further optionally substituted with 1 group selected from OH, oxo and C$_{1-6}$alkoxy;
$R^2$ represents C$_{1-6}$alkyl, optionally substituted with 1-5 halo atoms up to perhalo, and
each $R^3$ represents H or is selected from the group consisting of halo, CN, C$_{1-10}$alkyl, and C$_{1-10}$alkoxy, the alkyl portions of C$_{1-10}$alkyl and C$_{1-10}$alkoxy being optionally substituted with 1-5 halo atoms up to perhalo; and further optionally substituted with 1 group selected from NR$^a$R$^b$, and C$_{1-6}$alkoxy;
or 3 $R^3$ groups are as described above and 1 $R^3$ represents a 5-6 membered heteroaryl ring containing 0-1 oxygen or sulfur atom and 1-4 nitrogen atoms, said heteroaryl group being optionally substituted with 1-2 halo, C$_{1-3}$alkyl, or C$_{1-3}$alkoxy groups, the alkyl and portions of C$_{1-3}$alkyl, and C$_{1-3}$alkoxy being optionally substituted with 1-3 halo atoms up to perhalo.

2. A compound in accordance with claim 1 or a pharmaceutically acceptable salt thereof, wherein each $R^1$ represents H or is selected from the group consisting of halo selected from fluoro and chloro, SCH$_3$, CN, C$_{1-6}$alkyl, C$_{2-4}$alkenyl and C$_{1-6}$alkoxy, the alkyl and alkenyl portions of SCH$_3$, C$_{1-6}$alkyl, C$_{2-4}$alkenyl and C$_{1-6}$alkoxy being optionally substituted with 1-3 fluoro atoms.

3. A compound in accordance with claim 2, or a pharmaceutically acceptable salt thereof, wherein each $R^1$ represents H or is selected from the group consisting of: fluoro, chloro, SCH$_3$, CH$_2$, OCH$_3$, CF$_3$, and OCF$_3$.

4. A compound in accordance with claim 3, or a pharmaceutically acceptable salt thereof, wherein each $R^1$ represents H or is selected from the group consisting or: 3-fluoro, 4-fluoro, 5-fluoro, 3-chloro, 4-chloro, 5-chloro, 4-methyl, 4-methoxy, 4-CF$_3$ and 4-OCF$_3$.

5. A compound in accordance with claim 1 or a pharmaceutically acceptable salt thereof wherein R represents a member selected from the group consisting of: CH$_3$, ethyl n-prooyl, isopropyl, n-, s- and t-butyl, isobutyl, neopentyl, and allyl, all optionally substituted with 1-3 fluoro atoms.

6. A compound in accordance with claim 1 or a pharmaceutically acceptable salt thereof wherein $R^2$ represents a member selected from the group consisting of: ethyl, n-propyl and —CH$_2$CH$_2$CF$_3$.

7. A compound in accordance with claim 1 or a pharmaceutically acceptable salt thereof wherein each $R^3$ represents H or is selected from the group consisting of halo, CN, C$_{1-10}$alkyl or C$_{1-10}$alkoxy, the alkyl portions of, C$_{1-10}$alkyl and C$_{1-10}$alkoxy being optionally substituted with 1-5 halo atoms up to perhalo; and further optionally substituted with C$_{1-6}$alkoxy.

8. A compound in accordance with claim 1 or a pharmaceutically acceptable salt thereof, wherein three R groups represent H or halo, and one $R^3$ group represents a 5-6 membered heteroaryl ring containing 0-1 oxygen or sulfur atom and 1-4 nitrogen atoms, said heteroaryl group being optionally substituted with 1-2 halo, C$_{1-3}$alkyl or C$_{1-3}$alkoxy groups, the alkyl portions of, C$_{1-3}$alkyl and C$_{1-3}$alkoxy being optionally substituted with 1-3 halo atoms up to perhalo.

9. A compound in accordance with claim 7 or a pharmaceutically acceptable salt thereof wherein each $R^3$ represents H or is selected from the group consisting of fluoro, chloro; CN, C$_{1-10}$alkyl and C$_{1-10}$alkoxy, the alkyl portions of C$_{1-10}$alkyl and C$_{1-10}$alkoxy being optionally substituted with 1-3 fluoro atoms.

10. A compound in accordance with claim 1 or a pharmaceutically acceptable salt thereof wherein each $R^3$ represents H or is selected from the group consisting of: fluoro, chloro, methyl, ethyl, methoxy, ethoxy, n-propyloxy, isopropyloxy, isobutyloxy, cyclobutyloxy, cyclopentyloxy, cyclohexyloxy methoxyethoxy, dimethylaminoethoxy cyano, trifluoromethyl, trifluoromethoxy, difluoromethoxy.

11. A compound in accordance with claim 1 or a pharmaceutically acceptable sail thereof wherein one $R^3$ represents a 5-6 membered heteroaryl ring containing 0-1 oxygen or sulfur atom and 1-4 nitrogen atoms.

12. A, compound in accordance with claim 1 or a pharmaceutically acceptable salt thereof wherein $R^2$ is selected from the group consisting of; H, Me, Et, n-propyl and n-butyl.

13. A compound in accordance with claim 1 or a pharmaceutically acceptable salt thereof wherein:

ring A represents a quinolinyl group, each $R^1$ represents H or is selected from the group consisting or halo selected from fluoro and chloro: $SCH_3$; CN, $C_{1-6}$alkyl, $C_{2-4}$alkenyl and $C_{1-6}$alkoxy, the alkyl and alkenyl portions of $SCH_3$, $C_{1-6}$alkyl, $C_{2-4}$alkenyl and $C_{1-6}$alkoxy being optionally substituted with 1-3 fluoro atoms, $R^2$ represents a member selected from the group consisting of: $CH_3$, ethyl, n-propyl, isopropyl, n-, s- and t-butyl, isobutyl neopentyl, and allyl, all optionally substituted with 1-3 fluoro atoms;

each $R^3$ represents H or is selected from the group consisting of halo, CN, $C_{1-10}$alkyl or $C_{1-10}$alkoxy, the alkyl portions of, $C_{1-10}$alkyl, and $C_{1-10}$alkoxy being optionally substituted with 1-5 halo atoms up to perhalo; and further optionally substitued with $C_{1-6}$alkoxy;

p represents 0, 1 or 2; and each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy.

14. A compound in accordance with claim 1 or a pharmaceutically acceptable salt thereof wherein 1 $R^3$ is selected from the group consisting of: pyrrolo, pyrazole, isoxazolo and dimethylisoxazolo.

15. A compound in accordance with claim 1 or a pharmaceutically acceptable salt thereof wherein the compound is individually selected from the following tables compounds:

TABLE 1-A

EXAMPLE 1

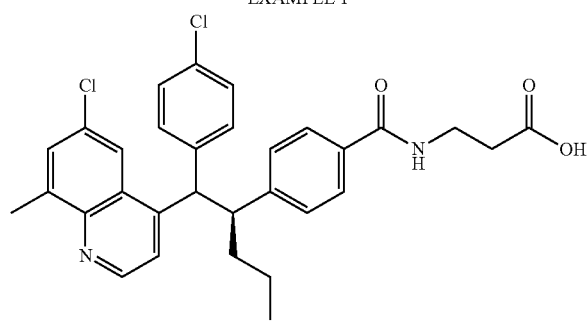

TABLE 1-A-continued

EXAMPLE 2

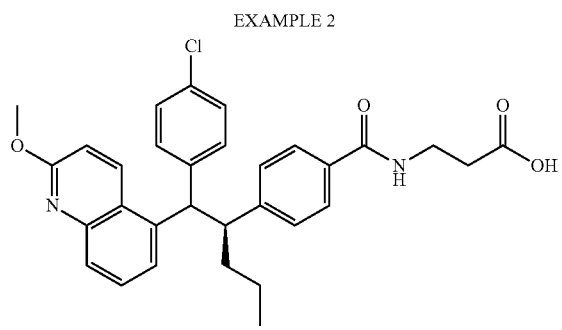

EXAMPLE 3

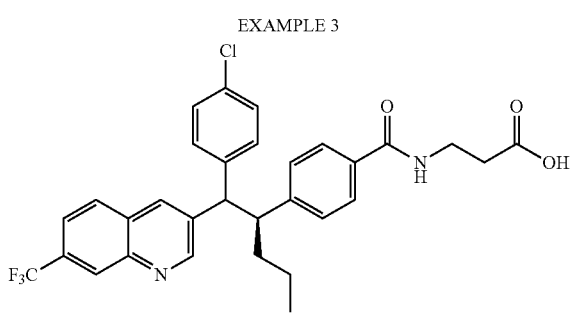

EXAMPLE 157

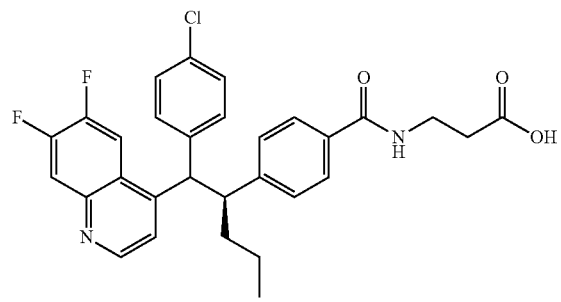 [SMILES: CCC[C@H](c1ccc(C(=O)NCCC(=O)O)cc1)C(c1ccc(Cl)cc1)c1ccnc2cc(F)c(F)cc12]

EXAMPLE 169

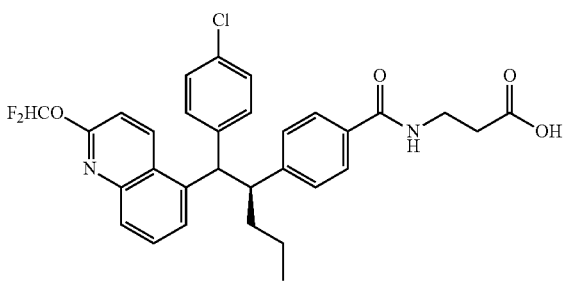 [SMILES: CCC[C@H](c1ccc(C(=O)NCCC(=O)O)cc1)C(c1ccc(Cl)cc1)c1cccc2nc(OC(F)F)ccc12]

EXAMPLE 170

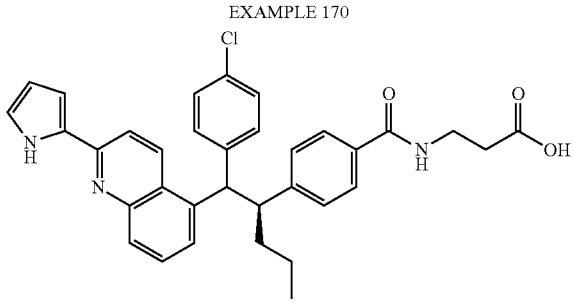

TABLE 1-A-continued

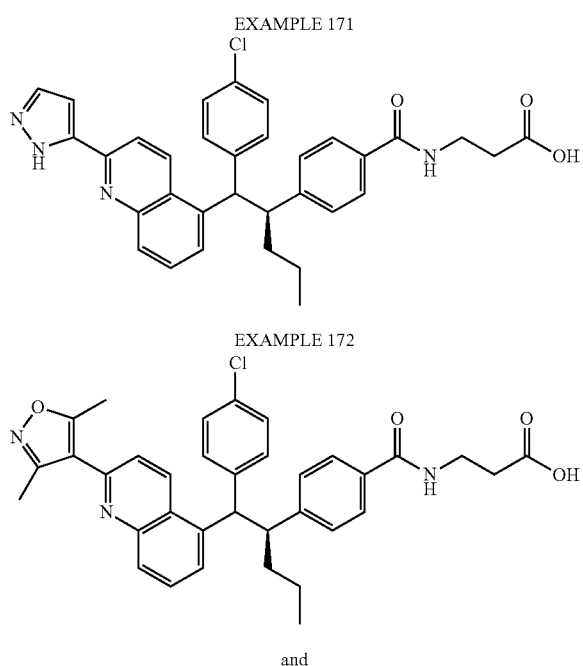

EXAMPLE 171

EXAMPLE 172 and

TABLE 1-A-continued

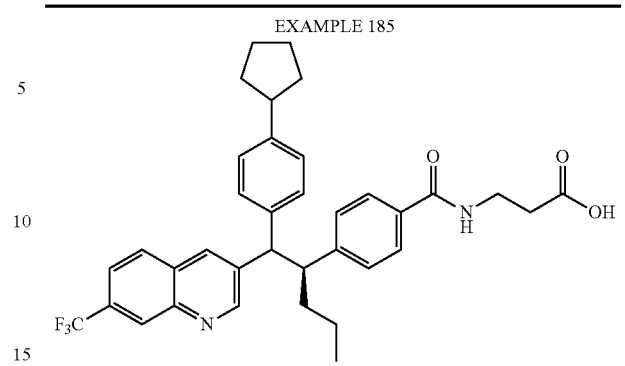

EXAMPLE 185 or a pharmaceutically acceptable salt thereof.

16. A pharmaceutical composition comprising a compound in accordance with claim 1 or a pharmaceutically acceptable salt thereof in combination with a pharmaceutically acceptable carrier.

17. A method of treating type 2 diabetes mellitus in a mammalian patient in need of such treatment comprising administering to said patient a compound in accordance with claim 1 or a pharmaceutically acceptable salt thereof in an amount that is effective to treat said type 2 diabetes mellitus.

* * * * *